US007101857B2

(12) United States Patent
Sung et al.

(10) Patent No.: US 7,101,857 B2
(45) Date of Patent: Sep. 5, 2006

(54) CROSSLINKABLE BIOLOGICAL MATERIAL AND MEDICAL USES

(75) Inventors: Hsing-Wen Sung, Hsinchu (TW); Huang-chien Liang, Hsinchu (TW); Hosheng Tu, Newport Beach, CA (US)

(73) Assignee: GP Medical, Inc., Newport Beach, CA (US)

( * ) Notice: Subject to any disclaimer, the term of this patent is extended or adjusted under 35 U.S.C. 154(b) by 163 days.

(21) Appl. No.: 10/827,673

(22) Filed: Apr. 19, 2004

(65) Prior Publication Data

US 2005/0124560 A1 Jun. 9, 2005

Related U.S. Application Data

(63) Continuation-in-part of application No. 10/408,176, filed on Apr. 7, 2003, which is a continuation-in-part of application No. 10/067,130, filed on Feb. 4, 2002, now Pat. No. 6,545,042, which is a continuation-in-part of application No. 09/297,808, filed as application No. PCT/US97/20113 on Nov. 4, 1997, now Pat. No. 6,608,040.

(60) Provisional application No. 60/552,517, filed on Mar. 12, 2004, provisional application No. 60/547,935, filed on Feb. 26, 2004, provisional application No. 60/526,434, filed on Dec. 2, 2003, provisional application No. 60/518,050, filed on Nov. 7, 2003, provisional application No. 60/492,874, filed on Aug. 6, 2003, provisional application No. 60/030,701, filed on Nov. 5, 1996.

(51) Int. Cl.
*A61K 31/7048* (2006.01)

(52) U.S. Cl. .................. 514/26; 424/423; 424/445; 435/325

(58) Field of Classification Search .................. 514/26; 424/423, 445; 435/325
See application file for complete search history.

(56) References Cited

U.S. PATENT DOCUMENTS

| 4,806,595 | A |   | 2/1989  | Noishiki et al. |
|-----------|---|---|---------|-----------------|
| 4,808,402 | A | * | 2/1989  | Leibovich et al. ........ 424/78.06 |
| 5,270,446 | A |   | 12/1993 | Kyogoku et al. |
| 5,332,935 | A |   | 7/1994  | Smith |
| 5,573,784 | A |   | 11/1996 | Badylak et al. |
| 5,663,160 | A | * | 9/1997  | Meybeck et al. ............ 514/182 |
| 5,874,417 | A | * | 2/1999  | Prestwich et al. ............ 514/54 |
| 5,929,038 | A |   | 7/1999  | Chang |
| 6,051,750 | A |   | 4/2000  | Bell |
| 6,103,255 | A |   | 8/2000  | Levene et al. |
| 6,162,826 | A |   | 12/2000 | Moon et al. |
| 6,262,083 | B1 |  | 7/2001  | Moon et al. |
| 6,264,992 | B1 |  | 7/2001  | Voytik-Harbin et al. |
| 6,340,480 | B1 |  | 1/2002  | Duckett et al. |
| 6,485,723 | B1 |  | 11/2002 | Badylak et al. |
| 6,506,398 | B1 |  | 1/2003  | Tu et al. |
| 6,545,042 | B1 |  | 4/2003  | Sung et al. |
| 6,608,040 | B1 |  | 8/2003  | Lin et al. |
| 6,624,138 | B1 |  | 9/2003  | Sung et al. |

FOREIGN PATENT DOCUMENTS

| JP | 406239759   | * | 8/1994 |
| WO | WO 94/17227 | * | 8/1994 |

OTHER PUBLICATIONS

Malone et al, J. Vasc. Surg. 1984, 1, 181-191.*
Courtman et al, J. Biomedical Materials Research, 1994, 28, 655-661.*
Morisaki et al , British Journal of Pharmacology, 1995, 115, 1186-93.*
Malone et al , J. Vasc. Surg., 1984, 1, 181-191.*
Sung HW et al., J Biomed Mater Res 1998; 42 : 560-567.
Huang LLH et al., J Biomed Mater Res 1998; 42 : 568-576.
Sung HW et al., J Biomater Sci Polymer Edn 1998; 10(1): 63-78.
Sung HW et al., J Biomater Sci Polymer Edn 1999; 10 (7): 751-771.
Sung HW et al., J Biomed Mater Res 1999; 46 : 520-530.
Sung HW et al., J Biomed Mater Res 1999; 47 : 116-126.
Sung H W et al., Biomaterials 1998; 20 : 1759-1772.
Sung HW et al., Biomaterials 2001; 21 : 1353-1362.
Tsai CC et al., J Biomed Mater Res 2000; 52 : 58-65.
Mi FL et al., J Polym Sci A : Polym Chem 2000; 58 : 2804-2814.
Tsai CC et al., Biomaterials 2001; 22 : 523-533.
Mi FL et al., J Appl Polym Sci 2001;81 : 1700-1711.
Sung HW et al., J Biomed Mater Res 2001; 55 : 538-546.
Mi FL et al., J Biomater Sci Polymer Edn 2001; 12(8) : 835-850.
Mi FL et al., Biomaterials 2002; 23 : 181-191.
Mi FL et al., Carbohydrate Polymers 2002; 48 : 61-72.
Chang Y et al., Biomaterials 2002; 23 : 2447-2457.
Liang HC et al., J. Biomed Mater Res 2003; 65A : 271-282.

* cited by examiner

*Primary Examiner*—Shaojia Jiang
*Assistant Examiner*—Ganapathy Krishnan

(57) ABSTRACT

A method for promoting angiogenesis in a patient comprising providing crosslinkable biological solution to the target tissue, wherein the crosslinkable biological solution is loaded with at least one angiogenic agent. In one embodiment, the at least one angiogenic agent is a non-protein factor selected from a group consisting of ginsenoside $Rg_1$, ginsenoside Re, combination thereof and the like. In another embodiment, the crosslinkable biological solution of the present invention is broadly defined in a form or phase of solution, paste, gel, suspension, colloid or plasma that may be solidifiable thereafter.

8 Claims, 33 Drawing Sheets

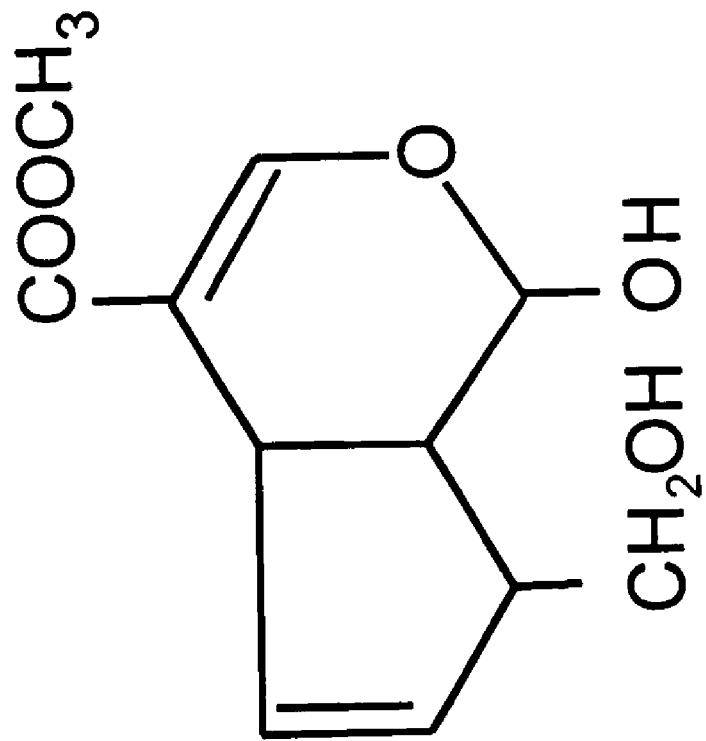
Genipin (GP)
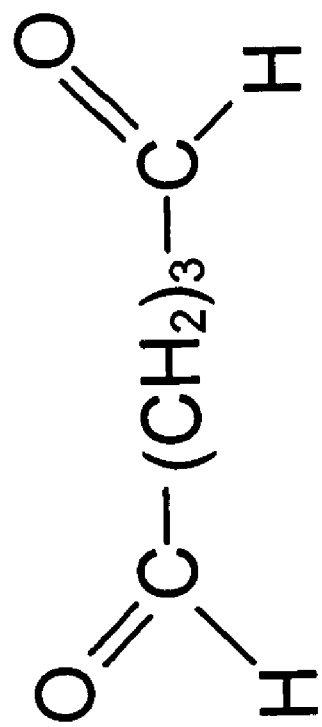
Glutaraldehyde (GA)
FIG. 1

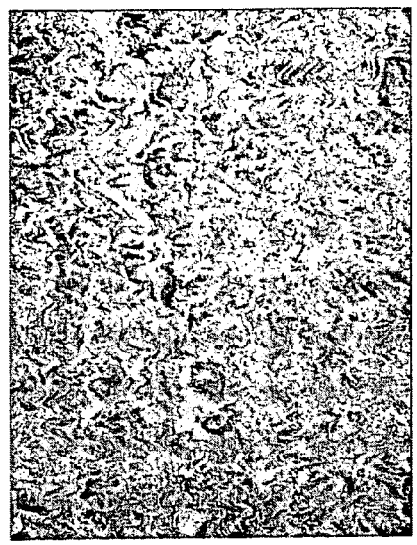
(b) Specimen-B
(d) Specimen-D
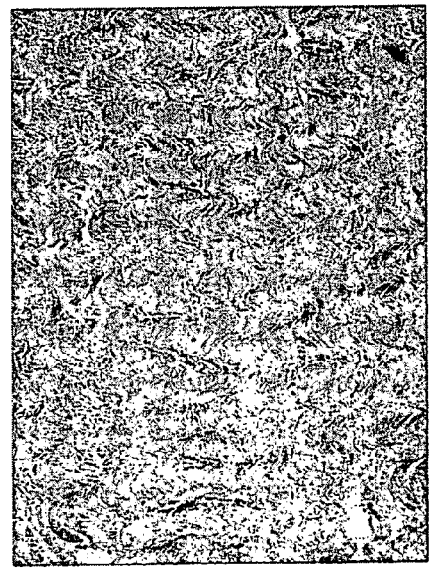
(a) Specimen-A
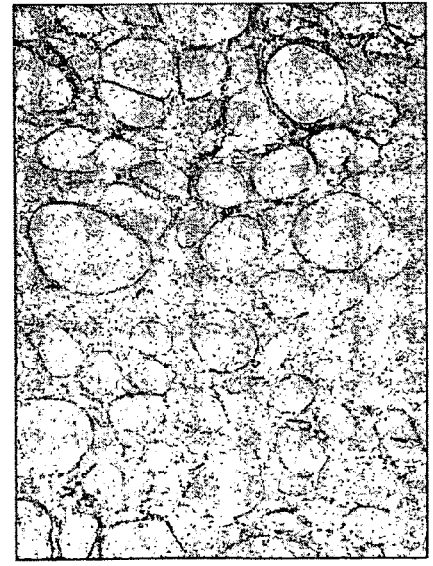
(c) Specimen-C
FIG. 2

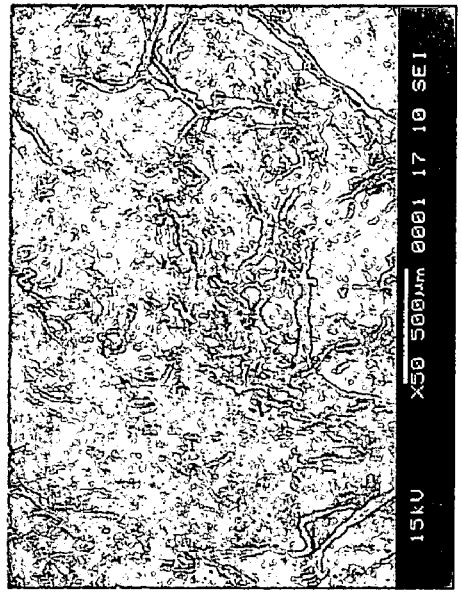
(a) Specimen-A
(b) Specimen-B
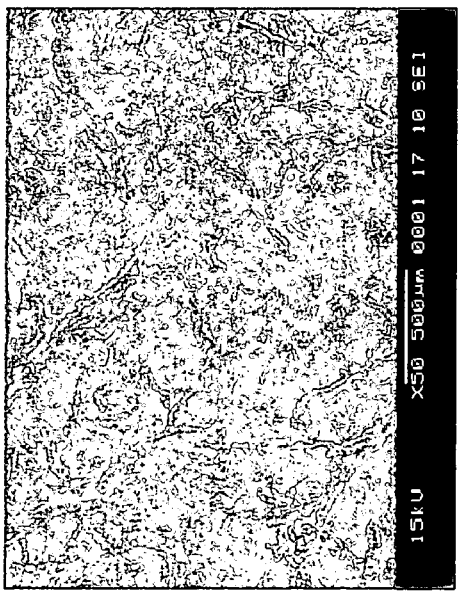
(c) Specimen-C
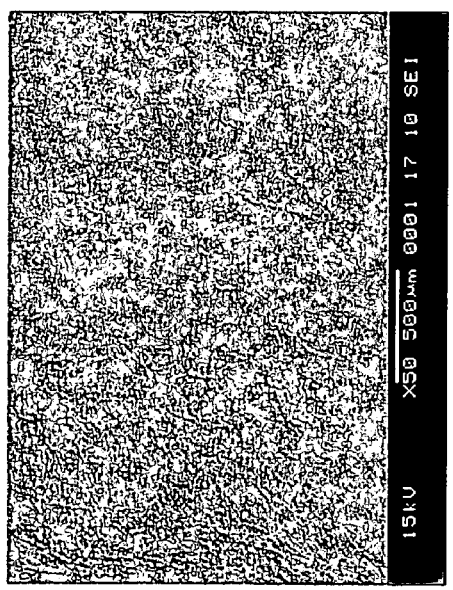
(d) Specimen-D
FIG. 3

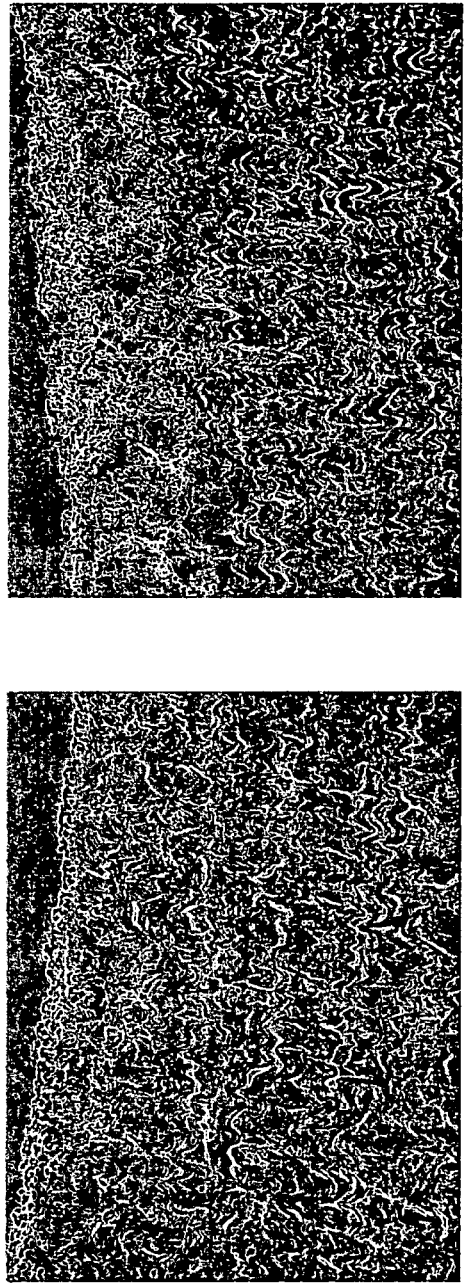
FIG. 8

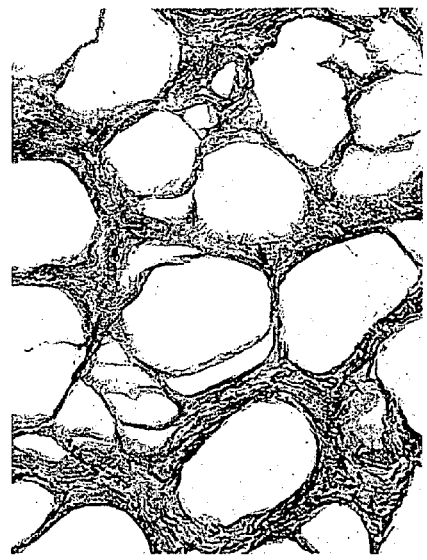
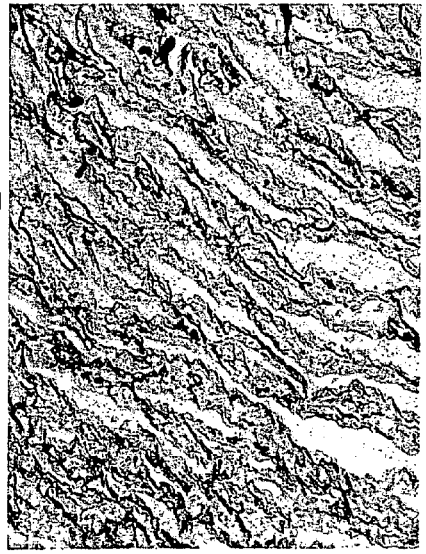
4-Week Postoperatively (Masson Trichrome) FIG. 15

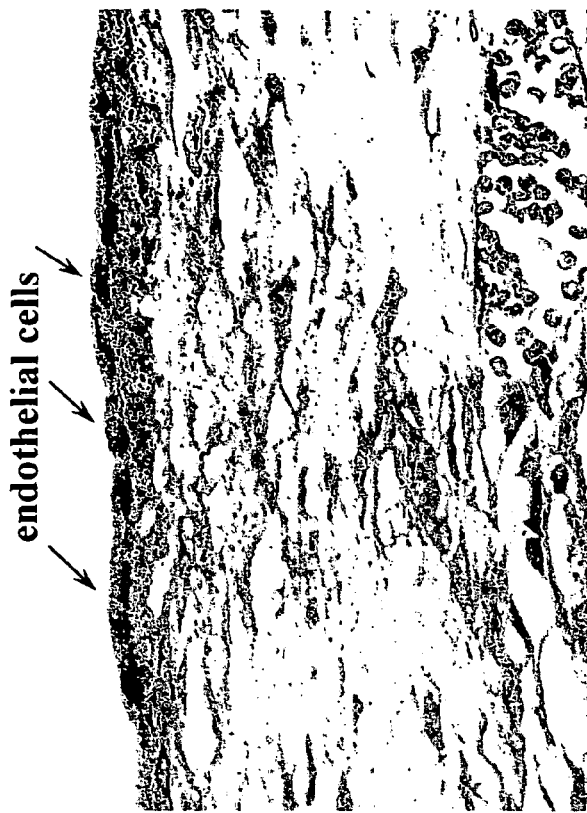
FIG. 16

CROSSLINKABLE BIOLOGICAL MATERIAL AND MEDICAL USES

CROSS-REFERENCE TO RELATED APPLICATIONS

This application is a continuation-in-part application of U.S. patent application Ser. No. 10/408,176 filed Apr. 7, 2003, entitled "Acellular Biological Material", which is a continuation-in-part application of application Ser. No. 10/067,130 filed Feb. 4, 2002, entitled "Acellular Biological Material Chemically Treated with Genipin", now U.S. Pat. No. 6,545,042, which is a continuation-in-part application of application Ser. No. 09/297,808 filed Sep. 27, 2001, now U.S. Pat. No. 6,608,040, which is the national stage entry of PCT/US97/20113 filed Nov. 4, 1997, which claims the benefits of a provisional application Ser. No. 60/030,701 filed Nov. 5, 1996. The application also claims the benefits of provisional application Ser. No. 60/492,874 filed Aug. 6, 2003, application Ser. No. 60/518,050 filed Nov. 7, 2003, application Ser. No. 60/526,434 filed Dec. 2, 2003, application Ser. No. 60/547,935 filed Feb. 26, 2004, and application Ser. No. 60/552,517 filed Mar. 12, 2004. Entire contents of all the above co-pending applications are incorporated herein by reference.

FIELD OF THE INVENTION

The present invention generally relates to chemical modification of biomedical materials, such as collagen matrix with a naturally occurring crosslinking reagent, genipin. More particularly, the present invention relates to crosslinkable biological solution as medical material prepared with bioactive agents and the crosslinking reagent, genipin, its derivatives or analog and the process thereof.

BACKGROUND OF THE INVENTION

Crosslinking of biological molecules is often desired for optimum effectiveness in biomedical applications. For example, collagen, which constitutes the structural framework of biological tissue, has been extensively used for manufacturing bioprostheses and other implanted structures, such as vascular grafts, wherein it provides a good medium for cell infiltration and proliferation. However, biomaterials derived from collagenous tissue must be chemically modified and subsequently sterilized before they can be implanted in humans. The fixation, or crosslinking, of collagenous tissue increases strength and reduces antigenicity and immunogenicity.

Collagen sheets are also used as wound dressings, providing the advantages of high permeability to water vapor and rapid wound healing. Disadvantages include low tensile strength and easy degradation of collagen by collagenase. Crosslinking of collagen sheets reduces cleavage by collagenase and improves tensile strength.

Clinically, biological tissue has been used in manufacturing heart valve prostheses, small-diameter vascular grafts, and biological patches, among others. However, the biological tissue has to be fixed with a crosslinking or chemically modifying agent and subsequently sterilized before they can be implanted in humans. The fixation of biological tissue is to reduce antigenicity and immunogenicity and prevent enzymatic degradation. Various crosslinking agents have been used in fixing biological tissue. These crosslinking agents are mostly synthetic chemicals such as formaldehyde, glutaraldehyde, dialdehyde starch, glyceraldehydes, cyanamide, diimides, diisocyanates, and epoxy compound. However, these chemicals are all highly cytotoxic which may impair the biocompatibility of biological tissue. Of these, glutaraldehyde is known to have allergenic properties, causing occupational dermatitis and is cytotoxic at concentrations greater than 10–25 ppm and as low as 3 ppm in tissue culture. It is therefore desirable to provide a crosslinking agent suitable for use in biomedical applications that is within acceptable cytotoxicity and that forms stable and biocompatible crosslinked products.

To achieve this goal, a naturally occurring crosslinking agent (genipin) has been used to fix biological tissue or crosslinkable biological solution. The co-pending application Ser. No. 09/297,808 filed Sep. 27, 2001, entitled "Chemical modification of biomedical materials with genipin" is incorporated and cited herein by reference. The cytotoxicity of genipin was previously studied in vitro using 3T3 fibroblasts, indicating that genipin is substantially less cytotoxic than glutaraldehyde (Sung H W et al., J Biomater Sci Polymer Edn 1999; 10:63–78). Additionally, the genotoxicity of genipin was tested in vitro using Chinese hamster ovary (CHO-K1) cells, suggesting that genipin does not cause clastogenic response in CHO-K1 cells (Tsai C C et al., J Biomed Mater Res 2000; 52:58–65). A biological material treated with genipin resulting in acceptable cytotoxicity is key to biomedical applications.

It is further hypothesized in the literature that acellular tissue might remove cellular antigens (Wilson G J et al., Trans Am Soc Artif Intern 1990; 36:340–343). As a means for reducing the antigenic response to xenograft material, cell extraction removes lipid membranes and membrane-associated antigens as well as soluble proteins. Courtman et al. developed a cell extraction process to render bovine pericardium free of cells and soluble proteins, leaving a framework of largely insoluble collagen and elastin (Courtman D W et al., J Biomed Mater Res 1994; 28:655–666). They hypothesized that this process may decrease the antigenic load within the material, reducing the associated degradation due to in vivo cellular attack, and possibly eliminating the need for extensive crosslinking. Additionally, acellular tissue may provide a natural microenvironment for host cell migration to accelerate tissue regeneration (Malone J M et al., J Vasc Surg 1984; 1:181–91).

Other than maintaining a natural microenvironment, the collagen matrix, including soluble collagen, after being treated with the proposed cell extraction process, the collagen matrix shall have similar properties of decreased antigenicity/immunogenicity. However, the framework of largely insoluble collagen and elastin matrix is still vulnerable to enzymatic degradation and is not suitable as an implantable bioprosthesis.

As is well known that the human knee comprises an articulation of the femur, the tibia and the patella. The femur and the tibia are maintained in a condition of stable articulation by a number of ligaments of which the principal ones are the anterior and posterior cruciate ligaments and the collateral ligaments. The rupture of the anterior cruciate ligament is relatively commonly encountered as a result of sporting injury or the like. This rupture leads to knee instability and can be a debilitating injury. Though less common, the rupture of the posterior cruciate ligament can be equally disabling.

In the past, polymer or plastic materials have been studied as ligament or tendon replacements. Prosthetic ligament replacements made of carbon fibers and Gore-Tex PTFE materials do not last a long period of time. Repeated loading of a prosthetic ligament in a young active patient leads to failure of the ligament. It has been found that it is difficult to provide a tough durable plastic material which is suitable for long-term connective tissue replacement. Plastic material could become infected and difficulties in treating such infections often lead to graft failure.

In accordance with the present invention, there is provided genipin treated tissue grafts for orthopedic and other surgical applications, such as vascular grafts and heart valve bioprostheses, which have shown to exhibit many of the desired characteristics important for optimal graft function. In particular, the tissue regeneration capability in the genipin-fixed acellular tissue may be suitable as a graft material for bone, tendon, ligament, cartilage, muscle, and cardiovascular applications.

In some aspects of the invention, it is provided a method for promoting autogenous ingrowth of a biological tissue material, comprising providing a natural tissue, removing cellular material from the natural tissue, increasing porosity of the natural tissue by at least 5%, loading an angiogenesis agent or autologous cells into the porosity, and crosslinking the natural tissue with a crosslinking agent.

Some aspects of the invention relate to crosslinkable biological solution configured and adapted for promoting angiogenesis, wherein the crosslinkable biological solution is incorporated with an organic angiogenic agent such as ginsenoside $Rg_1$, ginsenoside Re or the like.

SUMMARY OF THE INVENTION

In general, it is an object of the present invention to provide a biological scaffold configured and adapted for tissue regeneration or tissue engineering. In one embodiment, the process of preparing a biological scaffold comprises steps of removing cellular material from a natural tissue and crosslinking the natural tissue with genipin, wherein the scaffold is characterized by reduced antigenicity, reduced immunogenicity and reduced enzymatic degradation upon placement inside a patient's body. The "tissue engineering" in this invention may include cell seeding, cell ingrowth and cell proliferation into the scaffold or collagen matrix in vivo or in vitro.

It is another object of the present invention to provide a tendon or ligament graft for use as connective tissue substitute, wherein the graft is formed from a segment of connective tissue protein, and the segment is crosslinked with genipin, its analog or derivatives resulting in reasonably acceptable cytotoxicity and reduced enzymatic degradation.

It is a further object of the present invention to provide a method for promoting autogenous ingrowth of damaged or diseased tissue selected from a group consisting of bone, ligaments, tendons, muscle and cartilage, the method comprising a step of surgically repairing the damaged or diseased tissue by attachment of a tissue graft, wherein the graft is formed from a segment of connective tissue protein, the segment being crosslinked with genipin, its analog or derivatives with acceptable cytotoxicity and reduced enzymatic degradation, and wherein the tissue graft is loaded with growth factors or bioactive agents.

In some aspects, there is provided a biological tissue material configured and adapted for tissue regeneration comprising steps of removing cellular material from a natural tissue and crosslinking the natural tissue with a crosslinking agent, the tissue material being characterized by reduced antigenicity, reduced immunogenicity and reduced enzymatic degradation upon placement inside a patient's body, wherein porosity of the natural tissue is increased by at least 5%, the increase of porosity being adapted for promoting tissue regeneration. In a preferred embodiment, the tissue material is selected from a group consisting of a tissue valve, a tissue valve leaflet, a vascular graft, a ureter, a urinary bladder, a dermal graft, and the like. In another preferred embodiment, the natural tissue is selected from a group consisting of a porcine valve, a bovine jugular vein, a bovine pericardium, an equine pericardium, a porcine pericardium, submucosal tissue, and the like. In still another embodiment, the crosslinked acellular natural tissue is loaded with growth factors or bioactive agents.

In some aspects, there is provided a method for promoting autogenous ingrowth of a biological tissue material comprising the steps of providing a natural tissue, removing cellular material from the natural tissue, increasing porosity of the natural tissue by at least 5%, and crosslinking the natural tissue with a crosslinking agent. The tissue material is generally characterized by reduced antigenicity, reduced immunogenicity and reduced enzymatic degradation upon placement inside a patient's body. In one embodiment, the crosslinked acellular natural tissue is loaded with growth factors or bioactive agents.

Some aspects of the invention relate to a method for promoting angiogenesis in a subject in need thereof, comprising administering to the subject a substrate loaded with therapeutically effective amount of a non-protein angiogenesis factor, wherein the non-protein angiogenesis factor may be an organic angiogenesis factor. In one embodiment, the non-protein angiogenesis factor is ginsenoside $Rg_1$, ginsenoside Re or the like extracted from a plant. In another embodiment, the substrate is configured and formulated for administering to the subject by a route selected from a group consisting of oral administration, topical administration, percutaneous injection, intravenous injection, intramuscular injection, oral administration, and implantation.

In one embodiment, the substrate is an acellular tissue or a wound dressing, wherein the acellular tissue may have increased porosity over the substrate by at least 5%. In another embodiment, the method for administering to a subject a substrate loaded with therapeutically effective amount of a non-protein angiogenesis factor comprises a step of crosslinking the substrate with a crosslinking agent. In a further embodiment, the substrate is an artificial organ selected from a group consisting of biological patch, vascular graft, heart valve, venous valve, tendon, ligament, bone, muscle, cartilage, ureter, urinary bladder, dermal graft, cardiac tissue, anti-adhesion membrane, and myocardial tissue.

In some aspects, there is provided a method for promoting autogenous ingrowth of a biological tissue material comprising the steps of providing a natural tissue, removing cellular material from the natural tissue, increasing porosity of the natural tissue by at least 5%, loading an angiogenesis agent or autologous cells into the porosity, and crosslinking the natural tissue with a crosslinking agent. In one preferred embodiment, the angiogenesis agent is ginsenoside $Rg_1$, ginsenoside Re, or selected from the group consisting of VEGF, VEGF 2, bFGF, VEGF121, VEGF165, VEGF189, VEGF206, PDGF, PDAF, TGF-$\beta$, TGF-$\alpha$, PDEGF, PDWHF, epidermal growth factor, insulin-like growth factor, aFGF, human growth factor, and combination thereof.

Some aspects of the invention relate to a method for promoting angiogenesis for treating tissue comprising: providing crosslinkable biological solution to the target tissue, wherein the crosslinkable biological solution is loaded with at least one angiogenic agent (also known as angiogenic growth factor). In one embodiment, the at least one angiogenic agent is a protein factor selected from a group consisting of VEGF, VEGF 2, bFGF, VEGF121, VEGF165, VEGF189, VEGF206, PDGF, PDAF, TGF-β, TGF-α, PDEGF, PDWHF, epidermal growth factor, insulin-like growth factor, aFGF, human growth factor, and combination thereof. In a preferred embodiment, the at least one angiogenic agent is an organic angiogenesis agent selected from a group consisting of ginsenoside $Rg_1$, ginsenoside Re, combination thereof and the like. In another embodiment, the crosslinkable biological solution of the present invention is broadly defined in a form or phase of solution, paste, gel, suspension, colloid or plasma that may be solidifiable thereafter. In still another embodiment, the crosslinkable biological solution of the invention is crosslinkable with a crosslinking agent or with ultraviolet irradiation before, during or after the step of tissue treatment.

Some aspects of the invention relate to a drug-collagen-genipin and/or drug-chitosan-genipin compound that is loadable onto an implant or stent enabling drug slow-release to the surrounding tissue, or to the lumen of the bodily cavity. In one preferred embodiment, the compound is loaded onto the outer periphery of the stent enabling drug slow-release to the surrounding tissue.

Some aspects of the invention provide a method for promoting angiogenesis for treating tissue, comprising: providing crosslinkable biological solution to the target tissue, wherein the crosslinkable biological solution is loaded with at least one angiogenesis factor. It is one object of the present invention to provide a crosslinkable biological solution kit comprising a first readily mixable crosslinkable biological solution component and a second crosslinker component, wherein the first component and the second component are mixed at point of need. In a further embodiment, an operator can add appropriate drugs or bioactive agents to the kit and obtain a drug-collagen-genipin and/or drug-chitosan-genipin compound enabling drug slow-release to the target tissue. In a further embodiment, the crosslinkable biological solution kit is packaged in a form for topical administration, for percutaneous injection, for intravenous injection, for intramuscular injection, for loading on an implant or biological tissue material, and/or for oral administration.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

FIG. 1 is chemical structures of glutaraldehyde and genipin that are used in the chemical treatment examples of the current disclosure.

FIG. 2 are photomicrographs of H&E stained tissue for (a) specimen-A, cellular tissue; (b) specimen-B, acellular tissue; (c) specimen-C, the acid treated acellular tissue; and (d) specimen-D, the enzyme treated acellular tissue.

FIG. 3 shows the SEM of bovine pericardia tissue for (a) specimen-A, cellular tissue; (b) specimen-B, acellular tissue; (c) specimen-C, the acid treated acellular tissue; and (d) specimen-D, the enzyme treated acellular tissue.

FIG. 8 are photomicrographs of H&E stained genipin-crosslinked tissue for (a) specimen-A/GP, cellular tissue; (b) specimen-B/GP, acellular tissue; (c) specimen-C/GP, the acid treated acellular tissue; and (d) specimen-D/GP, the enzyme treated acellular tissue retrieved at 3-day postoperatively.

FIG. 15 is 4-week postoperative results on animal myocardial patch study of FIG. 14: photomicrographs of Masson Trichrome stained tissue.

FIG. 16 is 4-week postoperative results on animal myocardial patch study of FIG. 14: photomicrographs of Factor VIII stained tissue.

DETAILED DESCRIPTION OF EXEMPLARY EMBODIMENTS

Figure 4:
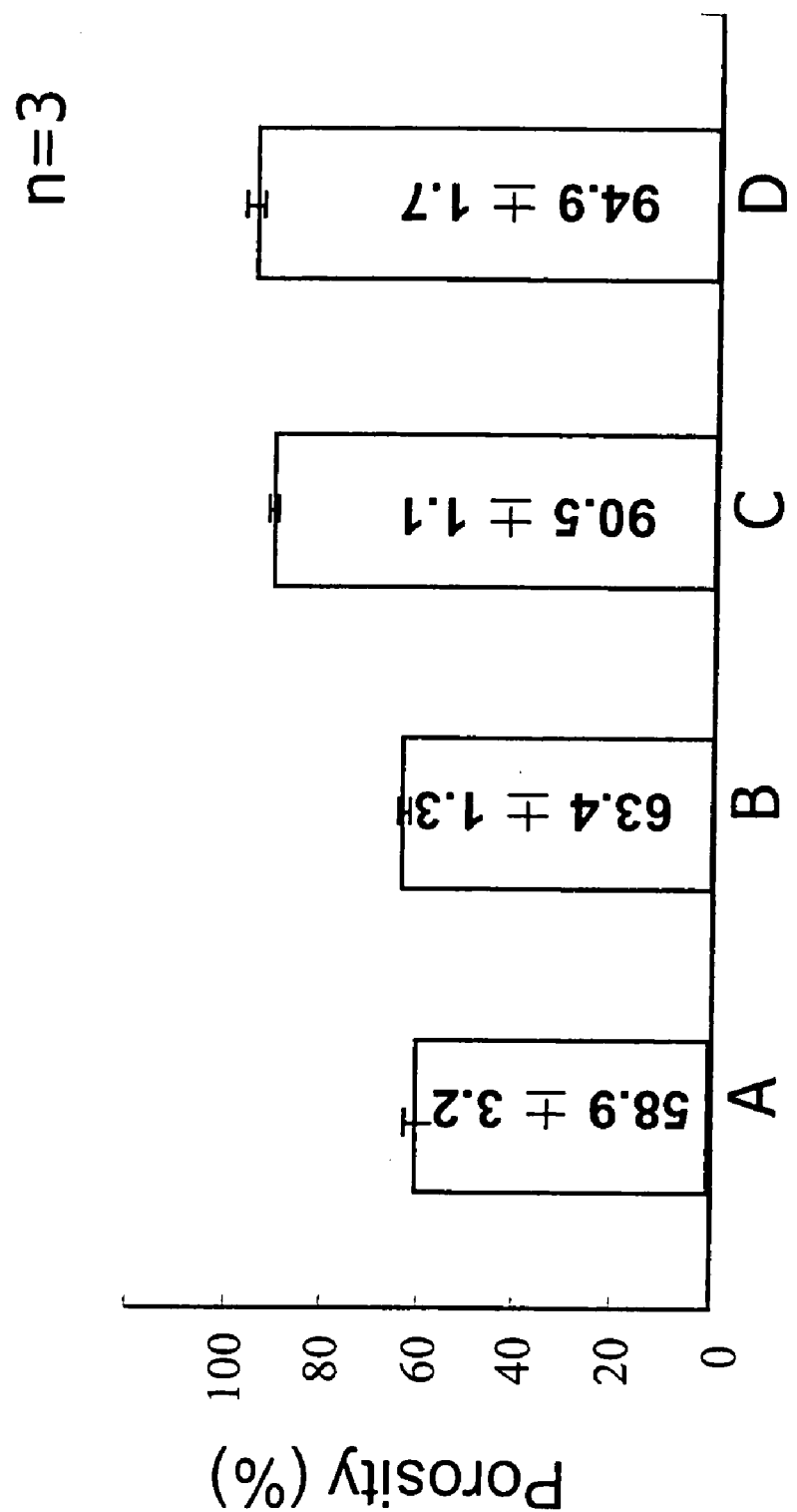
FIG. 4 shows porosity of bovine pericardia tissue for (a) specimen-A, cellular tissue; (b) specimen-B, acellular tissue; (c) specimen-C, the acid treated acellular tissue; and (d) specimen-D, the enzyme treated acellular tissue.

The following detailed description is of the best presently contemplated modes of carrying out the invention. This description is not to be taken in a limiting sense, but is made merely for the purpose of illustrating general principles of embodiments of the invention.

"Genipin" in this invention is meant to refer to the naturally occurring compound as shown in FIG. 1 and its derivatives, analog, stereoisomers and mixtures thereof.

"Tissue engineering" or "tissue regeneration" in meant to refer to cell seeding, cell ingrowth and cell proliferation into the acellular scaffold or collagen matrix in vivo or in vitro, sometimes enhanced with an angiogenesis factor.

A "biological tissue material" refers to a biomedical material or device of biological tissue origin which is inserted into, or grafted onto, bodily tissue to remain for a period of time, such as an extended-release drug delivery device, tissue valve, tissue valve leaflet, vascular or dermal graft, ureter, urinary bladder, or orthopedic prosthesis, such as bone, ligament, tendon, cartilage, and muscle.

"Crosslinkable biological solution" is herein meant to refer to collagen extract, soluble collagen, elastin, gelatin, chitosan, N, O, carboxylmethyl chitosan (NOCC), chitosan-containing and other collagen-containing biological solution. For a preferred aspect of the present invention, the biological solution is meant to indicate a crosslinkable biological substrate that may comprise at least a genipin-crosslinkable functional group, such as amino group or the like, or crosslinkable with UV irradiation. The crosslinkable biological solution of the present invention is broadly defined in a form or phase of solution, paste, gel, suspension, colloid or plasma that may be solidifiable thereafter.

An "implant" refers to a medical device (of biological and non-biological origin) which is inserted into, or grafted onto, bodily tissue to remain for a period of time, such as an extended-release drug delivery device, tissue valve, tissue valve leaflet, drug-eluting stent, vascular graft, wound healing or skin graft, orthopedic prosthesis, such as bone, ligament, tendon, cartilage, and muscle.

A "scaffold" in this invention is meant to refer to a tissue matrix substantially or completely devoid of cellular materials. A scaffold may further comprise added structure porosity for cell ingrowth or proliferation.

An "acellularization process" is meant to indicate the process for removing at least a portion of cells from cellular tissue and/or tissue matrix containing connective tissue protein.

"Drug" in this invention is meant to broadly refer to a chemical molecule(s), biological molecule(s) or bioactive agent providing a therapeutic, diagnostic, or prophylactic effect in vivo. "Drug" and "bioactive agent" (interchangeable in meaning) may comprise, but not limited to, synthetic chemicals, biotechnology-derived molecules, herbs, cells, genes, growth factors, health food and/or alternate medicines. In the present invention, the terms "drug" and "bioactive agent" are used interchangeably.

It is one object of the present invention to provide an acellular biological scaffold chemically treated with a naturally occurring crosslinking agent, genipin, that is configured and adapted for tissue regeneration, and/or tissue engineering in biomedical applications. In a region with suitable substrate diffusivity, an acellular biological tissue material with added porosity and chemically treated by a crosslinking agent enables tissue regeneration, and/or tissue engineering in many biomedical applications.

Preparation and Properties of Genipin

Figure 26A:
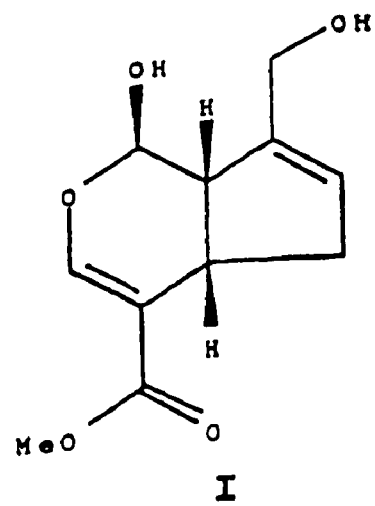
FIG. 26A is an iridoid glycoside present in fruits of Gardenia jasmindides Ellis (Structure I).
Figure 26B:
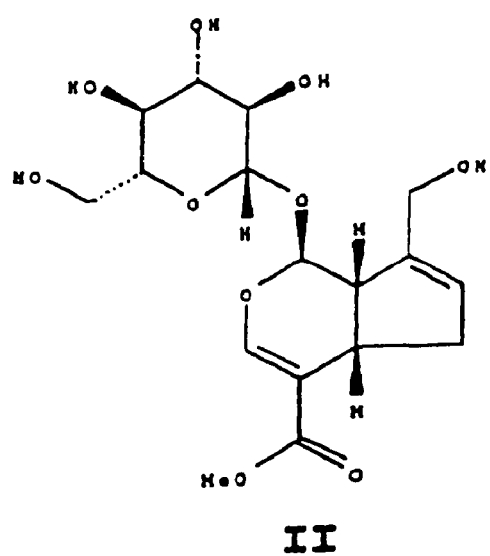
FIG. 26B is a parent compound geniposide (Structure II) from which genipin is derived.

Genipin, shown in Structure I of FIG. 26A, is an iridoid glycoside present in fruits (Gardenia jasmindides Ellis). It may be obtained from the parent compound geniposide, Structure II (FIG. 26B), which may be isolated from natural sources as described in elsewhere. Genipin, the aglycone of geniposide, may be prepared from the latter by oxidation followed by reduction and hydrolysis or by enzymatic hydrolysis. Alternatively, racemic genipin may be prepared synthetically. Although Structure I shows the natural configuration of genipin, any stereoisomer or mixture of stereoisomers of genipin as shown later may be used as a crosslinking reagent, in accordance with the present invention.

Genipin has a low acute toxicity, with $LD_{50}$ i.v. 382 mg/kg in mice. It is therefore much less toxic than glutaraldehyde and many other commonly used synthetic crosslinking reagents. As described below, genipin is shown to be an effective crosslinking agent for treatment of biological materials intended for in vivo biomedical applications, such as prostheses and other implants, wound dressings, and substitutes.

The genipin derivatives and/or genipin analog may have the following chemical formulas (Formula 1 to Formula 4):

(Genipin Analog Formula 1)

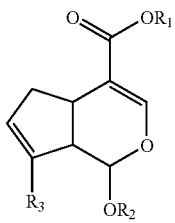

in which
$R_1$ represents lower alkyl;
$R_2$ represents lower alkyl, pyridylcarbonyl, benzyl or benzoyl;
$R_3$ represents formyl, hydroxymethyl, azidomethyl, 1-hydroxyethyl, acetyl, methyl, hydroxy, pyridylcarbonyl, cyclopropyl, aminomethyl substituted or unsubstituted by (1,3-benzodioxolan-5-yl)carbonyl or 3,4,5-trimethoxybenzoyl, 1,3-benzodioxolan-5-yl, ureidomethyl substituted or unsubstituted by 3,4,5-trimethoxyphenyl or 2-chloro-6-methyl-3-pyridyl, thiomethyl substituted or unsubstituted by acetyl or 2-acetylamino2-ethoxycarbonyethyl, oxymethyl substituted or unsubstituted by benzoyl, pyridylcarbonyl or 3,4,5-trimethoxybenzoyl;

provided that $R_3$ is not methyl formyl, hydroxymethyl, acetyl, methylaminomethyl, acetylthiomethyl, benzoyloxymethyl or pyridylcarbonyloxymethyl when $R_1$ is methyl, and its pharmaceutically acceptable salts, or stereoisomers.

(Genipin Analog Formula 2)

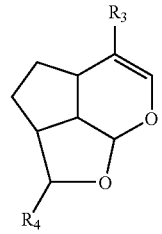

in which
$R_4$ represents lower alkoxy, benzyloxy, benzoyloxy, phenylthio, $C_1 \sim C_{12}$ alkanyloxy substituted or unsubstituted by t-butyl, phenyl, phenoxy, pyridyl or thienyl;
$R_5$ represents methoxycarbonyl, formyl, hydroxyiminomethyl, methoxyimino-methyl, hydroxymethyl, phenylthiomethyl or acetylthiomethyl;
provided that $R_5$ is not methoxycarbonyl when $R_{14}$ is acetyloxy; and
its pharmaceutically acceptable salts, or stereoisomers.

(Genipin Analog Formula 3)

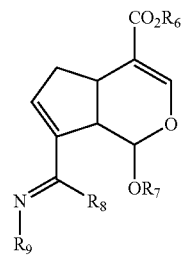

$R_6$ represents hydrogen atom, lower alkyl or alkalimetal;
$R_7$ represents lower alkyl or benzyl;
$R_8$ represents hydrogen atom or lower alkyl;
$R_9$ represents hydroxy, lower alkoxy, benzyloxy, nicotinoyloxy, isonicotinoyloxy, 2-pyridylmethoxy or hydroxycarbonylmethoxy;
provided that $R_9$ is not hydroxy or methoxy when $R_6$ is methyl and $R_8$ is hydrogen atom; and
its pharmaceutically acceptable salts, or stereoisomers.

(Genipin Analog Formula 4)

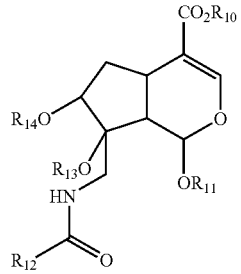

in which $R_{10}$ represents lower alkyl;

$R_{11}$ represents lower alkyl or benzyl;

$R_{12}$ represents lower alkyl, pyridyl substituted or unsubstituted by halogen, pyridylamino substituted or unsubstituted by lower alkyl or halogen, 1,3-benzodioxolanyl;

$R_{13}$ and $R_{14}$ each independently represent a hydrogen atom or join together to form isopropylidene; and its pharmaceutically acceptable salts, or stereoisomers.

Kyogoku et al. in U.S. Pat. Nos. 5,037,664, 5,270,446, and EP 0366998, entire contents of all three being incorporated herein by reference, teach the crosslinking of amino group containing compounds with genipin and the crosslinking of genipin with chitosan. They also teach the crosslinking of iridoid compounds with proteins which can be vegetable, animal (collagen, gelatin) or microbial origin. However, they do not teach loading drug onto a collagen-containing biological material or solution crosslinked with genipin as biocompatible drug carriers for drug slow-release.

Smith in U.S. Pat. No. 5,322,935, incorporated herein by reference in its entirety, teaches the crosslinking of chitosan polymers and then further crosslinking again with covalent crosslinking agents like glutaraldehyde. Smith, however, does not teach loading drug onto a chitosan-containing biological material crosslinked with genipin as biocompatible drug carriers for drug slow-release.

Previously, Chang in U.S. Pat. No. 5,929,038 discloses a method for treating hepatitis B viral infection with an iridoid compound of a general formula containing a six-member hydrocarbon ring sharing with one common bondage of a five-member hydrocarbon ring. Further, Moon et al. in U.S. Pat. No. 6,162,826 and No. 6,262,083 discloses genipin derivatives having anti hepatitis B virus activity and liver protection activity. All of which three aforementioned patents are incorporated herein by reference. The teachings of these patents do not disclose preparing tissue/device with scaffolds or collagen matrix with desirable porosity for use in tissue engineering, wherein the raw material source for tissue engineering is chemically modified by genipin, genipin derivatives or its analog with acceptably minimal cytotoxicity.

Noishiki et al. in U.S. Pat. No. 4,806,595 discloses a tissue treatment method by a crosslinking agent, polyepoxy compounds. Collagens used in that patent include an insoluble collagen, a soluble collagen, an atelocollagen prepared by removing telopeptides on the collagen molecule terminus using protease other than collagenase, a chemically modified collagen obtained by succinylation or esterification of above-described collagens, a collagen derivative such as gelatin, a polypeptide obtained by hydrolysis of collagen, and a natural collagen present in natural tissue (ureter, blood vessel, pericardium, heart valve, etc.) The Noishiki et al. patent is incorporated herein by reference. "Collagen matrix" in the present invention is collectively used referring to the above-mentioned collagens, collagen species, collagen in natural tissue, and collagen in a biological implant preform.

Voytik-Harbin et al. in U.S. Pat. No. 6,264,992 discloses submucosa as a growth substrate for cells. More particularly, the submucosa is enzymatically digested and gelled to form a shape retaining gel matrix suitable for inducing cell proliferation and growth both in vivo and in vitro. The Voytik-Harbin et al. patent is incorporated herein by reference. Collagen matrix chemically modified or treated by genipin of the present invention may serve as a shapeable raw material for making a biological implant preform adapted for inducing cell proliferation and ingrowth, but also resisting enzymatic degradation, both in vivo and in vitro.

Cook et al. in U.S. Pat. No. 6,206,931 discloses a graft prosthesis material including a purified, collagen-based matrix structure removed from a submucosa tissue source, wherein the submucosa tissue source is purified by disinfection and removal steps to deactivate and remove contaminants. The Cook et al. patent is incorporated herein by reference. Similarly, a collagen-based matrix structure, also known as "collagen matrix" in this disclosure, may serve as a biomaterial adapted for medical device use after chemical modification by genipin of the present invention.

Levene et al. in U.S. Pat. No. 6,103,255 discloses a porous polymer scaffold for tissue engineering, whereby the scaffold is characterized by a substantially continuous solid phase, having a highly interconnected bimodal distribution of open pore sizes. The Levene et al. patent is incorporated herein by reference. The present invention discloses biological scaffolds by acellular process and acidic/enzymatic treatment adapted for tissue engineering. Additional benefits of genipin tissue treatment for reduced antigenicity, reduced cytotoxicity and enhanced biodurability are disclosed in the present invention.

Bell in U.S. Pat. Nos. 6,051,750, 5,893,888, and 5,800,537 discloses method and construct for producing graft tissue from extracellular matrix, wherein the matrix particulates are seeded with living human cells or fused to constitute composites of various shape. The Bell patents are incorporated herein by reference. A collagen matrix with genipin treatment of the present invention enables a building material to constitute composites of various shapes, sizes of a medical prosthesis or biological implants.

In one embodiment, the crosslinker may further comprise epoxy compounds, dialdehyde starch, glutaraldehyde, formaldehyde, dimethyl suberimidate, carbodiimides, succinimidyls, diisocyanates, acyl azide, ultraviolet irradiation, dehydrothermal treatment, tris(hydroxymethyl)phosphine, ascorbate-copper, glucose-lysine and photo-oxidizers, and the like.

EXAMPLE 1

Tissue Specimen Preparation

In one embodiment of the present invention, bovine pericardia procured from a slaughterhouse are used as raw materials. The procured pericardia are transported to the laboratory in a cold normal saline. In the laboratory, the pericardia are first gently rinsed with fresh saline to remove excess blood on tissue. Adherent fat is then carefully trimmed from the pericardial surface. The cleaned/trimmed pericardium before acellular process is herein coded specimen-A. The procedure used to remove the cellular components from bovine pericardia is adapted from a method developed by Courtman et al (J Biomed Mater Res 1994; 28:655–66), which is also referred to herein as "an acellularization process". A portion of the trimmed pericardia is then immersed in a hypotonic tris buffer (pH 8.0) containing a protease inhibitor (phenylmethyl-sulfonyl fluoride, 0.35 mg/L) for 24 hours at 4° C. under constant stirring. Subsequently, they are immersed in a 1% solution of Triton X-100 (octylphenoxypolyethoxyethanol; Sigma Chemical, St. Louis, Mo., USA) in tris-buffered salt solution with protease inhibition for 24 hours at 4° C. under constant stirring. Samples then are thoroughly rinsed in Hanks' physiological solution and digested with DNase and RNase at 37° C. for 1 hour. This is followed by a further 24-hour extraction with Triton X-100 in tris buffer. Finally, all samples are washed for 48 hours in Hanks' solution and the acellular sample is coded specimen-B. Light microscopic examination of histological sections from extracted tissue revealed an intact connective tissue matrix with no evidence of cells.

A portion of the acellular tissue of bovine pericardia (specimen-B) is further treated with 1% acetic acid at room temperature for one hour. The acidic component is thereafter removed from the tissue by lyophilization at about −50° C. for 24 hours, followed by thorough rinse with filtered water to obtain the acellular pericardia having enlarged pore or added porosity. The tissue is stored in phosphate buffered saline (PBS, 0.01M, pH 7.4, Sigma Chemical), which tissue is coded specimen-C. The procedure of acetic acid treatment to add porosity is referred herein as "acid treatment". Similar results could be achieved by following the acid treatment with other diluted acid solution, such as nitric acid or the like, at the comparable acidity or pH vales.

The mechanism of increasing the tissue porosity treated by a mild acidic solution lies in the effect of $[H^+]$ or $[OH^-]$ values on the collagen fibers matrix of the acellular tissue. It is postulated and disclosed that acellular tissue treated with a base solution (i.e., a solution pH value greater than 7.0) could have the same effect upon enlarged pores or added porosity.

A portion of the bovine pericardia tissue post-acid treatment (i.e., specimen-C) is further treated with enzymatic collagenase as follows. Add 0.01 gram of collagenase to a beaker of 40 ml TES buffer and incubate the specimen-C pericardia tissue at 37° C. for 3 hours. The sample is further treated with 10 mM EDTA solution, followed by thorough rinse. The tissue is stored in phosphate buffered saline (PBS, 0.01M, pH 7.4, Sigma Chemical), which tissue is coded specimen-D. The procedure of collagenase treatment to add porosity is referred herein as "enzyme treatment".

EXAMPLE 2

Tissue Specimen Crosslinking

The cellular tissue (specimen-A) and acellular tissue (specimen-B) of bovine pericardia are fixed in 0.625% aqueous glutaraldehyde (Merck KGaA, Darmstadt, Germany) and are coded as specimen-A/GA and specimen-B/GA, respectively. Furthermore, the cellular tissue (specimen-A) and acellular tissue (specimen-B, specimen-C, and specimen-D) of bovine pericardia are fixed in genipin (Challenge Bioproducts, Taiwan) solution at 37° C. for 3 days and are coded as specimen-A/GP, specimen-B/GP, specimen-C/GP, and specimen-D/GP, respectively. The aqueous glutaraldehyde and genipin solutions used are buffered with PBS. The amount of solution used in each fixation was approximately 200 mL for a 10×10 cm bovine pericardium. After fixation, the thickness of each studied group is determined using a micrometer (Digimatic Micrometer MDC-25P, Mitutoyo, Tokyo, Japan). Subsequently, the fixed cellular and acellular tissue are sterilized in a graded series of ethanol solutions with a gradual increase in concentration from 20 to 75% over a period of 4 hours. Finally, the test tissue is thoroughly rinsed in sterilized PBS for approximately 1 day, with solution change several times, and prepared for tissue characterization as well as a subcutaneous study. The chemical structures of the crosslinking agents (genipin and glutaraldehyde as control) used in the study are shown in FIG. 1.

In the present invention, the terms "crosslinking", "fixation", "chemical modification", and/or "chemical treatment" for tissue or biological solution are used interchangeably.

Though the methods for removing cells from cellular tissue and/or acid treatment, base treatment, enzyme treatment to enlarge pores are well known to those who are skilled in the art, it is one object of the present invention to provide an acellular biological scaffold chemically treated with a naturally occurring crosslinking agent, genipin, that is configured and adapted for tissue regeneration, and/or tissue engineering in biomedical applications with acceptable cytotoxicity and reduced enzymatic degradation.

FIG. 2 shows photomicrographs of H&E (hematoxylin and eosin) stained tissue for (a) specimen-A, cellular tissue; (b) specimen-B, acellular tissue; (c) specimen-C, the acid treated acellular tissue; and (d) specimen-D, the enzyme treated acellular tissue. As shown in FIG. 2(a), the bovine pericardia prior to cell extraction shows a number of intact cells with identifiable cell nuclei embedded within the connective tissue matrices. In contrast, the extracted tissue revealed an intact connective tissue matrix with no evidence of cells (FIGS. 2(b)–2(d)). Some open spaces within the acellular tissue are apparent with acid treated specimen-C and enzyme treated specimen-D.

FIG. 3 shows the SEM (scanning electron microscopy) of bovine pericardia tissue for (a) specimen-A, cellular tissue; (b) specimen-B, acellular tissue; (c) specimen-C, the acid treated acellular tissue; and (d) specimen-D, the enzyme treated acellular tissue. The enzyme treated specimen-D shows several enlarged pores up to a couple of hundred microns, which would serve as a scaffold for enhanced tissue infiltration in tissue engineering.

FIG. 4 shows porosity of bovine pericardia tissue for (a) specimen-A, cellular tissue; (b) specimen-B, acellular tissue; (c) specimen-C, the acid treated acellular tissue; and (d) specimen-D, the enzyme treated acellular tissue. "Porosity" is defined as the fraction of the void over the total apparent volume. The overall porosity of the acid treated and enzyme treated acellular tissue is substantial higher than the control cellular tissue. It is suggested that a tissue scaffold of the specimen-C or specimen-D type is desirable in tissue engineering applications for tissue infiltration or cells ingrowth.

EXAMPLE 3

Comparison of Glutaraldehyde and Genipin Crosslinking

Figure 5:
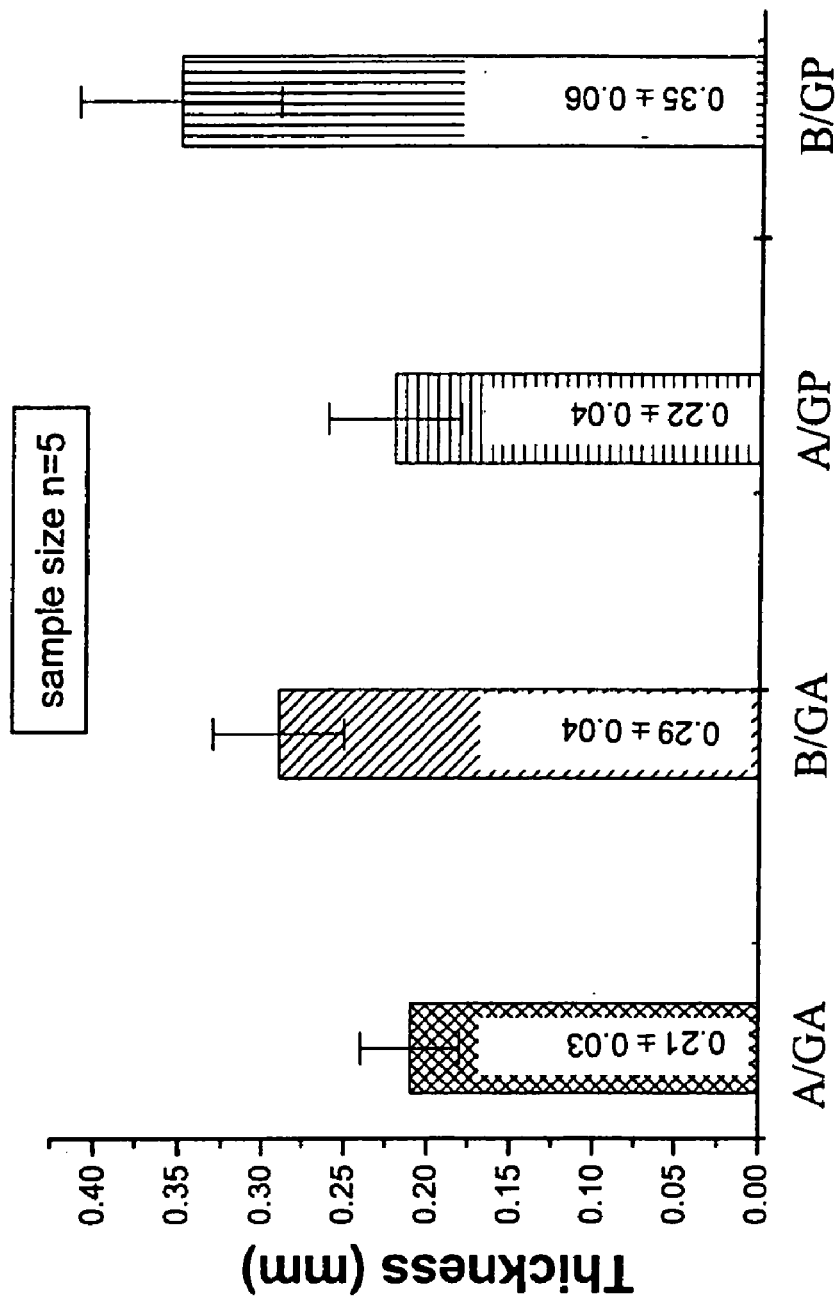
FIG. 5 shows thickness of the glutaraldehyde-fixed cellular tissue (A/GA), the glutaraldehyde-fixed acellular tissue (B/GA), the genipin-fixed cellular tissue (A/GP), and the genipin-fixed acellular tissue (B/GP) before implantation.

Pericardia tissue chemically treated with glutaraldehyde and genipin shows different characteristics and biocompatibility. FIG. 5 shows thickness of the glutaraldehyde-fixed cellular tissue (A/GA), the glutaraldehyde-fixed acellular tissue (B/GA), the genipin-fixed cellular tissue (A/GP), and the genipin-fixed acellular tissue (B/GP) before implantation. In general, the acellular tissue shows increased tissue thickness by either type of crosslinking (with glutaraldehyde or genipin) as compared to the control cellular tissue. It is further noticed that genipin-fixed acellular tissue shows the highest tissue thickness among the samples characterized, probably due to enhanced water absorption. This high tissue thickness of genipin-fixed acellular tissue is desirable for tissue engineering in vivo or in vitro in medical devices, such as an extended-release drug delivery device, vascular or skin graft, or orthopedic prosthesis of bone, ligament, tendon, and cartilage.

Figure 6:
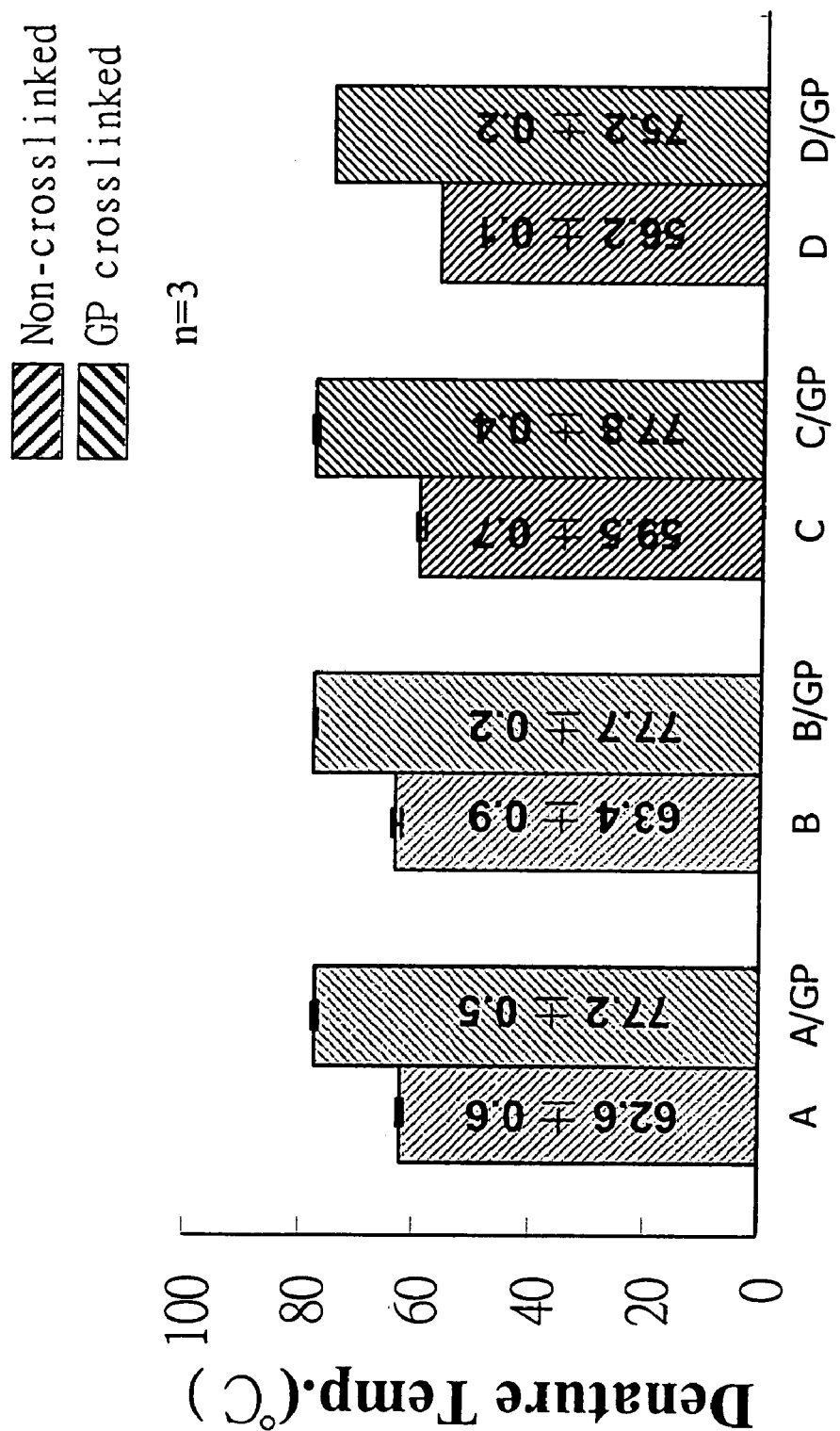
FIG. 6 show denaturation temperature values of the non-crosslinked and genipin-crosslinked bovine pericardia tissue for (a) specimen-A, cellular tissue; (b) specimen-B, acellular tissue; (c) specimen-C, the acid treated acellular tissue; and (d) specimen-D, the enzyme treated acellular tissue.

To characterize the degree of tissue crosslinking, denature temperatures are measured on the non-crosslinked and genipin-crosslinked bovine pericardia tissue for (a) specimen-A, cellular tissue; (b) specimen-B, acellular tissue; (c) specimen-C, the acid treated acellular tissue; and (d) specimen-D, the enzyme treated acellular tissue (FIG. 6). The denaturation temperatures of specimens of each studied group before implantation and those retrieved at distinct duration postoperatively are measured in a Perkin Elmer differential scanning calorimeter (Model DSC-7, Norwalk, Conn., USA). This technique was widely used in studying the thermal transitions of collagenous tissues. Details of the methodology used in the denaturation temperature measurement were described elsewhere (J Biomed Mater Res 1998; 42:560–567). As shown in FIG. 6, the denature temperatures in all four types of genipin (GP) crosslinked pericardia tissue are higher as expected than their control non-crosslinked counterparts.

Figure 7:
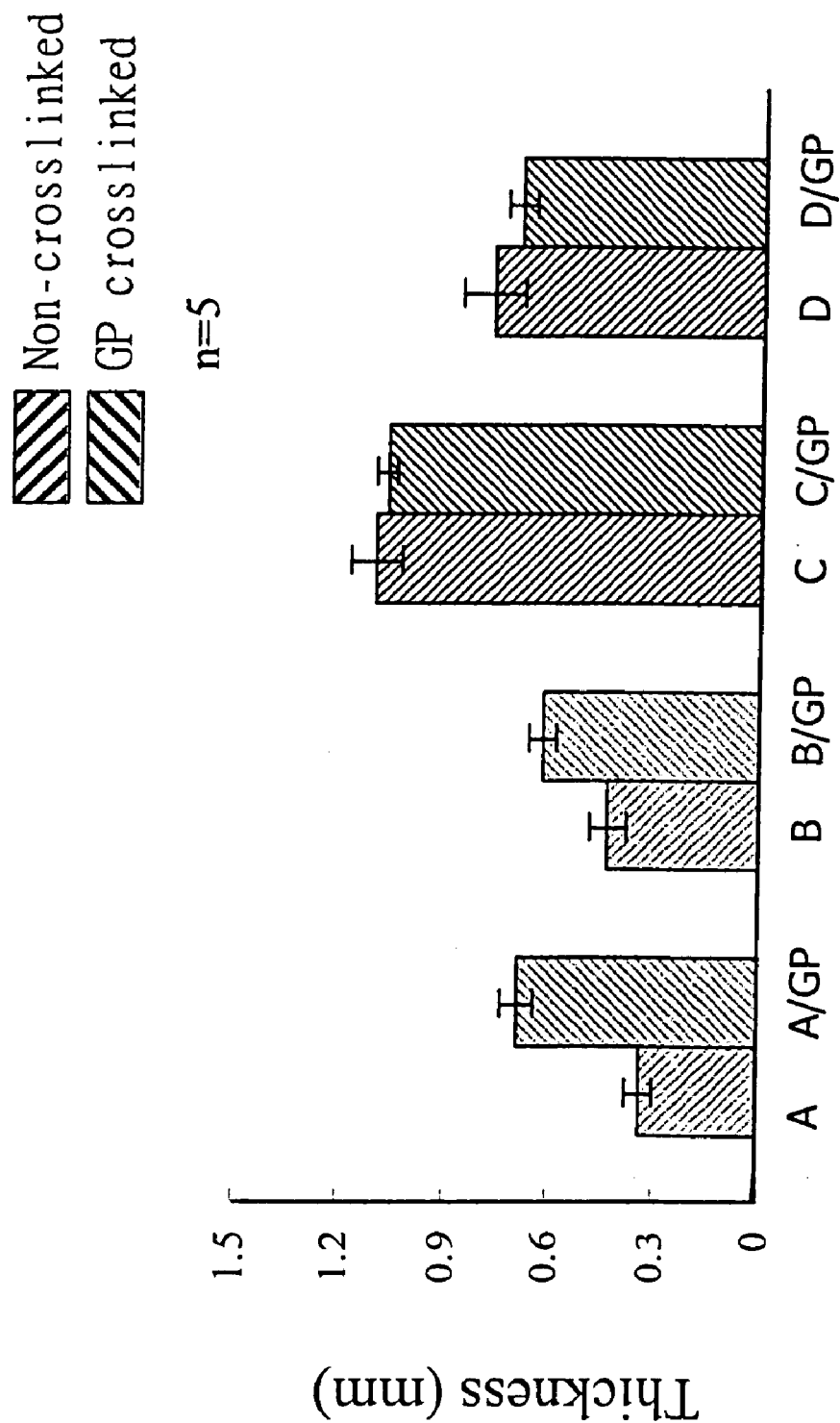
FIG. 7 shows thickness of the bovine pericardia tissue before and after genipin crosslinking for (a) specimen-A, cellular tissue; (b) specimen-B, acellular tissue; (c) specimen-C, the acid treated acellular tissue; and (d) specimen-D, the enzyme treated acellular tissue.

FIG. 7 shows thickness of the bovine pericardia tissue before and after genipin crosslinking for (a) specimen-A, cellular tissue; (b) specimen-B, acellular tissue; (c) specimen-C, the acid treated acellular tissue; and (d) specimen-D, the enzyme treated acellular tissue. For example, a genipin-crosslinked specimen-A is designated as specimen-A/GP, and so forth. It is suggested that thicker tissue is normally due to higher water content or water absorption capability. It implies that the loose extracellular space temporarily occupied by water in acid treated pericardia tissue (in either non-crosslinked tissue or genipin crosslinked tissue) would be desirable for tissue engineering applications in an extended-release drug delivery device, vascular or skin graft, or orthopedic prosthesis, such as bone, ligament, tendon, cartilage, and muscle. The biological tissue material with added porosity may comprise steps of removing cellular material from a natural tissue and crosslinking the natural tissue with a crosslinking agent, wherein the natural tissue is selected from a group consisting of a porcine valve, a bovine jugular vein, a bovine pericardium, an equine pericardium, a porcine pericardium, and submucosal tissue.

EXAMPLE 4

Animal Implant Study

The cellular and acellular tissue fixed with glutaraldehyde and genipin from Example 2 were implanted subcutaneously in a growing rat model (4-week-old male Wistar) under aseptic conditions. Each test sample was approximately 1 cm by 2 cm coupon. In a first study, genipin-crosslinked tissue for specimen-A/GP, specimen-B/GP, specimen-C/GP, and specimen-D/GP are implanted. FIG. 8 shows photomicrographs of H&E stained genipin-crosslinked tissue for (a) specimen-A/GP, cellular tissue; (b) specimen-B/GP, acellular tissue; (c) specimen-C/GP, the acid treated acellular tissue; and (d) specimen-D/GP, the enzyme treated acellular tissue: all retrieved at 3-day postoperatively. It is apparent that cells infiltration into the enlarged pores of the enzyme treated specimen-D/GP is quite visible and evident. The samples used for light microscopy were fixed in 10% phosphate buffered formalin for at least 3 days and prepared for histological examination. In the histological examination, the fixed samples were embedded in paraffin and sectioned into a thickness of 5 μm and then stained with hematoxylin and eosin (H&E). The stained sections of each test sample then are examined using light microscopy (Nikon Microphoto-FXA) for tissue inflammatory reaction and photographed with a 100 ASA Kodachrome film.

Figure 9:
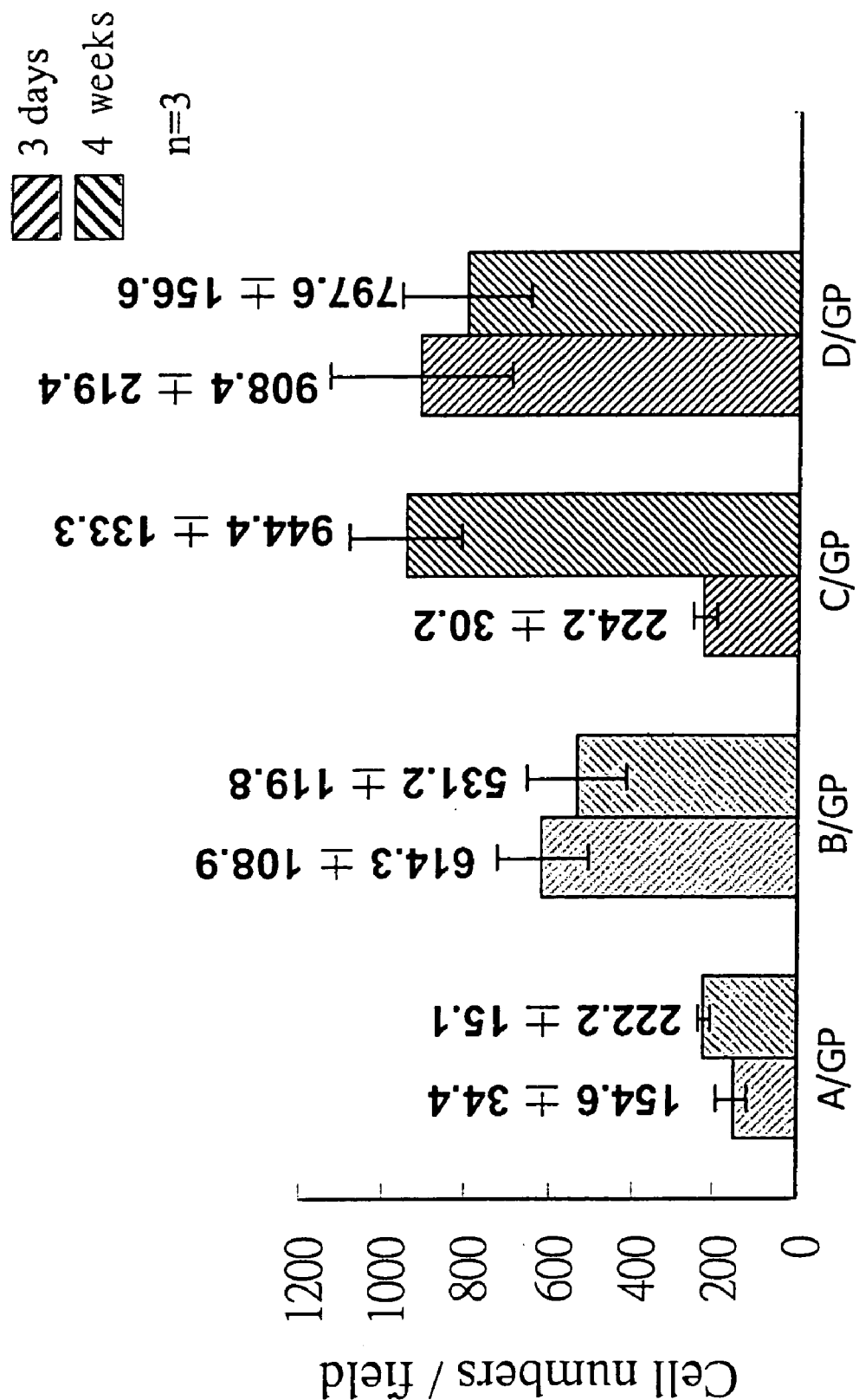
FIG. 9 are cells infiltration extents of genipin-crosslinked bovine pericardia tissue for (a) specimen-A/GP, cellular tissue; (b) specimen-B/GP, acellular tissue, (c) specimen-C/GP, the acid treated acellular tissue; and (d) specimen-D/GP, the enzyme treated acellular tissue retrieved at 3 days and 4-week postoperatively.

In the first study, genipin-crosslinked tissue for (a) specimen-A/GP, cellular tissue; (b) specimen-B/GP, acellular tissue; (c) specimen-C/GP, the acid treated acellular tissue; and (d) specimen-D/GP, the enzyme treated acellular tissue are retrieved at 3-day and 4 weeks postoperatively. The cell numbers per field (on a reference basis) are counted and shown in FIG. 9. At 4 weeks implantation, both specimen-C/GP and specimen-D/GP show significant higher cells infiltration than the tissue samples without enlarged pores (i.e., specimen-A/GP or specimen-B/GP).

A second study is conducted for comparing the effect of glutaraldehyde (GA)-fixed and genipin (GP)-fixed tissue samples on their ultimate tensile strength. The implanted test samples then were retrieved at 3-day, 1-week, 4-week, 12-week, 24-week, and 52-week postoperatively. At retrieval, the appearance of each retrieved sample first was grossly examined and photographed. The samples were then processed for light microscopy or tensile strength measurement.

The tensile strength values of specimens of each studied group before implantation and those retrieved at distinct implantation duration were determined by uniaxial measurements using an Instron material testing machine (Mini 44, Canton, Mass., USA) at a constant speed of 10 mm/min.

Figure 10:
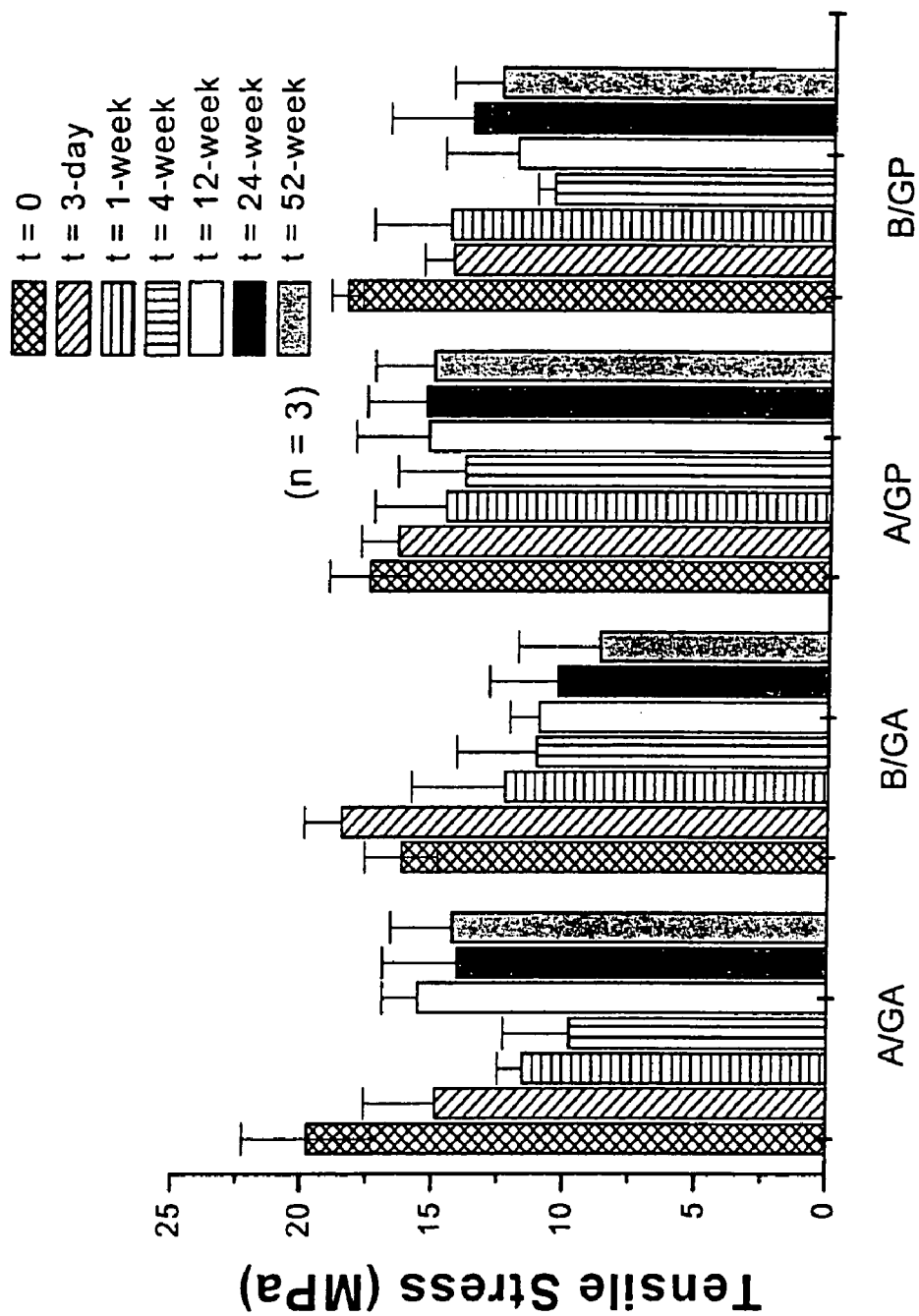
FIG. 10 are tensile-strength values of the glutaraldehyde-fixed cellular tissue (A/GA), the glutaraldehyde-fixed acellular tissue (B/GA), the genipin-fixed cellular tissue (A/GP), and the genipin-fixed acellular tissue (B/GP) before implantation and those retrieved at several distinct duration of post implantation.

As shown in FIG. 10, the tensile strength values of all test samples before implantation were comparable ($P>0.05$). It is found that the tensile-strength values of all test samples declined significantly with increasing the duration of implantation prior to 4-week postoperatively ($P<0.05$). However, with the exception of the glutaraldehyde-fixed acellular tissue, the tensile strength values of all other test samples increased steadily afterwards ($P<0.05$).

EXAMPLE 5

Gelatin Crosslinking Experiment

3-D Scaffold: Gelatin (0.8 g) dissolved in 7 mL phosphate buffered saline was crosslinked by 3 mL 1% genipin or 0.167% glutaraldehyde for 9 hours. The crosslinked gelatin was dried in an oven (37□) for 1 hour and then frozen at −30□ for 9 hours. Finally, the frozen gelatin was lyophilized to create a 3-D scaffold. This represents one type of the "collagen matrix" as defined in the present invention.

In the cell culture study, 16-mm-diameter test samples cut from the sterilized glutaraldehyde-fixed or genipin-fixed tissue were glued to the bottoms of the wells in a 24-well plate (the diameter of each well is about 16 mm) using a sterilized collagen solution. Subsequently, human fibroblasts (HFW) at $5\times10^4$ cells/well were seeded evenly on the surface of each test sample in DMEM with 10% FCS. The test samples in the wells then were removed at 3-day through 1-month after cell seeding. During this period, the growth medium was changed routinely. After cell culture, the test scaffolds were washed with phosphate buffered saline (PBS) twice and surviving cell numbers were determined by the MTT assay (J Biomater Sci Polymer Edn 1999; 10:63–78).

As disclosed in a co-pending provisional application Ser. No. 60/314,195 filed Aug. 22, 2001 entitled CHEMICAL MODIFICATION OF ACELLULAR BIOMEDICAL MATERIAL WITH GENIPIN, entire contents of which are incorporated herein by reference, the structure of the genipin-fixed scaffold remained intact throughout the entire course of the experiment (up to 1-month after cell culture), while that of the glutaraldehyde-fixed scaffold was found collapsed in the culture medium at 7-day after cell seeding. The human fibroblasts cultured in the genipin-crosslinked scaffold were significantly greater than the glutaraldehyde-crosslinked scaffold throughout the entire course of the experiment as observed in the MTT assay. This indicates that the cellular compatibility of the genipin-crosslinked scaffold is superior to that of the glutaraldehyde-crosslinked scaffold.

The experiment presents the cellular compatibility of a 3-D porous scaffold made from gelatin chemically modified or crosslinked by genipin. The glutaraldehyde-fixed counterpart was used as control. The results obtained indicate that the genipin-crosslinked scaffold had a better cellular compatibility than its glutaraldehyde-fixed counterpart. Additionally, the glutaraldehyde-crosslinked scaffold was found collapsed by 7-day after cell culture, while the genipin-crosslinked scaffold remained intact up to 1-month after cell culture. It is hereby disclosed that the genipin-fixed porous scaffold when configured and adapted for tissue regeneration or tissue engineering comprising steps of removing cellular material from a natural tissue and crosslinking the natural tissue with genipin is desirable, wherein the 3-D scaffold is characterized by reduced antigenicity, reduced immunogenicity and reduced enzymatic degradation upon placement inside a patient's body. The porosity of the scaffold tissue is increased at least 5% over that of the nature tissue adapted for promoting tissue regeneration or tissue engineering.

As disclosed and outlined in the co-pending provisional application Ser. No. 60/314,195 by the present inventors, the degrees in inflammatory reaction in the animal studies for the genipin-fixed cellular and acellular tissue were significantly less than their glutaraldehyde-fixed counterparts. Additionally, it was noted that the inflammatory reactions for the glutaraldehyde-fixed cellular and acellular tissue lasted significantly longer than their genipin-fixed counterparts. These findings indicated that the biocompatibility of the genipin-fixed cellular and acellular tissue is superior to the glutaraldehyde-fixed cellular and acellular tissue. It is hypothesized that the lower inflammatory reactions observed for the genipin-fixed cellular and acellular tissue may be due to the lower cytotoxicity of their remaining residues, as compared to the glutaraldehyde-fixed counterparts. In our previous study, it was found that genipin is significantly less cytotoxic than glutaraldehyde (J Biomater Sci Polymer Edn 1999; 10:63–78). The cytotoxicity observed for the glutaraldehyde-fixed cellular and acellular tissue seems to result from a slow leaching out of unreacted glutaraldehyde as well as the reversibility of glutaraldehyde-crosslinking. It was observed that when concentrations above 0.05% glutaraldehyde were used to crosslink materials, a persistent foreign-body reaction occurred (J Biomater Sci Polymer Edn 1999; 10:63–78).

In the study (co-pending provisional application Ser. No. 60/314,195), it was found that the inflammatory cells were mostly surrounding the cellular tissue, while they were able to infiltrate into the outer layers of the acellular tissue for both the glutaraldehyde-fixed and genipin-fixed groups. As aforementioned, as compared to the cellular tissue, the acellular tissue formed a decreased density of the structural fiber components due to the increase in their thickness (FIG. 5). In addition, after cell extraction, it left more open spaces in the acellular tissue (FIG. 4). As a result, the inflammatory cells were able to infiltrate into the acellular tissue. This significantly increases the contact area between the host immune system (the inflammatory cells) and the foreign material (the acellular-tissue matrix). Consequently, the degrees in inflammatory reaction for the acellular tissue were consistently grater than the cellular tissue.

Figure 11:
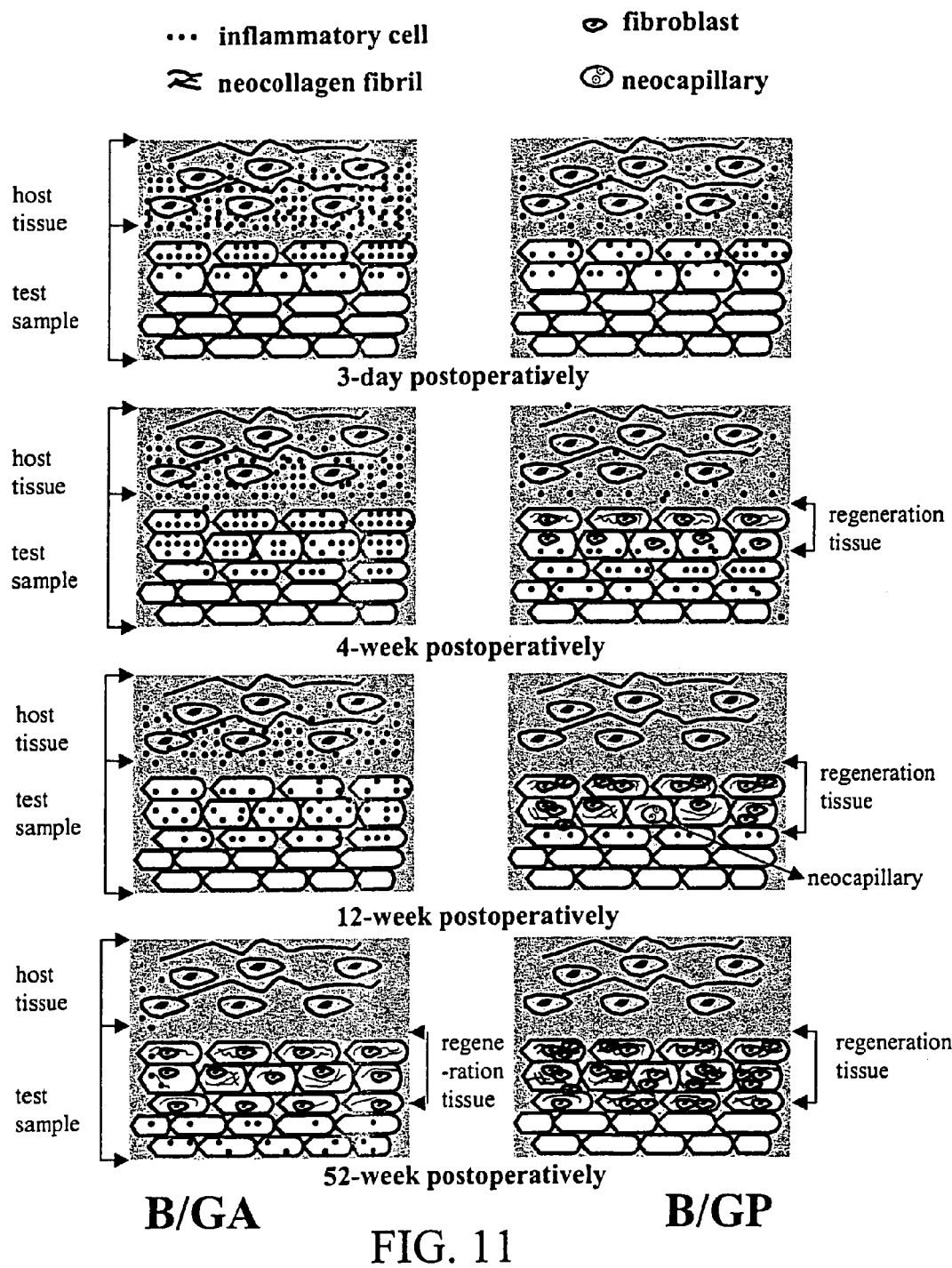
FIG. 11 is an illustration of the suggested mechanism of tissue regeneration in the outer layers of the acellular tissue as disclosed in the present invention wherein B/GA denotes the glutaraldehyde-fixed acellular tissue and B/GP denotes the genipin-fixed acellular tissue.

As the cells were able to infiltrate into the outer layers of the acellular tissue, tissue regeneration from the host was observed in this area. FIG. 11 illustrates a suggested mechanism of tissue regeneration in the outer layers of the acellular tissue as per the findings disclosed in the present invention and co-pending provisional application Ser. No. 60/314,195. Once the inflammatory cells infiltrated into the acellular tissue matrix, the enzymes (collagenase and other proteases) secreted by macrophages might start to degrade the fibrous proteins. This allowed fibroblasts from the host tissue (rat's tissue in one example) to migrate into the outer layer of the acellular tissue and to secrete neocollagen fibrils. As duration of implantation progresses, angiogenesis (neocapillaries) occurs. Thus more fibroblasts from the host tissue migrate into the acellular tissue matrix and therefore more neocollagen fibrils are produced. As a result, the most outer layers of the glutaraldehyde-fixed and genipin-fixed acellular tissue observed at 52-week postoperatively were the new tissue regenerated from the host. The tissue regeneration rate observed in the outer layer of the genipin-fixed acellular tissue matrix was significantly faster than its glutaraldehyde-fixed counterpart (FIG. 11).

In conclusion, the results as disclosed in the present invention indicate that the degrees in inflammatory reaction for the genipin-fixed cellular and acellular tissue are significantly less than their glutaraldehyde-fixed counterparts. The acellular tissue provides a natural microenvironment for cell migration to regenerate tissue. The tissue regeneration rate for the genipin-fixed acellular tissue is significantly faster than its glutaraldehyde-fixed counterpart. And this faster tissue regeneration enables a genipin-fixed acellular tissue suitable as a biological scaffold configured and adapted for tissue regeneration or tissue engineering, wherein the scaffold is characterized by reduced antigenicity, reduced immunogenicity and reduced enzymatic degradation upon placement inside a patient's body.

It is hereby disclosed that a method of preparing a biological scaffold configured and adapted for tissue regeneration or tissue engineering comprises steps of removing cellular material from a natural tissue or collagen matrix; and chemically modifying the acellular tissue or collagen matrix with genipin. As defined, "genipin" in this invention is meant to refer to the naturally occurring compound as shown in FIG. 1 and its derivatives, analog, stereoisomers and mixtures thereof. The biological scaffold of the present invention may be characterized by reduced antigenicity, reduced immunogenicity and reduced enzymatic degradation upon placement inside a patient's body. The collagen matrix of the present invention may be selected from a group consisting of an insoluble collagen, a soluble collagen, an atelocollagen prepared by removing telopeptides on the collagen molecule terminus using protease other than collagenase, a chemically modified collagen obtained by succinylation or esterification of above-described collagens, a collagen derivative such as gelatin, a polypeptide obtained by hydrolysis of collagen, and a natural collagen present in natural tissue (ureter, blood vessel, pericardium, heart valve, etc.).

It is further disclosed that a biological scaffold for cells seeding, cell growth or cell proliferation may comprise a natural tissue devoid of cellular material and chemically modified by genipin. As indicated in FIG. 4, the porosity increase of the acellular specimen-B is 7.6% higher than its control cellular specimen-A. Furthermore, the porosity increase of the acid treated acellular tissue specimen-C and the porosity increase of the enzyme treated acellular tissue specimen-D are 53% and 61%, respectively higher than the porosity of the control cellular specimen-A. The biological scaffold may be characterized by an increase of the biological scaffold volume after treatment by at least 5%, preferably more than 10% of volume porosity change (FIG. 4). The "treatment" to make a biological tissue material or scaffold of the present invention may include the acellularization process, acid treatment, base treatment, and/or enzyme (e.g. protease) treatment processes. The biological tissue material is selected from a group consisting of a tissue valve, a tissue valve leaflet, a vascular graft, a ureter, a urinary bladder, pericardium, and a dermal graft.

It is another embodiment of the present invention to provide a tendon or ligament graft for use as connective tissue substitute, the graft being formed from a segment of connective tissue protein, wherein the segment is crosslinked with genipin, its analog or derivatives. The connective tissue protein may be collagen or pericardia patches that is substantially devoid of cells and porosity of the tissue graft is increased at least 5% adapted for promoting autogenous ingrowth into the graft. The process for using a tissue sheet to make a tendon or ligament graft has been disclosed by Badylak et al. in U.S. Pat. Nos. 5,573,784, 5,445,833, Nos. 5,372,821, 5,281,422, and so forth, the entire contents of which are incorporated herein by reference, which disclose a method for promoting the healing and/or regrowth of diseased or damaged tissue structures by surgically repairing such structures with a tissue graft construct prepared from a segment of intestinal submucosal tissue.

Further, Badylak et al. in U.S. Pat. No. 6,485,723, the entire contents of which are incorporated herein by reference, discloses an improved tissue graft construct comprising vertebrate submucosa delaminated from both the external smooth muscle layers and the luminal portions of the tunica mucosa and added primary cells, wherein the vertebrate submucosa comprises tunica submucosa delaminated from both the tunica muscularis and at least the luminal portion of the tunica mucosa of vertebrate intestinal tissue. With added porosity, it is herein provided a biological tissue material derived from submucosal tissue adapted for promoting tissue regeneration.

Myocardial Tissue Regeneration

The current material for myocardial artery includes Dacron polyester fabric, expanded polytetrafluoroethylene (e-PTFE), glutaraldehyde-treated bovine pericardium, antibiotic preserved or cryopreserved homografts. Material related failures include no cell growth, not viable, no pulsatile flow, being treated as a foreign body, thrombogenic nature, and infectable. The animal model (shown in FIG. 14) is a transmural defect surgically created in the right ventricle of an adult rat. The test specimen is an acellular tissue patch fixed with genipin at about 60% crosslinkage and the control is e-PTFE patch. Each specimen is 0.7 cm in width and 0.7 cm in height. The implant specimens are retrieved postoperatively at 4 weeks (sample size=5) and one month.

Figure 14:
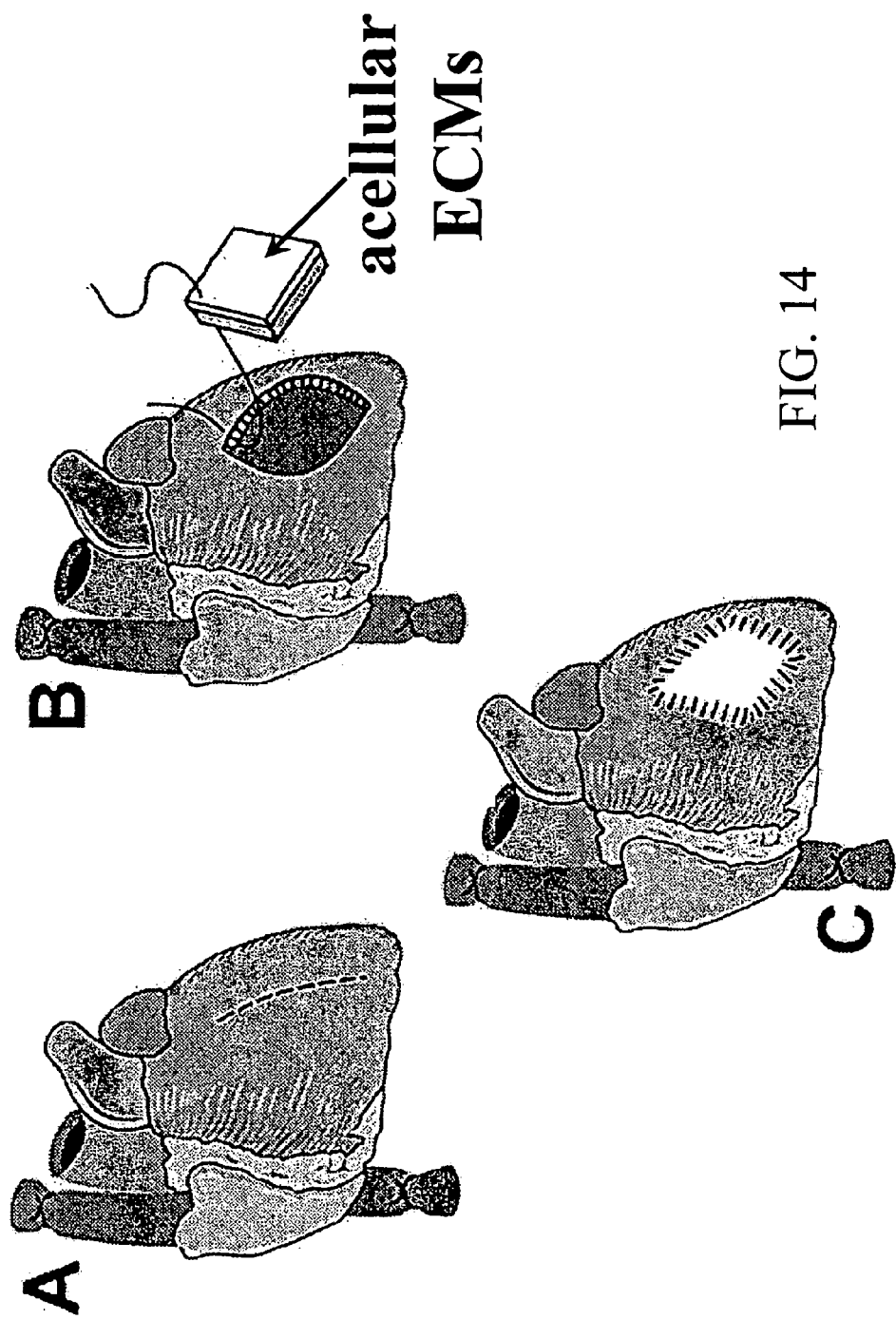
FIG. 14 is an animal myocardial patch study design for myocardial tissue regeneration.

FIG. 15 shows 4-week postoperative results on animal myocardial patch study of FIG. 14: photomicrographs of Masson Trichrome stained explant while FIG. 16 shows photomicrographs of Factor VIII stained explant. The middle layer of the 60% crosslinkage acellular tissue patch fixed with genipin is abundantly filled with neo-muscle fibers and neo-collagen fibrils as evidenced by Masson Trichrome stain. The blood-contacting tissue surface for the 60% crosslinkage acellular tissue patch fixed with genipin is filled with contagious endothelial cells while the control e-PTFE implant is with sparse endothelialization. It is concluded that acellular biological tissue fixed with genipin is a promising tissue-engineering extracellular matrix for repairing myocardial defect.

Angiogenesis Factor

U.S. Pat. No. 6,506,398 issued to Tu (a co-inventor of the present invention), the entire contents of which are incorporated herein by reference, discloses a vascular graft comprising Vascular Endothelial Growth Factor (VEGF) and/or Platelet Derived Growth Factor (PDGF) for enhanced site-specific angiogenesis and methods thereof. At least one VEGF, PDGF or angiogenesis factor is incorporated into the vascular graft to facilitate enhanced angiogenesis so as the cells are stimulated to migrate to environments having higher concentration of growth factors and start mitosis. With added porosity, it is provided a biological tissue material with loaded growth factors adapted for promoting tissue regeneration, wherein the growth factor is selected from the group consisting of VEGF, VEGF 2, bFGF, VEGF121, VEGF165, VEGF189, VEGF206, PDGF, PDAF, TGF-β, PDEGF, PDWHF, and combination thereof.

Vascular endothelial growth factor (VEGF) is mitogenic for vascular endothelial cells and consequently is useful in promoting neovascularization (angiogenesis) and reendothelialization. Angiogenesis means the growth of new capillary blood vessels. Angiogenesis is a multi-step process involving capillary endothelial cell proliferation, migration and tissue penetration. VEGF is a growth factor having a cell-specific mitogenic activity. It would be desirable to employ a wound healing substrate incorporating a mitogenic factor having mitogenic activity that is highly specific for vascular endothelial cells following vascular graft surgery, balloon angioplasty or to promote collateral circulation. U.S. Pat. No. 5,194,596 discloses a method for producing VEGF while U.S. Pat. No. 6,040,157 discloses a specific VEGF-2 polypeptide. Both patents are incorporated herein by reference.

Gordinier et al. in U.S. Pat. No. 5,599,558 discloses a method of making a platelet releasate product and methods of treating tissues with the platelet releasate. Platelet derived growth factor (PDGF) is a well-characterized dimeric glycoprotein with mitogenic and chemoattractant activity for fibroblasts, smooth muscle cells and glial cells. In the presence of PDGF, fibroblasts move into the area of tissue needing repair and are stimulated to divide in the lesion space itself. It has been reported that the cells exposed to lower PDGF concentrations are stimulated to move to environments having higher concentrations of PDGF and divide. The patent is incorporated hereby by reference.

In some aspects, there is provided a method for promoting autogenous ingrowth of a biological tissue material comprising the steps of providing a natural tissue, removing cellular material from the natural tissue, increasing porosity of the natural tissue by at least 5%, loading an angiogenesis agent or autologous cells into the porosity, and crosslinking the natural tissue with a crosslinking agent. In one preferred embodiment, the angiogenesis agent is an organic angiogenesis factor (for example, ginsenoside $Rg_1$, ginsenoside Re) or a protein angiogenesis factor selected from the group consisting of VEGF (vascular endothelial growth factor), VEGF 2, bFGF (basic fibroblast growth factor), VEGF121, VEGF165, VEGF189, VEGF206, PDGF (platelet-derived endothelial cell growth factor), PDAF, TGF-β (transforming growth factor-beta), TGF-α (transforming growth factor-alpha), PDEGF, PDWHF, and combination thereof. In another embodiment, the protein angiogenesis factor may further comprise, but not limited to, a fibroblast growth factor, an epidermal growth factor, an endothelial cell growth factor, an insulin-like growth factor, a periodontal ligament cell, aFGF (acidic fibroblast growth factor), and human growth factor (HGF).

In an alternate embodiment, there is provided a method for inhibiting autogenous ingrowth of a biological tissue material comprising the steps of providing a natural tissue, removing cellular material from the natural tissue, increasing porosity of the natural tissue by at least 5%, loading an anti-angiogenesis agent into the porosity, and crosslinking the natural tissue with a crosslinking agent. The anti-angiogenesis factor or angiogenesis inhibitors may include, for example, collagenase inhibitors; minocycline; medroxyprogesterone; chitin chemically modified with 6-O-sulfate and 6-O-carboxymethyl groups; angiostatic steroids, such as tetrahydrocortisol; and heparin, including fragments of heparin, such as, for example, fragments having a molecular weight of about 6,000, admixed with steroids, such as, for example, cortisone or hydrocortisone; angiogenesis inhibitors, including angioinhibin (AGM-1470—an angiostatic antibiotic); platelet factor 4; protamine; sulfated polysaccharide peptidoglycan complexes derived from the bacterial wall of an Arthobacter species; fungal-derived angiogenesis inhibitors, such as fumagillin derived from *Aspergillus fumigatus*; D-penicillamine; gold thiomalate; thrombospondin; vitamin D3 analogues, including, for example, 1-α-25-dihydroxyvitamin D3 and a synthetic analog, 22-oxa-1-α, 25-dihydroxyvitamin D3; α-interferon; cytokines, such as the interleukins, including, for example, interleukin-I (IL-1), interleukin-2 (IL-2), and interleukin-8 (IL-8) granulocyte macrophage colony stimulating factor (GMCSF); heparin, including low molecular weight fragments of heparin or analogues of heparin; simple sulfated polysaccharides, such as cyclodextrins, including α-, β- and γ-cyclodextrin; tetradecasulfate; transferrin; ferritin; platelet factor 4; protamine; Gly-His-Lys complexed to copper, ceruloplasmin; (12R)-hydroxyeicosatrienoic acid; okadaic acid; lectins; antibodies; Cd11a/CD18; and Very Late Acting Integrin-4 (VLA-4).

Figure 17:
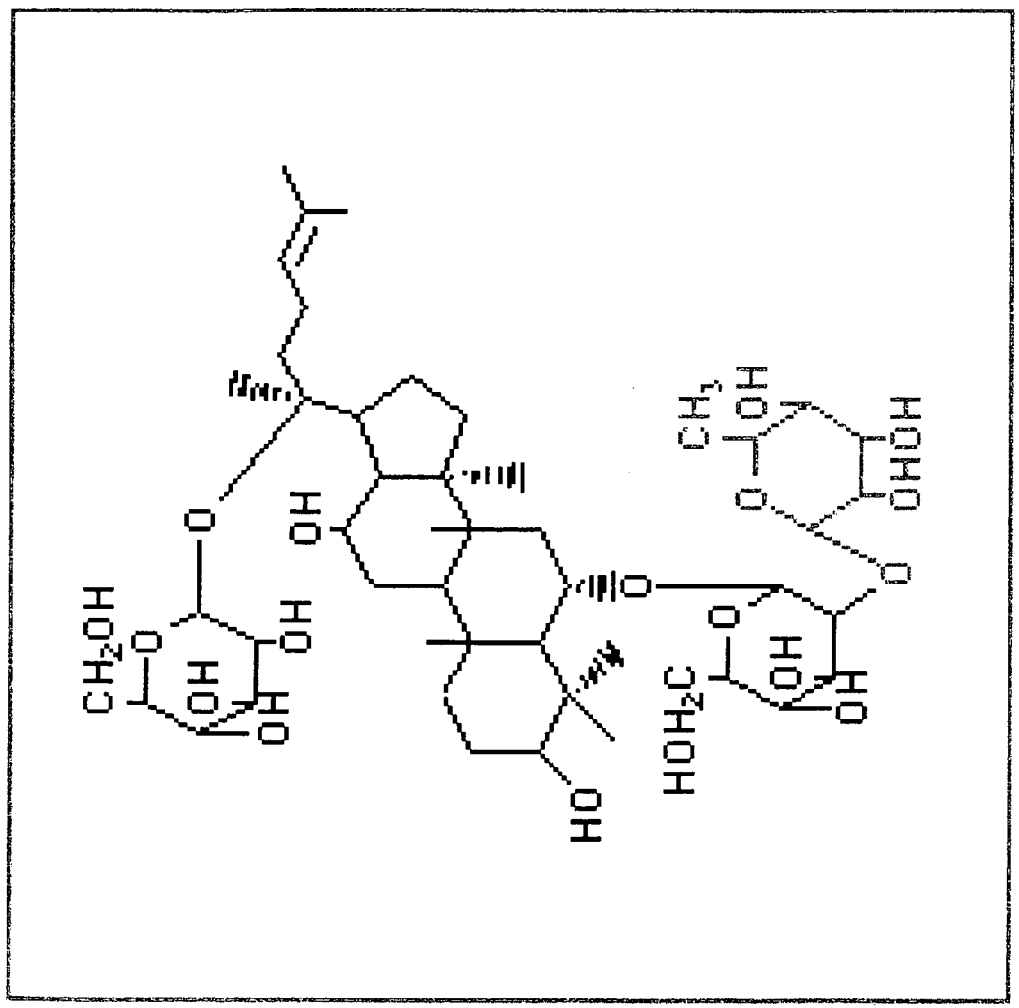
FIG. 17 is a chemical formula for Ginsenoside Re.

It is known that protein type growth factors have relatively short shelf life. For medical device use, it is one object of the invention to provide an organic compound, non-protein type growth factors, such as ginsenoside $Rg_1$ (as shown in FIG. 12) and/or ginsenoside Re (as shown in FIG. 17).

Ginseng is one of the most widely used herbal drugs and is reported to have a wide range of therapeutic and pharmacological activities. The two major species of commerce are *Panax ginseng* C. A. Meyer (Asian ginseng), and *Panax quinquefolius* L. (North American ginseng). Both species contain active ginsenoside saponins, but there are significant differences in their identity and distribution. It has been observed that over thirty ginsenosides have been identified from *Panax* spp., however six of these, $Rg_1$, Re, $Rb_1$, Rc, $Rb_2$, and Rd constitute the major ginsenosides accounting for over 90% of the saponin content of ginseng root. Standard ginsenosides $Rg_1$, Re, $Rb_1$, Rc, $Rb_2$ and Rd can be isolated and characterized by NMR. In contrary to general angiogenesis effects of ginsenoside $Rg_1$ and Re, ginsenoside $Rg_3$ can block angiogenesis and inhibit tumor growth and metastasis by downregulating the expression of VEGF mRNA and protein and reducing microvascular density. Some aspects of the invention relate to a method of reducing angiogenesis for treating tissue comprising: providing crosslinkable biological solution to the target tissue, wherein the crosslinkable biological solution is loaded with at least one anti-angiogenic agent (also known as angiogenic antagonist or inhibitor) such as ginsenoside $Rg_3$ and the like.

Duckett et al. in U.S. Pat. No. 6,340,480, the entire contents of which are incorporated herein by reference, discloses a composition for promoting circulation, comprising an effective amount of L-arginine, ginseng and Ziyphi fructus, the constituents being administered to stimulate release of NO in the body. Some past studies with natural ingredients have shown that with natural medicines include ginseng, ginsenoside, and its purified derivative $Rg_1$ (also known as RG-1) have a tendency to increase synthesis of NO levels. It has been shown that $Rg_1$ enhances the production of NO for killing certain tumor cells. See, e.g., Fan et al., Enhancement of Nitric Oxide Production from Activated Macrophages by a Purified Form of Ginsenoside ($Rg_1$), American Journal of Chinese Medicine, Vol. XXIII, Nos. 3–4. pp. 279–287 (1995 Institute for Advanced Research in Asian Science and Medicine).

Figure 12:
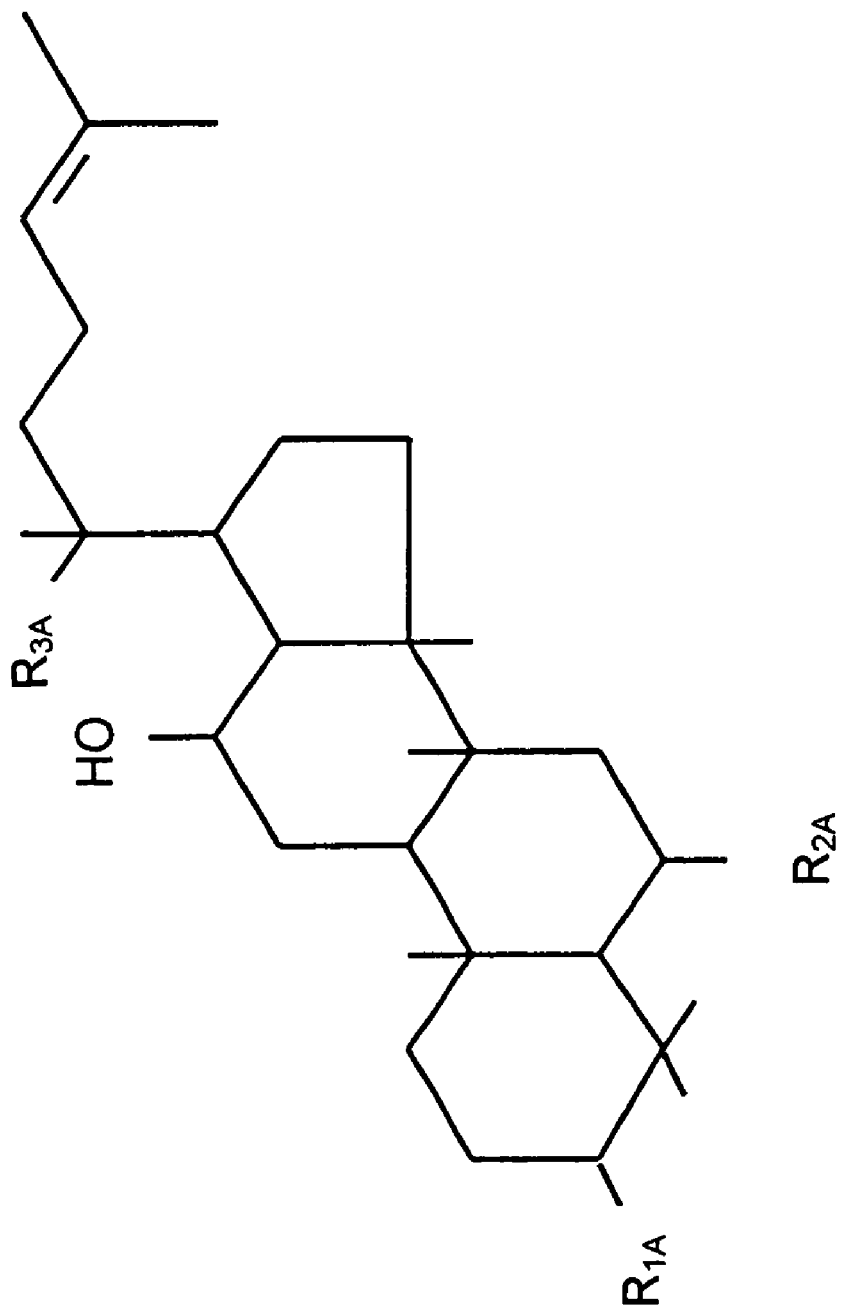
FIG. 12 is a chemical formula of ginsenoside $Rg_1$.

FIG. 12 shows a chemical formula of ginsenoside $Rg_1$, one of the principal active components of ginseng saponins which is isolated from the roots of Panax ginseng. In one embodiment as shown in FIG. 12, in which $R_{1A}$=OH or O-Glc, $R_{2A}$=H or O-Glc, $R_{3A}$=O-Glc, wherein Glc designates a β-D glucopyranosyl group. $Rg_1$ is believed to stimulate vascular endothelial cells proliferation, and tube formation in a patient. Ginseng's therapeutic uses were recorded in the oldest Chinese pharmacopeia, Shen Nong Ben Cao Jing, written about two thousand years ago. Ginseng action is non-local and non-specific. In Asian medicine, ginseng is used as a tonic to revitalize the function of organism as a whole and replenish vital energy ("chi"). It is traditionally used as the best supplemental and restorative nature agent during convalescence and as a prophylactic to build resistance, reduces susceptibility to illness, and promotes health and longevity.

Other functions of ginseng are to stimulate mental and physical activity, strengthen and protect human organism, increase physical and mental efficiency and to prevent fatigue. Ginseng has good effect on the stomach, the brain, and the nervous system. Ginseng is effective for reflex nervous disease. Ginseng has also been found to have an anti-cancer effect. There are more than 30 kinds of ginsenosides, and each one function differently. Ginsenoside $Rh_2$ has anti-tumor activity. Ginsenoside $Rg_1$ can enhance DNA and RNA formation, which may speed up the angiogenesis. In some aspect of the present invention, there is provided a method for promoting autogenous ingrowth of a biological tissue material comprising the steps of providing a natural tissue, removing cellular material from the natural tissue, increasing porosity of the natural tissue by at least 5%, loading an angiogenesis agent or autologous cells into the porosity, and crosslinking the natural tissue with a crosslinking agent. In one preferred embodiment, the angiogenesis agent is ginsenoside $Rg_1$. In still another aspect of the invention, there is provided a method for treating cancer or tumor by implanting a biological tissue material comprising the steps of providing a natural tissue, removing cellular material from the natural tissue, increasing porosity of the natural tissue by at least 5%, loading a cancer/tumor antagonist agent into the porosity, and crosslinking the natural tissue with a crosslinking agent. In one preferred embodiment, the cancer/tumor antagonist is ginsenoside $Rh_2$.

Some aspects of the invention relate to a method for promoting angiogenesis for treating tissue comprising: providing crosslinkable biological solution to the target tissue, wherein the crosslinkable biological solution is loaded with at least one angiogenic agent (also known as angiogenic growth factor) such as ginsenoside $Rg_1$. Some aspects of the invention relate to a method for treating cancer or tumor of a patient comprising: providing crosslinkable biological solution to the target tissue, wherein the crosslinkable biological solution is loaded with at least one cancer/tumor antagonist agent such as ginsenoside $Rh_2$.

EXAMPLE 6

In Vitro Angiogenesis Study with Ginsenoside

In the in vitro study, effects of $Rg_1$ on HUVEC (human umbilical vein endothelial cell) proliferation, migration, and tube formation were investigated, using bFGF (basic fibroblast growth factor) as a reference control. During angiogenesis, activated existing endothelial cells proliferate and their mobile activity increases. The mobile endothelial cells migrate toward the attractants and connect each other to form tube-like structures in vitro or neo-vessels in vivo. The in vitro assays applied in the present study have been widely used and are appropriate models to examine various aspects of angiogenic behaviors of $Rg_1$. HUVECs (Cascade Biologics, Portland, Oreg.) were cultured at 37□ in a humidified atmosphere of 5% $CO_2$ and 95% air in Medium 200 supplemented with low serum growth supplement (LSGS, Cascade Biologics). All experiments were carried out with the same batch of HUVECs.

Proliferation assay on in vitro specimens: HUVECs (6000 cells/0.1 ml) were added to a collagen-coated 96-well plate (Pierce) and incubated with 100 μl of Medium 200 supplemented with LSGS for 24 hours. The cells were then treated with the testing sample by replacing the media with 0.1 ml Medium 200 containing 2% fetal bovine serum (FBS, Cascade Biologics). The growth medium was supplemented with $Rg_1$ (Wako, Osaka, Japan) at 10 ng/ml or 50 μg/ml. A positive control, in which 10 ng/ml bFGF (PeproTech, Rockhill, N.J.) was added, and a negative control, in which no supplemented $Rg_1$ or bFGF was added, were performed. After 48 hours, 100 μl of 20% CellTiter 96® $AQ_{ueous}$ One Solution Reagent (Promega) was added to the wells and the plate was returned to the incubator for 3 hours. The optical density for each well was measured.

Figure 20A:
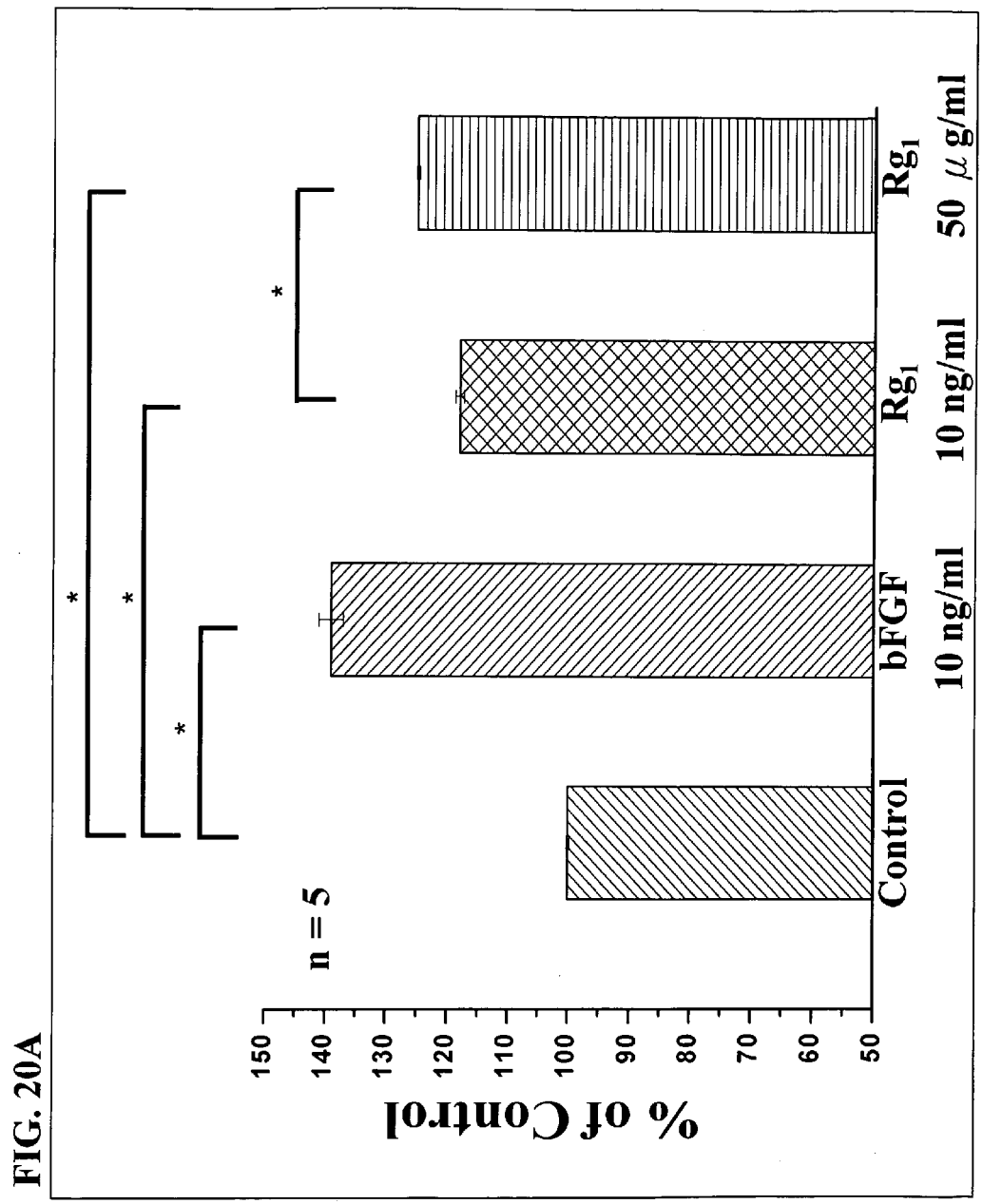
FIG. 20A shows effect of ginsenoside $Rg_1$ on human umbilical vein endothelial cell (HUVEC) proliferation, migration, and tube formation, using bFGF as a control: (A) effect of bFGF or $Rg_1$ on HUVEC proliferation.

The number of viable cells was estimated by the [3-(4,5-dimethylthiazol-2-yl)-5-(3-carboxymethoxyphenyl)-2-(4-sulfophenyl)-2H-tetrazolium, MTS] method using CellTiter 96 $AQ_{ueous}$ One Solution Cell Proliferation Assay. The quantity of formazan product as measured by the amount of 490 nm absorbance was directly proportional to the number of living cells in cultures (FIG. 20A). For bFGF (10 ng/ml), HUVEC proliferation was increased 39% over untreated cells ($p<0.05$). At 10 ng/ml $Rg_1$, cell proliferation was increased 18% over untreated cells, which was found to be statistically significant ($p<0.05$). The proliferation rate of cells exposed to a higher concentration of $Rg_1$ (50 μg/ml) was found to have increased significantly 25% over untreated cells ($p<0.05$). In FIGS. 20A to 20D, the term "n.s." indicates no statistical difference; the term "*" indicates statistical significance at a level of $p<0.05$.

Migration assay on in vitro specimens: The ability of $Rg_1$ to stimulate HUVEC migration was assessed in Transwell plates (6.5 mm, 8 μm, COSTAR, Corning, N.Y.). The upper chambers of these plates were coated with 50 μl of 5% Matrigel™ (BD Biosciences) diluted in Medium 200 containing 2% FBS. The plates were then incubated at 37 for 2 hours. HUVECs were seeded at $1 \times 10^5$ cells in 200 μl to each Transwell. The bottom chambers contained Medium 200 plus 2% FBS and $Rg_1$ at 10 ng/ml or 50 μg/ml. The positive control chambers contained 10 ng/ml bFGF. Medium 200 plus 2% FBS was used as the negative control. The plates were incubated at 37, 5% $CO_2$ for 12 hours. Cells were fixed with 1000 μl of 4% formaldehyde for 30 minutes. Cells on the upper surface of the membrane were removed by gentle wiping with a cotton-tipped swab. The membranes were counter-stained with hematoxylin, and then the number of migrated cells was counted. The assay was quantified by counting the number of cells per microscopic field that migrated through the pores to the lower surface of each membrane with Nikon-E-800 at 200× magnification. Each data point was based on pentaplicate chambers and six microscopic fields per membrane.

Figure 20B:
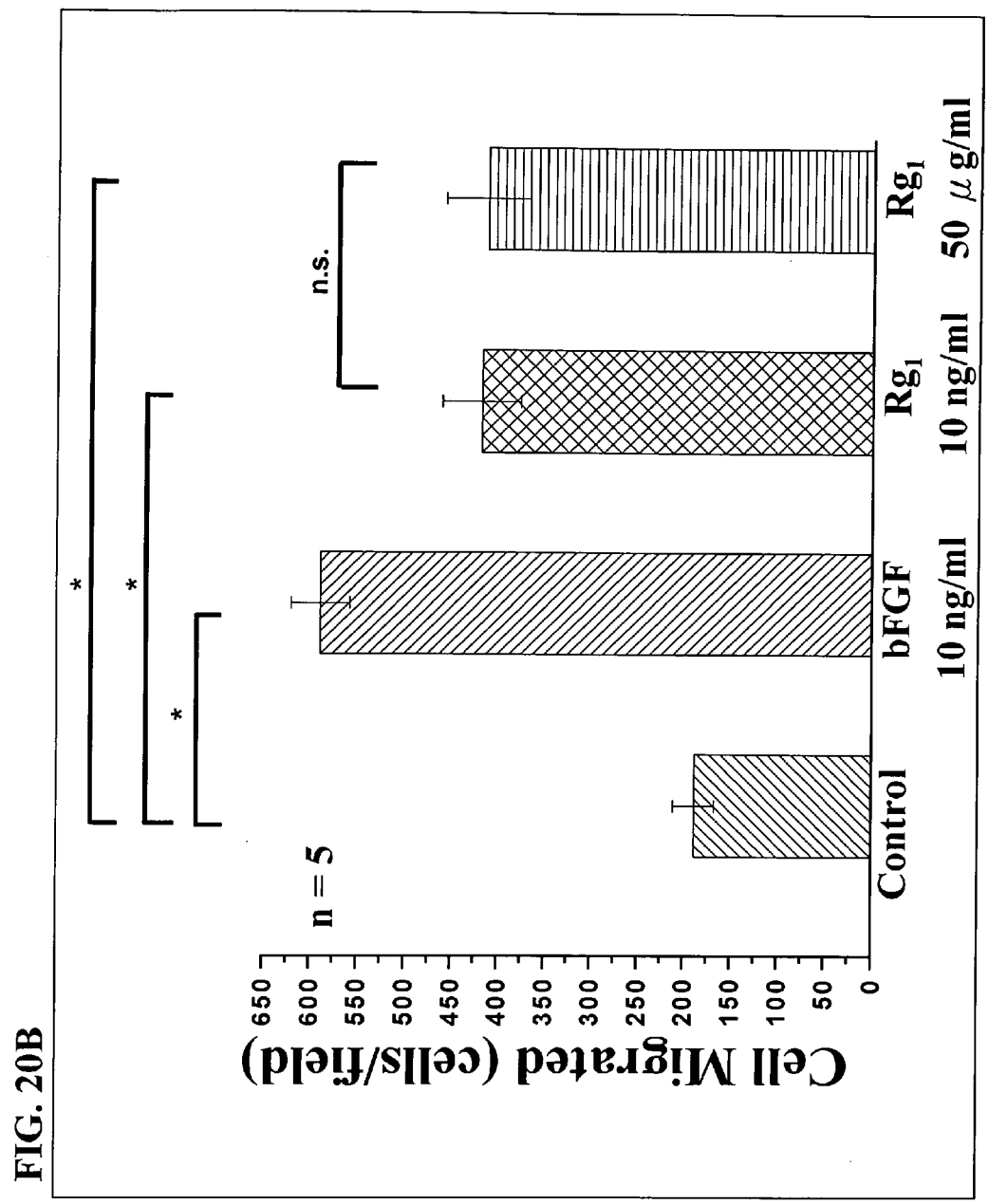
FIG. 20B shows effect of ginsenoside $Rg_1$ on human umbilical vein endothelial cell (HUVEC) proliferation, migration, and tube formation, using bFGF as a control: (B) effect of bFGF or $Rg_1$ on HUVEC migration obtained in a Transwell-plate assay.

FIG. 20B shows the effect of bFGF or $Rg_1$ on HUVEC migration was tested in Transwell plates using Matrigel™-coated membranes. Cells were added to the upper chamber; after 12 hours the number of cells migrated through the membrane in response to bFGF or $Rg_1$ in the lower chamber was quantified. HUVECs treated with bFGF showed more than three times the migratory activity over that of untreated cells, and cells treated with $Rg_1$ migrated at more than twice the rate of untreated cells ($p<0.05$, FIG. 20B).

Tube formation assay on in vitro specimens: Tube formation assays were performed using 96-well plates coated with 50 μl of Matrigel™ per well. HUVECs were plated at a density of 10,000 cells/well in 150 μl of Medium 200 containing 2% FBS. $Rg_1$ was added to the wells at 10 ng/ml or 50 μg/ml, and the plates were incubated for 12 hours at 37. After 12 hours, cells were fixed in 100 μl of 4% formaldehyde for 30 min and the images were taken at 100× magnification. The images were converted into gray scale and the area of the formed tube networks was determined using Image-Pro® Plus (Media Cybernetics, Silver Spring, Md.). Each value was in pentaplicate.

Figure 20C:
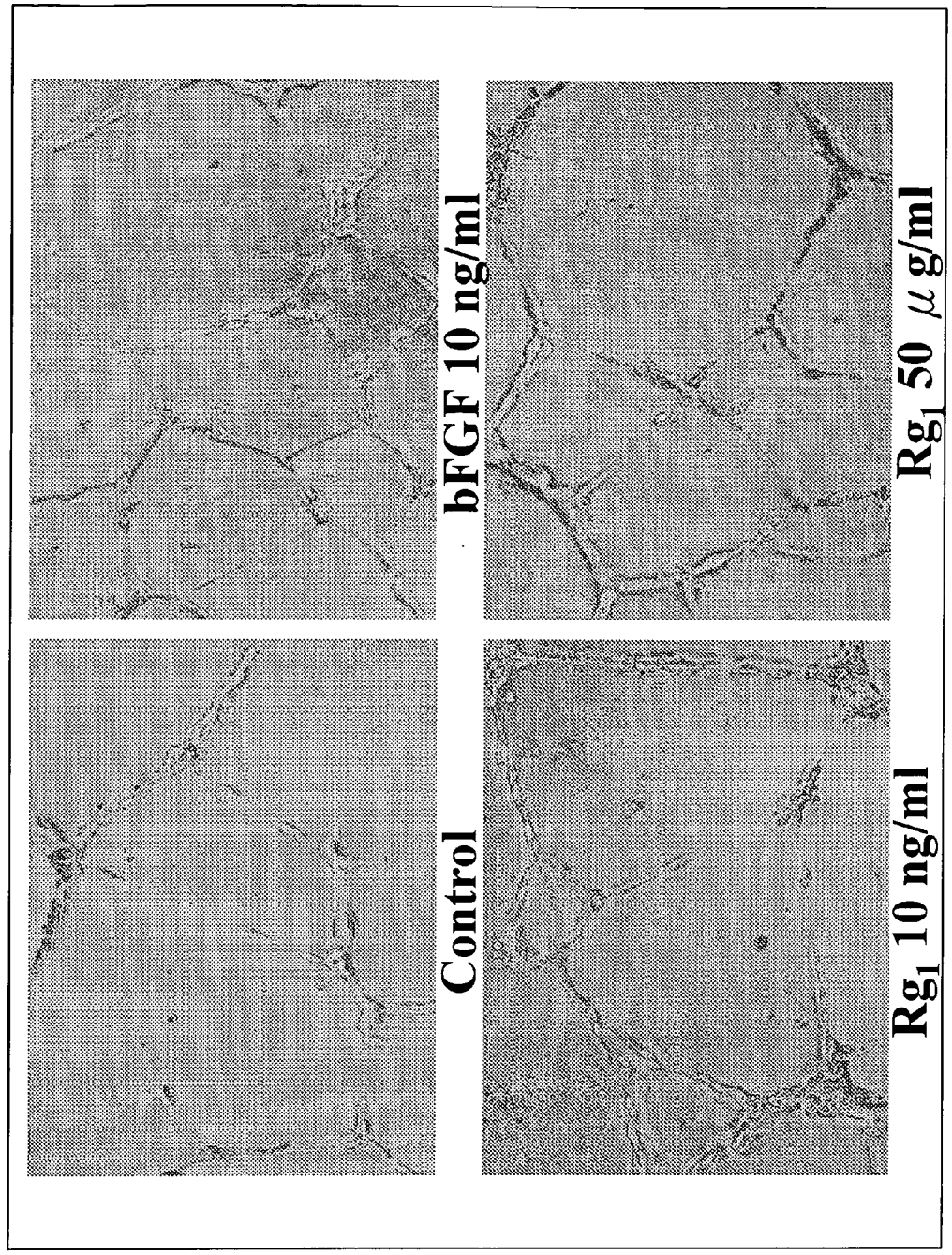
FIG. 20C shows effect of ginsenoside $Rg_1$ on human umbilical vein endothelial cell (HUVEC) proliferation, migration, and tube formation, using bFGF as a control: (C) micrographs showing effect of bFGF or $Rg_1$ on tube formation by HUVECs.
Figure 20D:
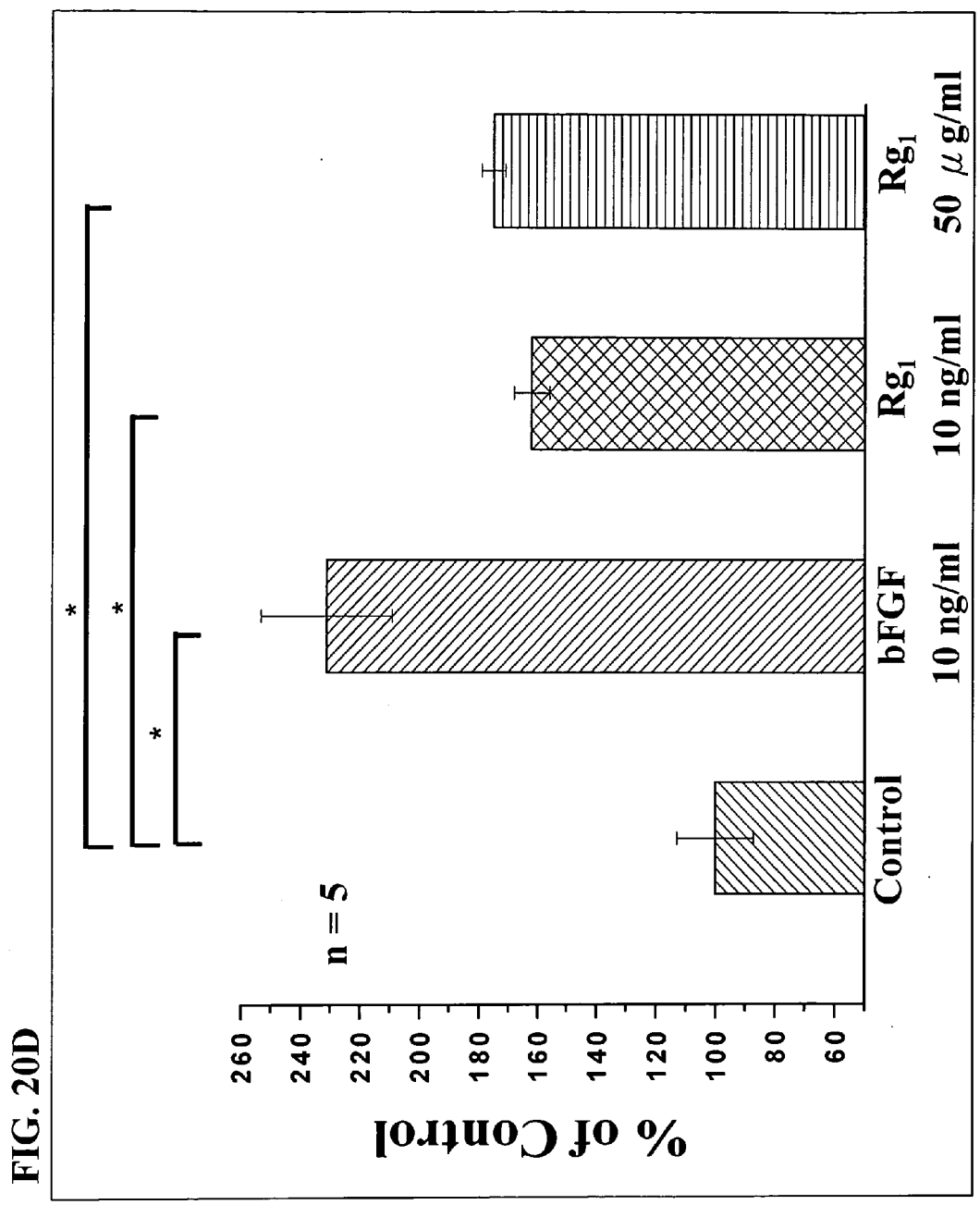
FIG. 20D shows effect of ginsenoside $Rg_1$ on human umbilical vein endothelial cell (HUVEC) proliferation, migration, and tube formation, using bFGF as a control: (D) bar graph showing quantification of tube formation in the presence or absence of bFGF or $Rg_1$. Tube formation was quantitatively estimated by measuring the area covered by the tube network using an image analysis program.

FIG. 20C show effects of bFGF or $Rg_1$ on the morphological differential of HUVECs on Matrigel™ were investigated. When placed on Matrigel™ membrane in the absence of angiogenic factors, HUVECs formed incompletely with narrow tube-like structures (FIG. 20C). With bFGF or $Rg_1$, formation of elongated and robust tube-like structures was observed which were organized by a greater number of cells compared to the control (FIG. 20C). Tube formation was quantitatively estimated by measuring the area covered by the tube network using an image analysis program. FIG. 20D shows that bFGF stimulated tube formation by 2-fold over the control, and $Rg_1$ stimulated tube formation by 2-fold toward the control ($p<0.05$).

The ability of HUVECs to form a network of tubular structures across the surface of a Matrigel™ substratum is a complex phenomenon that combines elements of attachment, migration, organization, and differentiation. The complex organizational behavior of HUVECs on Matrigel™ models the type of coordinated activities required for angiogenesis by endothelial cells. Although the in vitro Matrigel™ model does not represent true angiogenesis, it suggested that bFGF, $Rg_1$, or the like is important for many of the activities that contribute to vessel formation. Thus, the aforementioned results indicated that both bFGF (a protein type angiogenesis factor) and $Rg_1$ (a non-protein type angiogenesis factor) enhanced several in vitro HUVEC activities that are relevant to angiogenesis, including proliferation, migration, and tube formation.

$Rg_1$ has a steroid backbone and contains two molecules of glucose at its 6th and 18th positions (FIG. 12). The steroid backbone of $Rg_1$ makes it a suitable candidate to interact and activate steroid receptors, such as glucocorticoid and estrogen receptors. It was reported that estrogen induces endothelial proliferation and migration mediated by the classic estrogen receptor, which is expressed by endothelial cells. Additionally, ginsenoside and its purified form $Rg_1$ were shown to induce nitric oxide in endothelial cells and caused vasodilatation (Am J Chin Med 1995; 13:279–287). Nitric oxide has been reported to be a downstream mediator in the angiogenic response to a variety of growth factors, but the mechanisms by which nitric oxide promotes neo-vessel formation is not clear.

Figure 13:
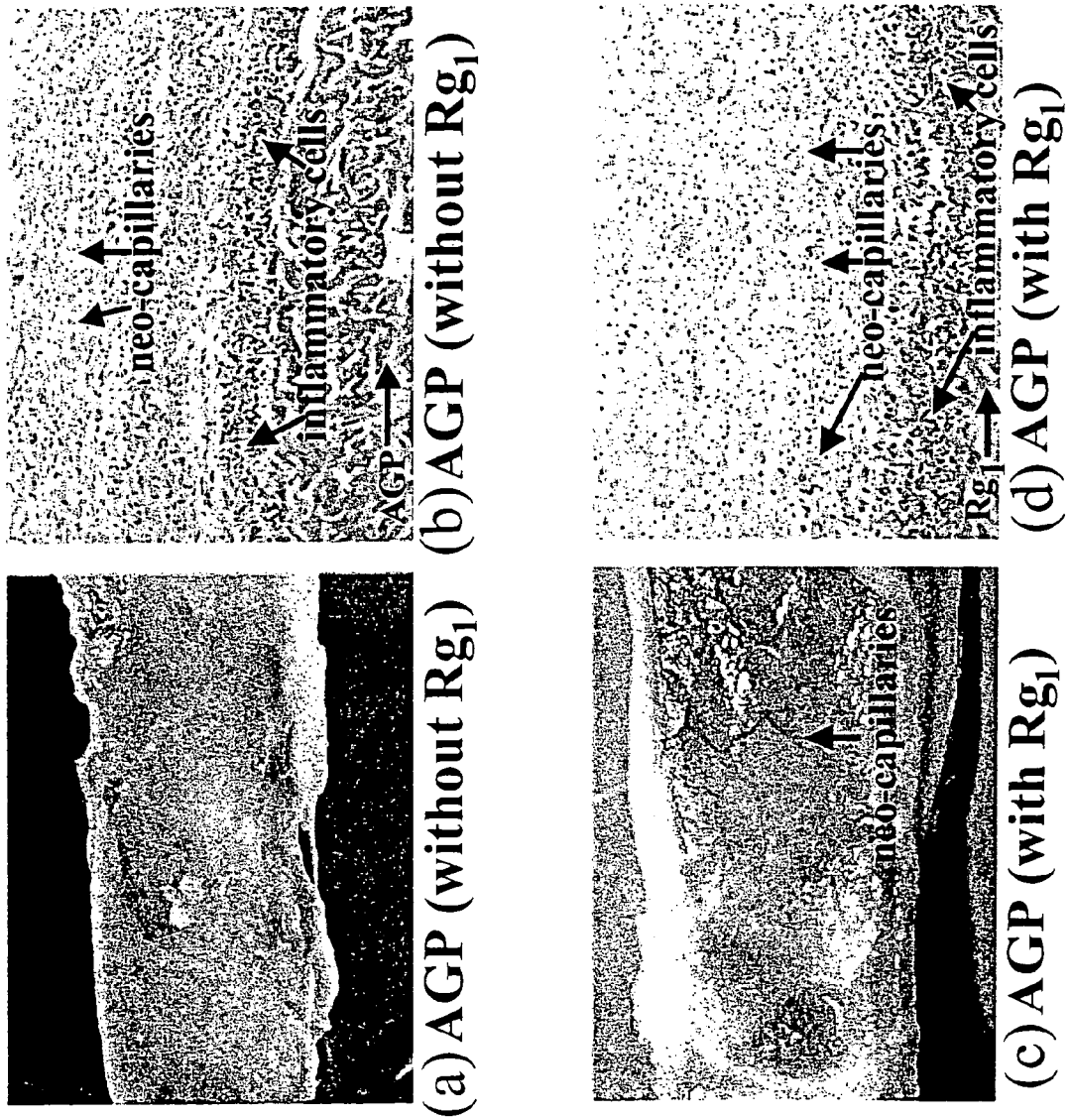
FIG. 13 are cells infiltration extents of genipin-crosslinked acellular bovine pericardia tissue with angiogenesis factors for (a) specimen-AGP, without $Rg_1$; (b) light microscopy of specimen a; (c) specimen-AGP, with $Rg_1$; and (d) light microscopy of specimen c; all explants retrieved at 1-week postoperatively.

FIG. 13 show cells infiltration extents of genipin-crosslinked acellular bovine pericardia tissue with angiogenesis factors for (a) specimen-AGP, without $Rg_1$; (b) light microscopy of specimen a (specimen-AGP, without $Rg_1$); (c) specimen-AGP, with $Rg_1$; and (d) light microscopy of specimen c (specimen-AGP, with $Rg_1$); wherein all implants are retrieved at 1-week postoperatively. The micro-vessel numbers per field (on a reference basis) are measured under a microscope using an imaging processing software. The micro-vessel density for the $Rg_1$ loaded explant (specimen (b) in FIG. 13) is 778 vessels/mm$^2$ that is statistically significantly higher than the micro-vessel density for the control explant (specimen (d) in FIG. 13) of 341 vessels/mm$^2$.

In some aspects of the present invention, the acellular tissue structure with a porosity increase of more than 5% is also suitable for use in anti-adhesion patches for abdominal surgery, anti-adhesion patches for cardiovascular surgery, acellular matrix for regeneration of myocardiocytes, and vascular grafts. $Rg_1$ has shown properties of stimulating HUVEC proliferation, tube formation and chemoinvasion in in vitro studies (T.P.Fan at $3^{rd}$ Asian International Symposium on Biomaterials and Drug Delivery Systems, Apr. 16, 2002). Some aspects of the invention relate to a method for promoting angiogenesis in a subject in need thereof, comprising administering to the subject a substrate loaded with therapeutically effective amount of a non-protein angiogenesis factor (for example, ginsenoside $Rg_1$ and/or ginsenoside Re), wherein the substrate may comprise acellular tissue, artificial organs, wound dressing device in wound care, and prostheses/implants.

EXAMPLE 7

In Vivo Angiogenesis Study

Preparation of test ECMs: The procedures used to remove the cellular components from bovine pericardia were based on a method previously reported. To increase pore sizes and porosities within test samples, the acellular tissues were treated additionally with acetic acid and collagenase. Subsequently, acellular tissues were fixed in a 0.05% genipin (Challenge Bioproducts, Taiwan) aqueous solution (pH 7.4) at 37 for 3 days. The chemical structure of genipin can be found in the literature. The denaturation temperature and porosity of the fixed ECMs were measured in a differential scanning calorimeter and by helium pycnometery, respectively (n=5). The pore size of the fixed ECMs stained with hematoxylin and eosin (H&E) was determined under a microscope (n=5). The fixed ECMs were sterilized in a graded series of ethanol solutions. Finally, the sterilized ECMs were rinsed in sterilized phosphate buffered saline (PBS).

Figure 18:
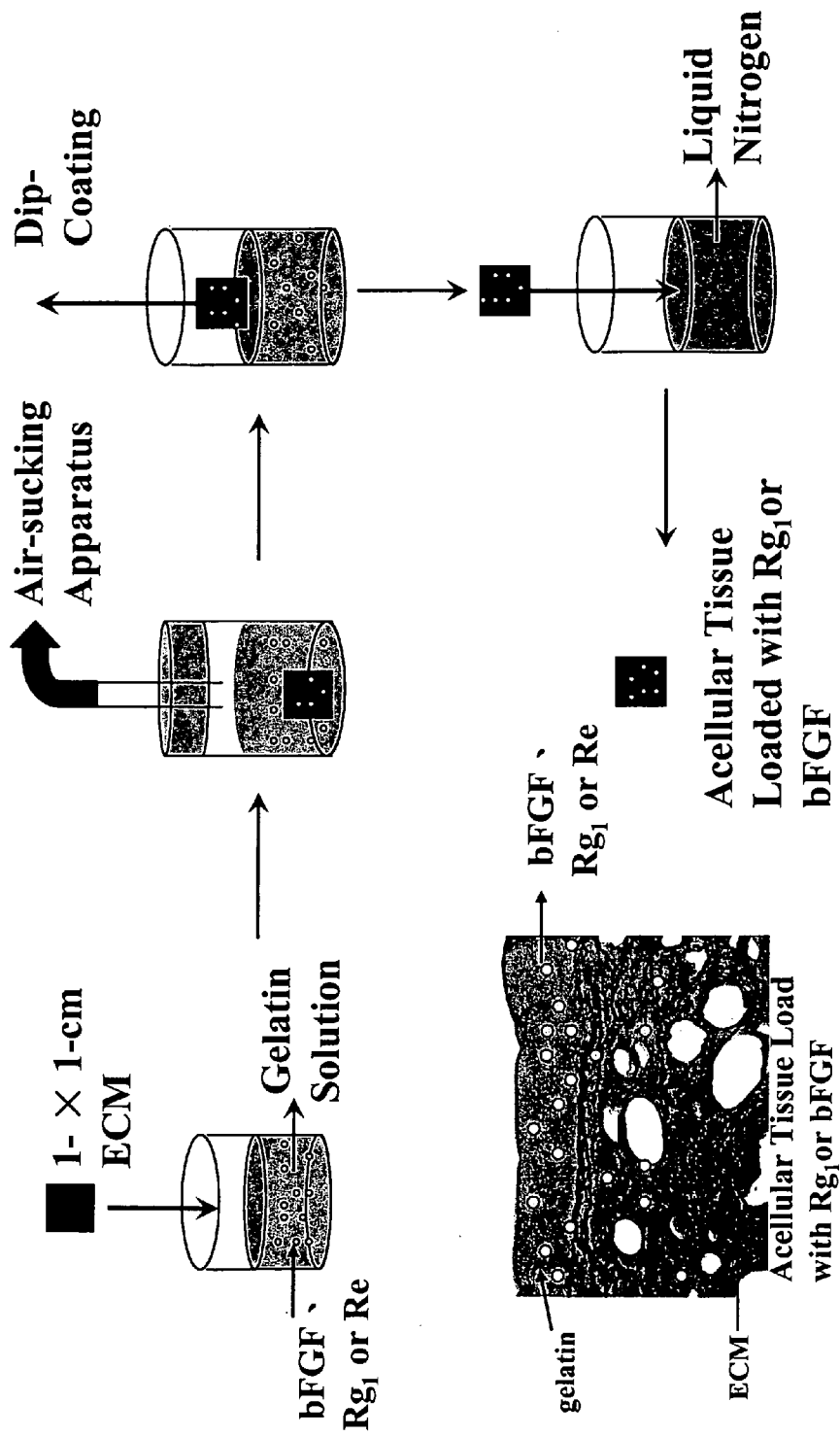
FIG. 18 is a preparation method of loading an acellular tissue with growth factors $Rg_1$, Re, or bFGF.

FIG. 18 shows a preparation method of loading an acellular tissue with ginsenoside $Rg_1$ or ginsenoside Re (both are organic compound growth factors, belonging to non-protein angiogenesis factor category), or bFGF (a protein type growth factor which has a short shelf life). As shown in FIG. 18, extracellular membranes of 1-cm by 1-cm specimens are used to load model growth factors onto the specimens by air-sucking, dip coating and liquid nitrogen cooling steps. The animal implant study includes a rat intramuscular model, wherein the test groups are loaded with 0.7 µg $Rg_1$, 0.7 µg bFGF, 70 µg $Rg_1$ or 70 µg Re growth factors.

To incorporate bFGF (0.7 µg) or $Rg_1$ (0.7 or 70 µg) in the ECMs, bFGF or $Rg_1$ were dissolved in a sterilized gelatin (300 mg/ml PBS, from porcine skin, 225 Bloom, Sigma) aqueous solution. Following vigorous mixing of the solution, the prepared ECMs were dip-coated in the drug-containing gelatin solution under a reduced pressure environment and subsequently gelled in liquid nitrogen. The ECM without loading any drug was used as a blank control.

An extracellular matrix (ECM) is prepared by removing the cellular components of bovine pericardia. Additionally, to increase the pore size and porosity within the ECM, the acellular tissue was further treated with acetic acid and subsequently with collagenase. It is generally accepted that a tissue-engineering extracellular matrix must be highly porous for a sufficient cell density to be seeded in vitro, for blood invasion to occur in vivo, and for oxygen and nutrients to be supplied to cells. It was found by transmission electron microscopy in our previous study that the cellular extraction process used in the study produced a complete extraction and left no cell membrane or nuclear structures within the tissue. The denaturation temperature of the genipin fixed ECM was 74.6±0.6 and its pore size and porosity were approximately 130.3±14.6 µm and 94.9±1.7%, respectively.

Genipin can be obtained from its parent compound, geniposide, which may be isolated from the fruits of *Gardenia jasminoides* ELLIS. Genipin and its related iridoid glucosides have been widely used as an antiphlogistic and cholagogue in herbal medicine. It was found in our previous study that genipin can react with free amino groups such as lysine, hydroxylysine, or arginine residues in biological tissues. The reaction mechanism of genipin with biological tissues was previously proposed. The cytotoxicity of genipin was previously studied by our group in vitro using 3T3 fibroblasts. Glutaraldehyde was used as a control. The results indicated that genipin is significantly less cytotoxic than glutaraldehyde. Additionally, the genotoxicity of genipin was tested in vitro using Chinese hamster ovary (CHO-K1) cells. The results suggested that glutaraldehyde may produce a weakly clastogenic response in CHO-K1 cells. In contrast, genipin does not cause clastogenic response in CHO-K1 cells.

EXAMPLE 8

In Vivo Angiogenesis Study with Ginsenoside

In vivo rat subcutaneous study: In total, 40 rats (4-week-old male Wistar) divided into four groups (ECM/control, ECM/bFGF, ECM/$Rg_1$ –0.7, and ECM/$Rg_1$ –70) were used in the study. Two test samples (~10×10 mm) of the same type were separately implanted subcutaneously in each rat under aseptic conditions. The implanted samples were retrieved at 1-week and 1-month postoperatively (n=5 rats at each time point). At retrieval, the appearance of each retrieved sample was grossly examined and photographed. Subsequently, half of each retrieved sample was fixed and embedded in paraffin for the histological examination, and the remainder of the sample was used to quantify the amount of tissue hemoglobin.

Figure 19:
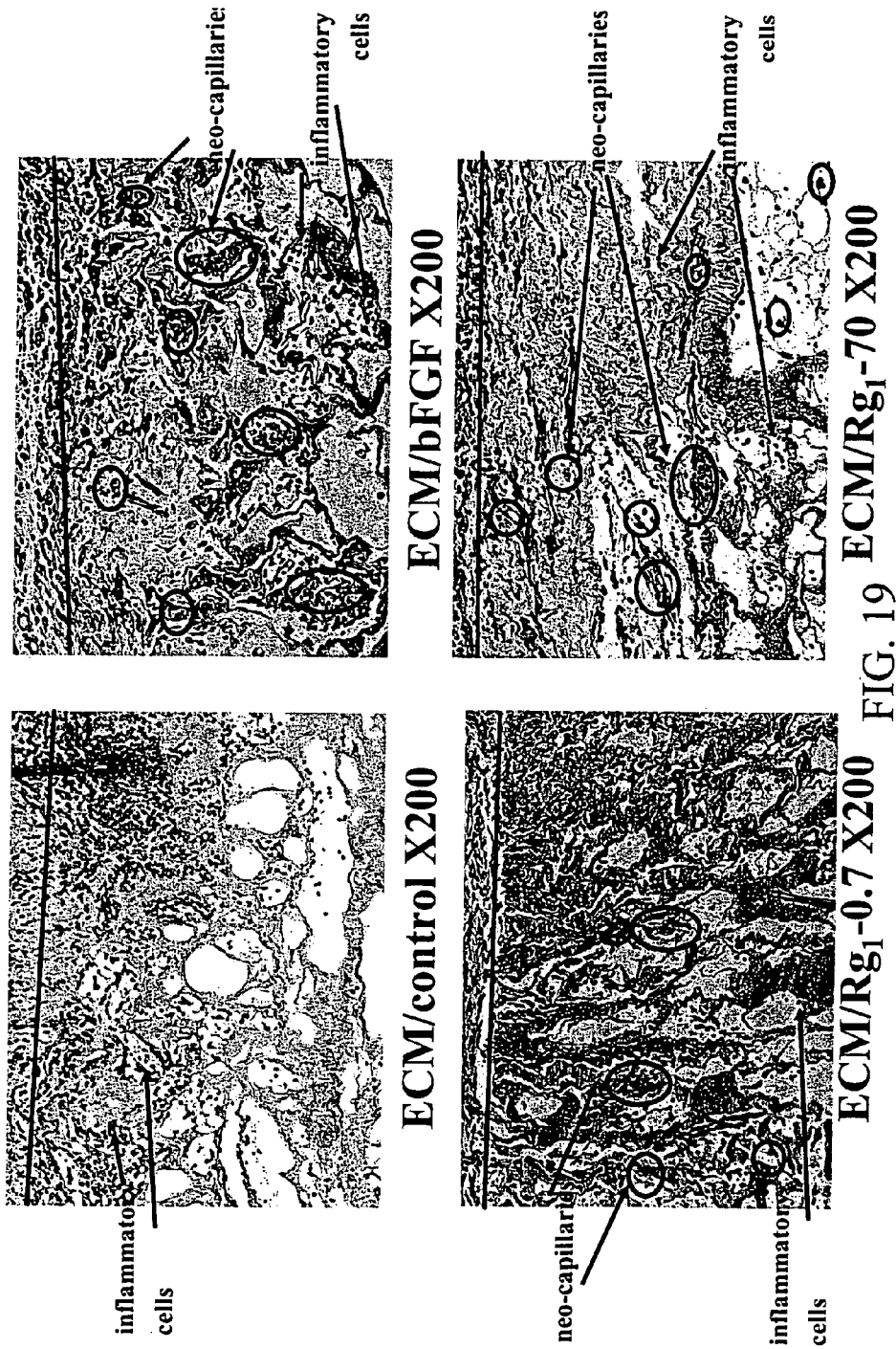
FIG. 19 is 1-week postoperative results on animal angiogenesis study: photomicrographs of H&E (hematoxylin and eosin) stained tissue.

FIG. 19 shows 1-week postoperative results on animal angiogenesis study: photomicrographs of H&E (hematoxylin and eosin) stained tissue explant. Both organic compound growth factor and protein growth factor promote angiogenesis as evidenced by enhanced neo-capillaries and tissue hemoglobin measurements as compared to control. However, the protein growth factors tend to have a shorter shelf life than the organic growth factors.

In the histological examination, the fixed samples were stained with H&E. The stained sections of each test sample were examined using light microscopy for tissue inflammatory reaction and tissue regeneration. The number of inflammatory cells observed in each studied case was quantified with a computer-based image analysis system (Image-Pro® Plus) at 200× magnification. Also, the density and depth (in percentage of the depth of the whole test sample) of blood vessels infiltrated into each studied sample were quantified with the same image analysis system. A minimum of five fields was counted for each retrieved sample.

Immunohistochemical staining was performed on the paraffin sections with a labeled streptavidin-biotin immunoenzymatic antigen detection system (DAKO LSAB®2 System, Dako Co., Carpinteria, Calif.). The paraffin sections were digested enzymatically with pepsin (1 mg/ml in 0.01N of HCl) for 30 minutes at 37□. Collagen types I and III mouse monoclonal antibodies were obtained from ICN Biomedicals Inc. (Aurora, Ohio). The subcutaneous tissue of a healthy rat and the ECM used in the study were used as the positive and negative controls, respectively. Additional sections were stained for factor VIII with immunohistological technique with a monoclonal anti-factor VIII antibody (Dako Co., Carpinteria, Calif.).

The extent of vascularization in each retrieved sample was determined by measuring the amount of tissue hemoglobin. Test samples were fragmented with a scalpel and immersed in 17 mM Tris-HCl buffer solution (pH 7.6) containing 0.75% ammonium chloride for 24 hours at 4□ to extract hemoglobin in test samples. The extracted hemoglobin was quantitated using a hemoglobin assay kit (Wako, Osaka, Japan).

Figure 21:
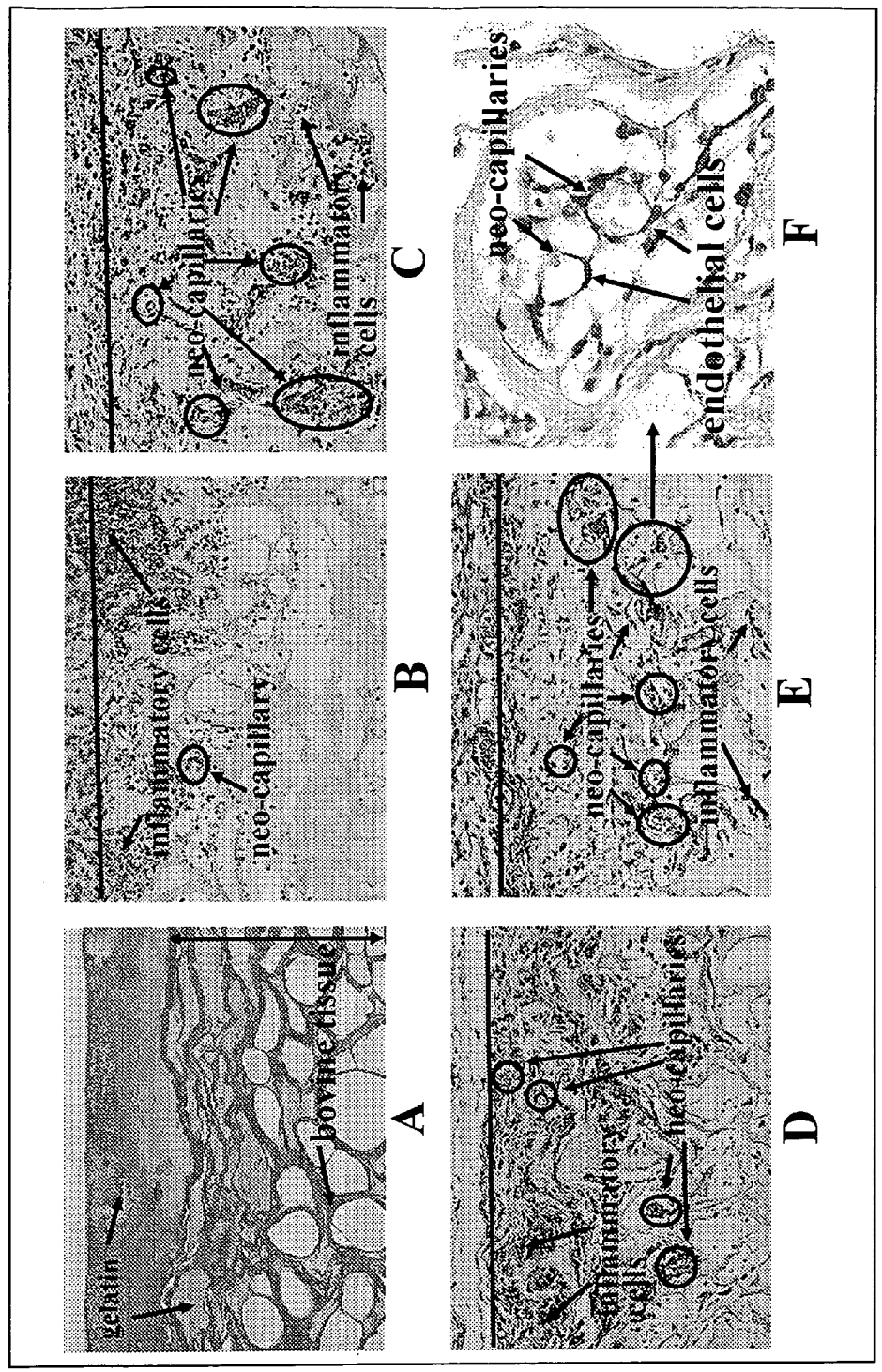
FIG. 21 is histological evaluation of the tissue responses to test ECMs implanted subcutaneously in a rat model retrieved at 1-week postoperatively: (A) photomicrograph of the ECM dip-coated in a gelatin hydrogel incorporated with $Rg_1$ at 70 μg stained with H&E before implantation; photomicrographs of (B) the ECM without loading any drug (ECM/control), (C) the ECM loaded with 0.7 μg bFGF (ECM/bFGF), (D) the ECM loaded with 0.7 μg $Rg_1$ (ECM/$Rg_1$ −0.7), and (E) the ECM loaded with 70 μg $Rg_1$ (ECM/$Rg_1$ −70) retrieved at 1-week postoperatively stained with H&E (200× magnification); (F) photomicrograph of the ECM/$Rg_1$ −70 retrieved at 1-week postoperatively stained with factor VIII (800× magnification).

Angiogenesis and tissue regeneration in the genipin-fixed ECMs loaded with $Rg_1$ at 0.7 μg (ECM/$Rg_1$ –0.7) or 70 μg (ECM/$Rg_1$ –70) were investigated subcutaneously in a rat model. FIG. 21A shows photomicrograph of the ECM dip-coated in a gelatin hydrogel incorporated with $Rg_1$ at 70 μg stained with H&E before implantation. The ECMs without drug (ECM/control) or loaded with 0.7 μg bFGF (ECM/bFGF) were used as blank and positive controls, respectively. At 1-week postoperatively, a thin layer of transparent tissue enriched with blood capillaries surrounded the ECM/bFGF, ECM/$Rg_1$ –0.7 and ECM/$Rg_1$ –70. In contrast, there was no macroscopic evidence of any angiogenesis for the ECM/control.

Figure 22A:
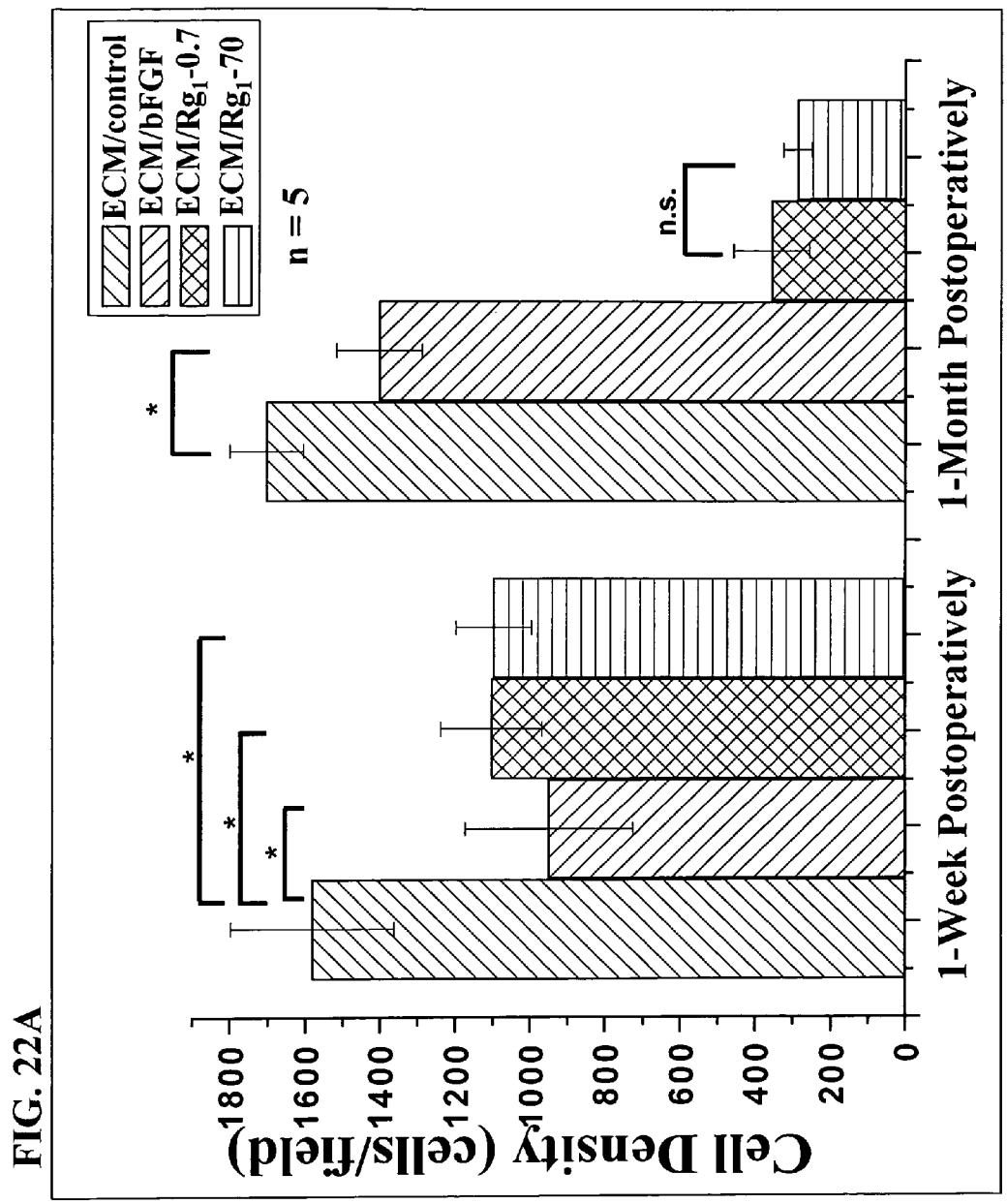
FIG. 22A is quantitative analyses of the cell density and the density and depth of blood vessels infiltrated and the tissue hemoglobin content observed in each test ECM retrieved at 1-week and 1-month postoperatively: (A) the cell density observed in each test ECM.
Figure 22B:
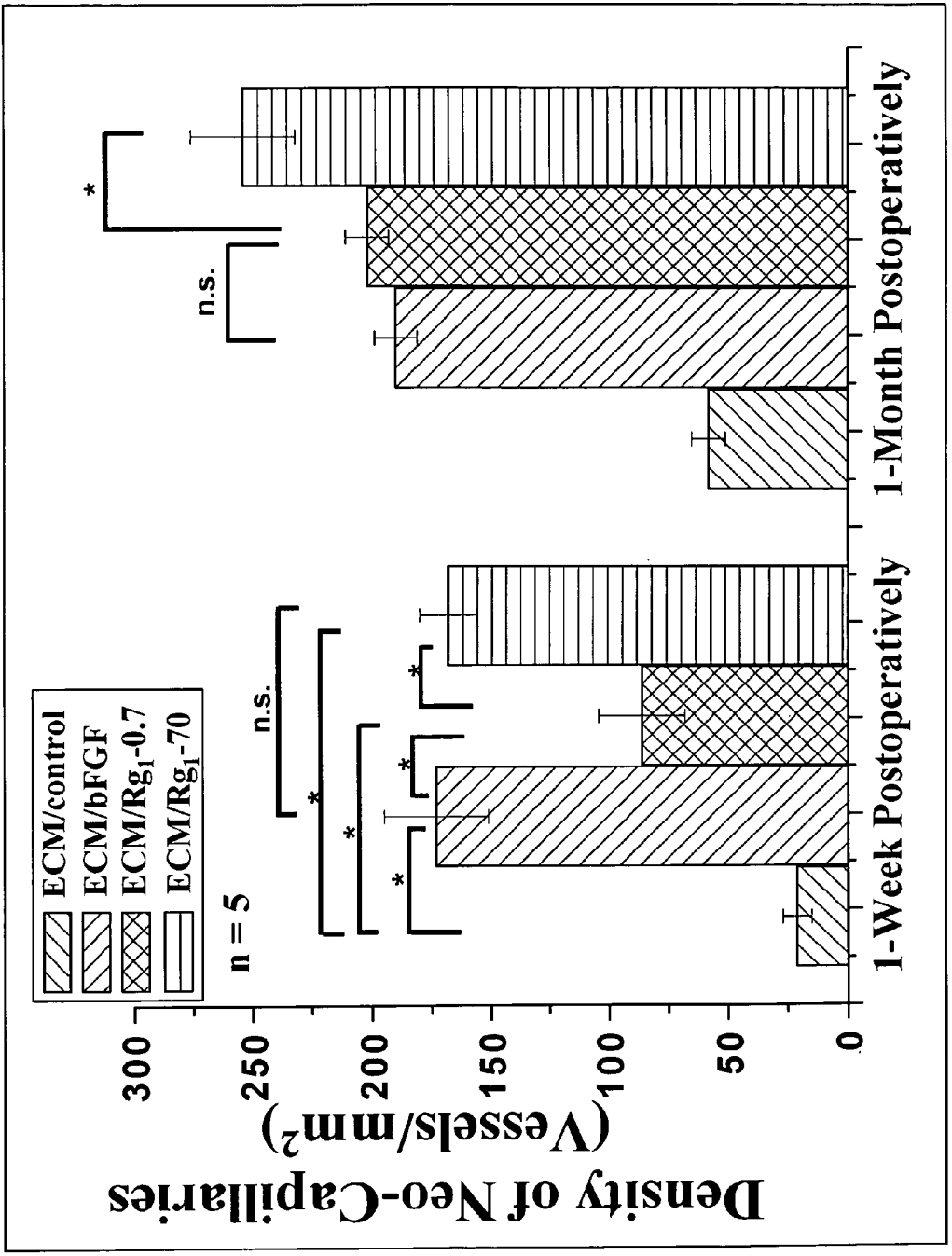
FIG. 22B is quantitative analyses of the cell density and the density and depth of blood vessels infiltrated and the tissue hemoglobin content observed in each test ECM retrieved at 1-week and 1-month postoperatively: (B) the density (in percentage of the depth of the whole test sample) of blood vessels infiltrated into each test ECM.
Figure 22C:
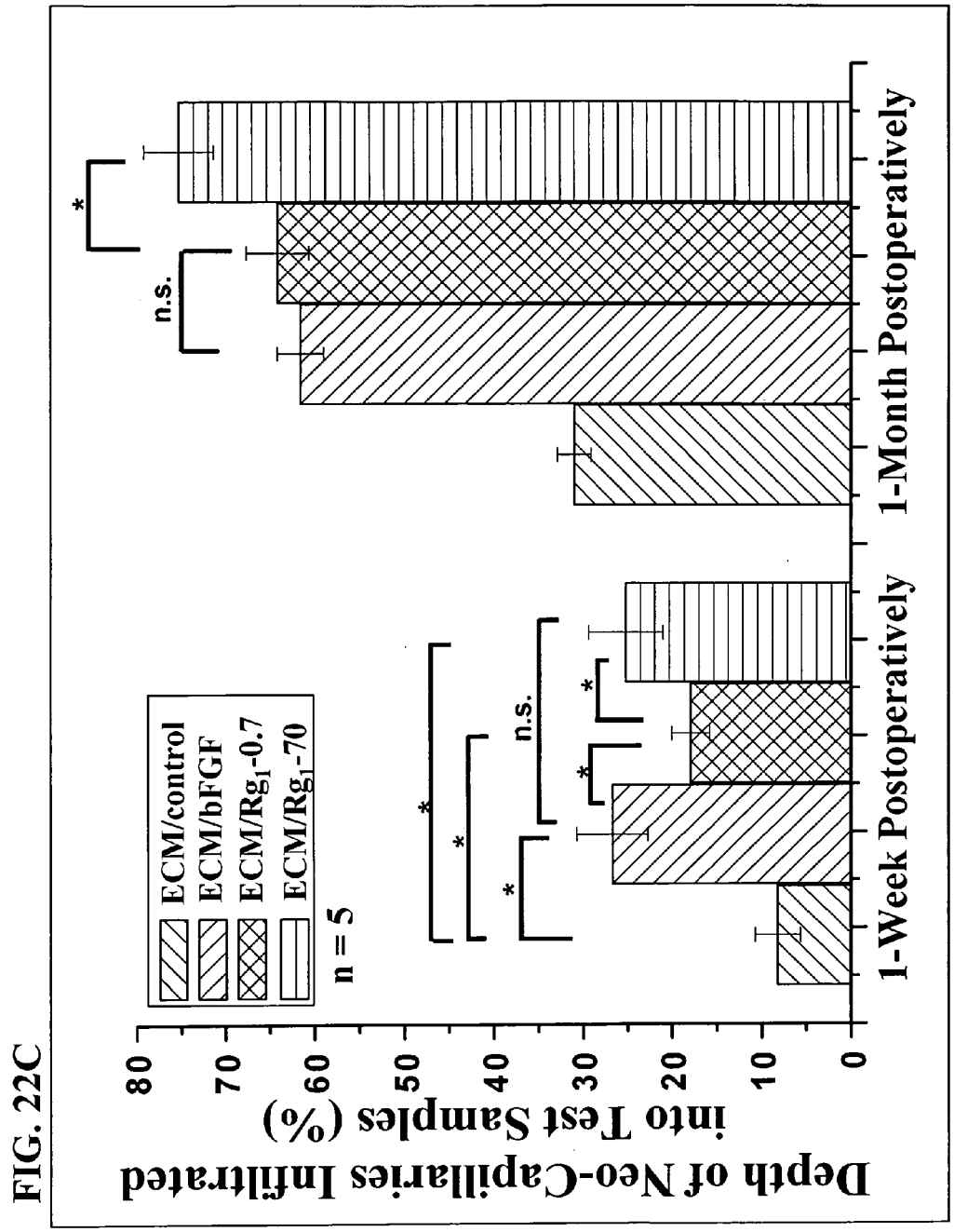
FIG. 22C is quantitative analyses of the cell density and the density and depth of blood vessels infiltrated and the tissue hemoglobin content observed in each test ECM retrieved at 1-week and 1-month postoperatively: (C) the depth (in percentage of the depth of the whole test sample) of blood vessels infiltrated into each test ECM.

FIGS. 21B to 21E present photomicrographs of each studied group retrieved at 1-week postoperatively stained with H&E. The solid line in each photograph represents the interface between the host tissue (rat) and the implanted test sample. As shown, host cells (inflammatory cells, endothelial cells, and red blood cells) were able to infiltrate into the open spaces of all test ECMs. The amount of inflammatory cells infiltrated into the ECM/control was the most remarkable among all studied groups ($p<0.05$, FIG. 22A). The density and depth of neo-capillaries infiltrated into the ECMs loaded with bFGF or $Rg_1$ were significantly greater than the control ECM without drug loading (FIGS. 22B and 22C, $p<0.05$). FIG. 21F presents a photomicrograph of the ECM/$Rg_1$ –70 retrieved at 1-week postoperatively stained with factor VIII.

As shown, in-growing capillaries were coated with an inner endothelial layer. These results indicates that angiogenesis in the ECMs was significantly enhanced by loading with bFGF (a protein angiogenesis factor) or $Rg_1$ (a non-protein angiogenesis factor). It is known that site-specific delivery of angiogenic molecules may provide an efficient means of stimulating localized vessel formation. The ECMs dip-coated with a gelatin hydrogel incorporated with bFGF or $Rg_1$ prepared in the study may allow one to optimize this process. It was noted that there were more neo-capillaries and tissue hemoglobin measured in the ECM/bFGF and ECM/$Rg_1$ –70 than in the ECM/$Rg_1$ –0.7 ($p<0.05$, FIGS. 22B and 22D); however, there were no significant differences between the former two test samples ($p>0.05$). In FIGS. 22A to 22D, the term "n.s." indicates no statistical difference; the term "*" indicates statistical significance at a level of $p<0.05$.

Figure 23:
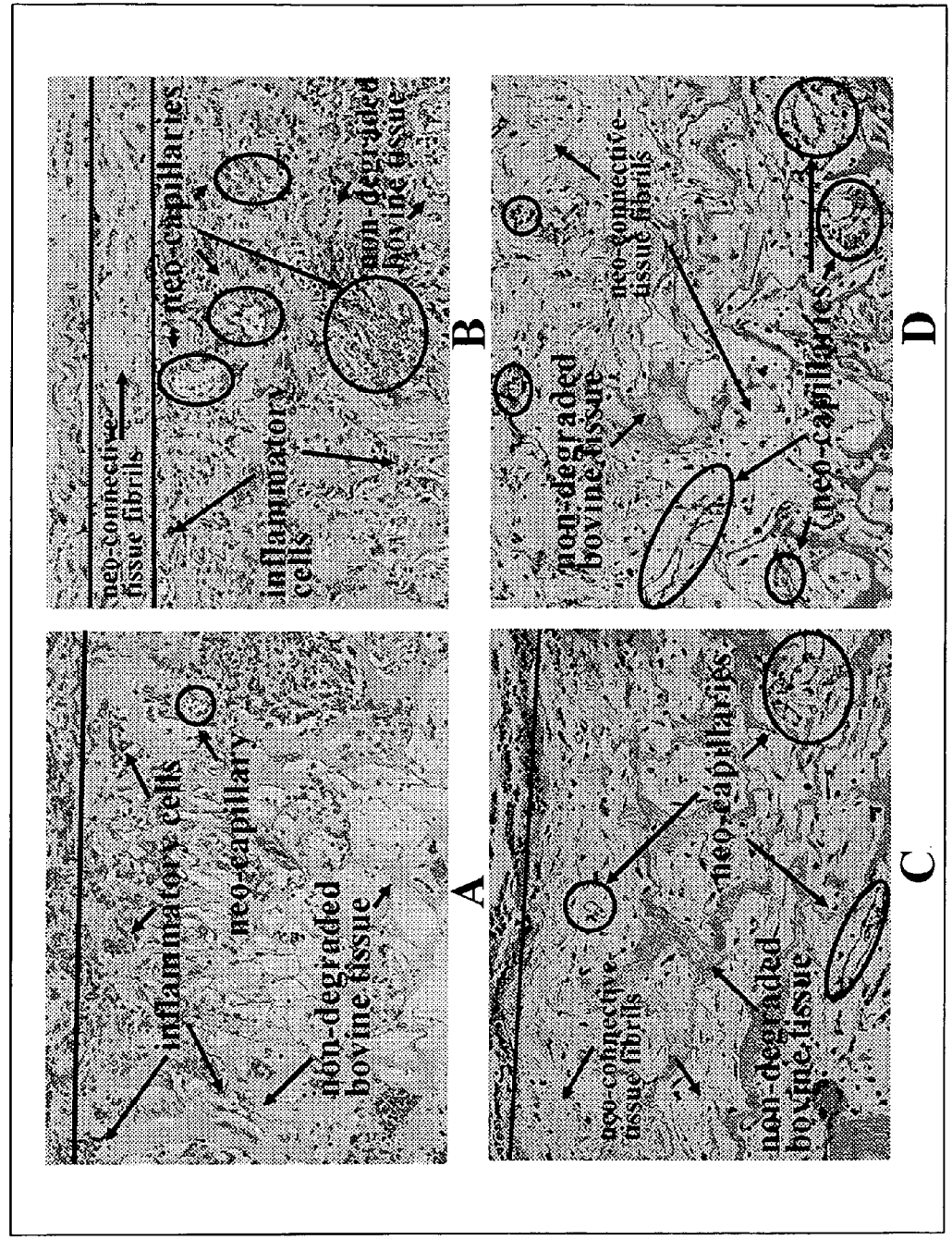
FIG. 23 is histological evaluation of the tissue responses to test ECMs implanted subcutaneously in a rat model retrieved at 1-month postoperatively: photomicrographs of (A) ECM/control, (B) ECM/bFGF, (C) ECM/$Rg_1$ −0.7, and (D) ECM/$Rg_1$ −70 retrieved at 1-month postoperatively stained with H&E (200× magnification).
Figure 24:
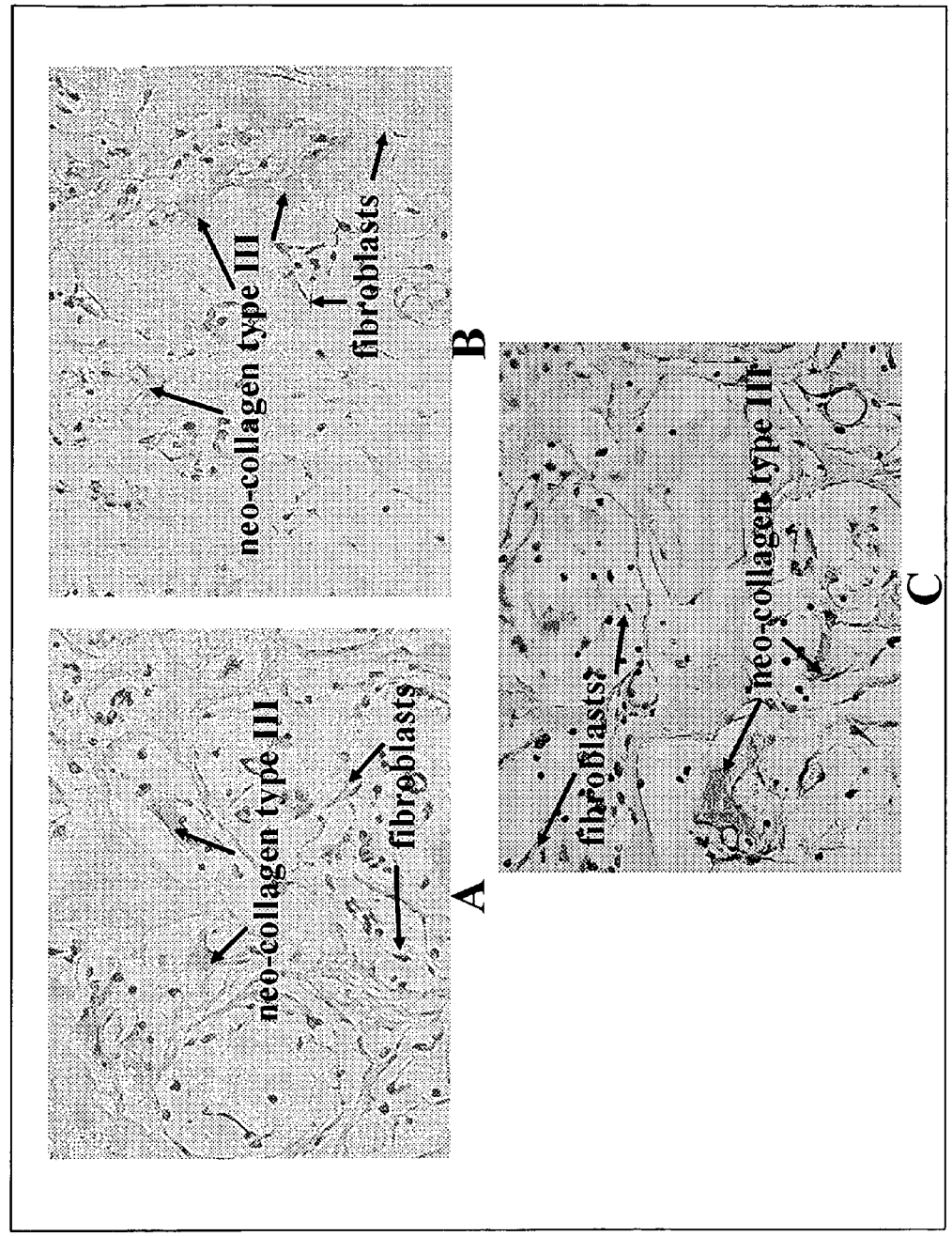
FIG. 24 is the neo-connective tissues observed in the pores of each test ECM loaded with bFGF or $Rg_1$ were identified by the immunohistochemical stains to contain neo-collagen type I and III fibrils regenerated from the host rat: photomicrographs of (A) ECM/bFGF, (B) ECM/$Rg_1$ −0.7, and (C) ECM/$Rg_1$ −70 retrieved at 1-month postoperatively obtained by the immunohistochemical stains to identify neo-collagen type III (400× magnification).
Figure 25:
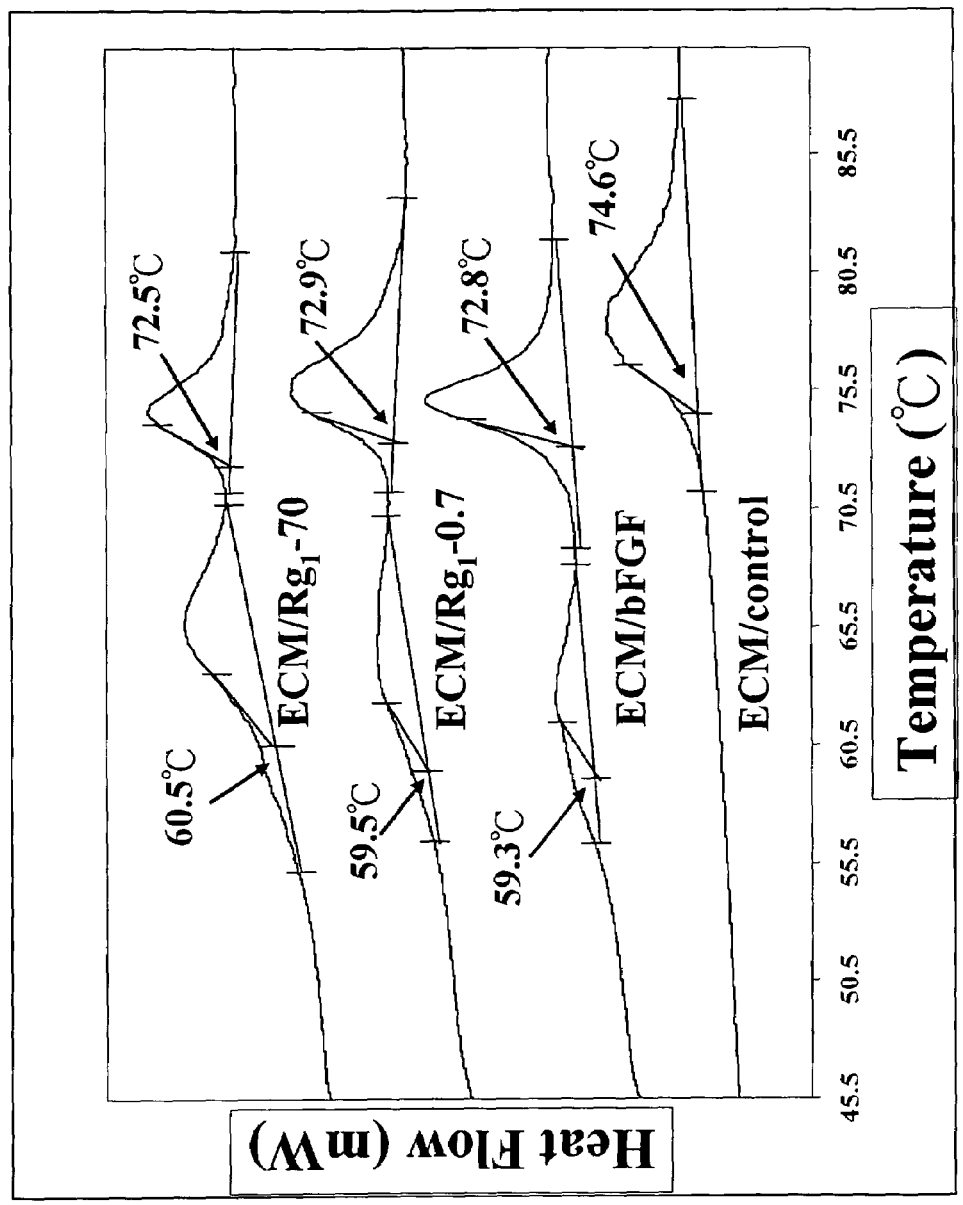
FIG. 25 is thermograms of each studied group retrieved at 1-month postoperatively measured by a differential scanning calorimeter. The neo-collagen fibrils regenerated from the host in each test ECM loaded with bFGF or $Rg_1$ can be confirmed by the denaturation-temperature measurements. As shown, two denaturation-temperature peaks were observed for the ECMs loaded with bFGF (ECM/bFGF) or $Rg_1$ (ECM/$Rg_1$ −0.7 and ECM/$Rg_1$ −70): one was the original bovine collagen fixed with genipin (~73 □) and the other was the neo-collagen regenerated from the host (~60□). In contrast, there was only one peak (~74□) observed for the ECM without loading any drug (ECM/control).

At 1-month postoperatively, inflammatory cells in the outer layers of the ECM/$Rg_1$ –0.7 and ECM/$Rg_1$ –70 had almost disappeared, while there were still some inflammatory cells observed in the ECM/bFGF (FIGS. 23B–23D). Instead, fibroblasts (migration from the host tissue), neo-capillaries, and neo-connective-tissue fibrils were found to fill the pores in this area, indicating that the tissue was being regenerated. The neo-connective tissues were identified by the immunohistochemical stains to contain neo-collagen type I and type III fibrils regenerated from the host rat (FIGS. 24A–24C). The neo-collagen fibrils regenerated from the host in these ECMs can be further confirmed by our denaturation-temperature measurements. As shown in FIG. 25, there were two denaturation-temperature peaks observed for these ECMs (~60□ and ~73 □). One was the denaturation temperature of the original bovine collagen fixed with genipin (~73□), and the other was that of the neo-collagen fibrils regenerated from the host (i.e., the rat tissue, ~60□).

In contrast, there were still a large number of inflammatory cells with minimal neo-capillaries and neo-connective-tissue fibrils seen in the ECM/control (FIG. 23A). Also, there was only one denaturation-temperature peak observed for the ECM/control (the genipin-fixed bovine collagen, ~74□) due to its minimal regeneration of collagen fibrils from the host at this time. These results indicated that $Rg_1$-associated induction of angiogenesis enhanced tissue regeneration, supporting the concept of therapeutic angiogenesis in tissue-engineering strategies.

Figure 22D:
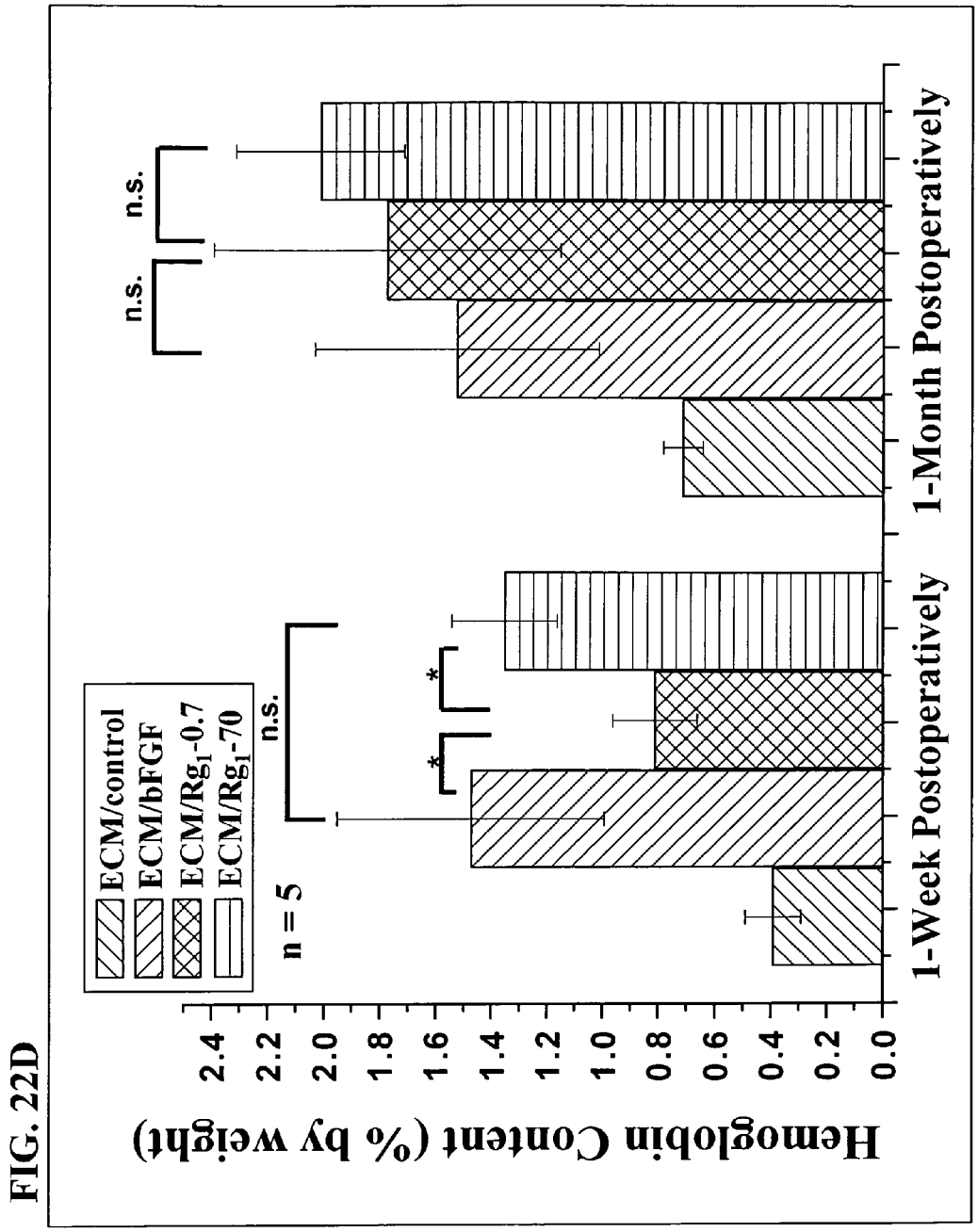
FIG. 22D is quantitative analyses of the cell density and the density and depth of blood vessels infiltrated and the tissue hemoglobin content observed in each test ECM retrieved at 1-week and 1-month postoperatively: (D) the tissue hemoglobin content observed in each test ECM.

The densities of neo-capillaries and tissue hemoglobin infiltrated into the ECM/$Rg_1$ –0.7 and ECM/$Rg_1$ –70 were significantly greater than their counterparts observed at 1-week postoperatively ($p<0.05$), while those seen in the ECM/bFGF stayed approximately the same ($p>0.05$, FIGS. 22B and 22D). These results suggested that the delivered $Rg_1$ continued to be effective in enhancing angiogenesis. In contrast, although bFGF can enhance angiogenesis at 1-week postoperatively, it is difficult to achieve long-term delivery of functional properties because of the limitations of protein stability. It was reported that at physiological pH and temperature, the in vitro half-lifetime of bFGF activity (a protein angiogenesis factor) is approximately 12 hours. In contrast, it was shown that degradation of $Rg_1$ (a non-protein angiogenesis factor) under neutral intestinal pH conditions is negligible throughout the experimental period (~40 hours). In conclusions, the aforementioned results indicated that $Rg_1$ is an effective agent for angiogenesis and may be load in an extracellular matrix for accelerating tissue regeneration.

Some aspects of the invention relate to a method for promoting angiogenesis in a subject in need thereof, comprising administering to the subject a substrate loaded with therapeutically effective amount of a non-protein angiogenesis factor, wherein the non-protein angiogenesis factor may be an organic angiogenesis factor. In one embodiment, the non-protein angiogenesis factor is ginsenoside $Rg_1$, ginsenoside Re or the like extracted from a plant. In another embodiment, the substrate is configured and formulated for administering to the subject by a route selected from a group consisting of oral administration, topical administration, percutaneous injection, intravenous injection, intramuscular injection, oral administration, and implantation.

In one embodiment, the substrate is an acellular tissue or a wound dressing, wherein the acellular tissue may have increased porosity over the substrate by at least 5%. In another embodiment, the method for administering to a subject a substrate loaded with therapeutically effective amount of a non-protein angiogenesis factor comprises a step of crosslinking the substrate with a crosslinking agent. In a further embodiment, the substrate is an artificial organ selected from a group consisting of biological patch, vascular graft, heart valve, venous valve, tendon, ligament, bone, muscle, cartilage, ureter, urinary bladder, dermal graft, cardiac tissue, anti-adhesion membrane, and myocardial tissue.

Biological Solution Kits

Figure 27:
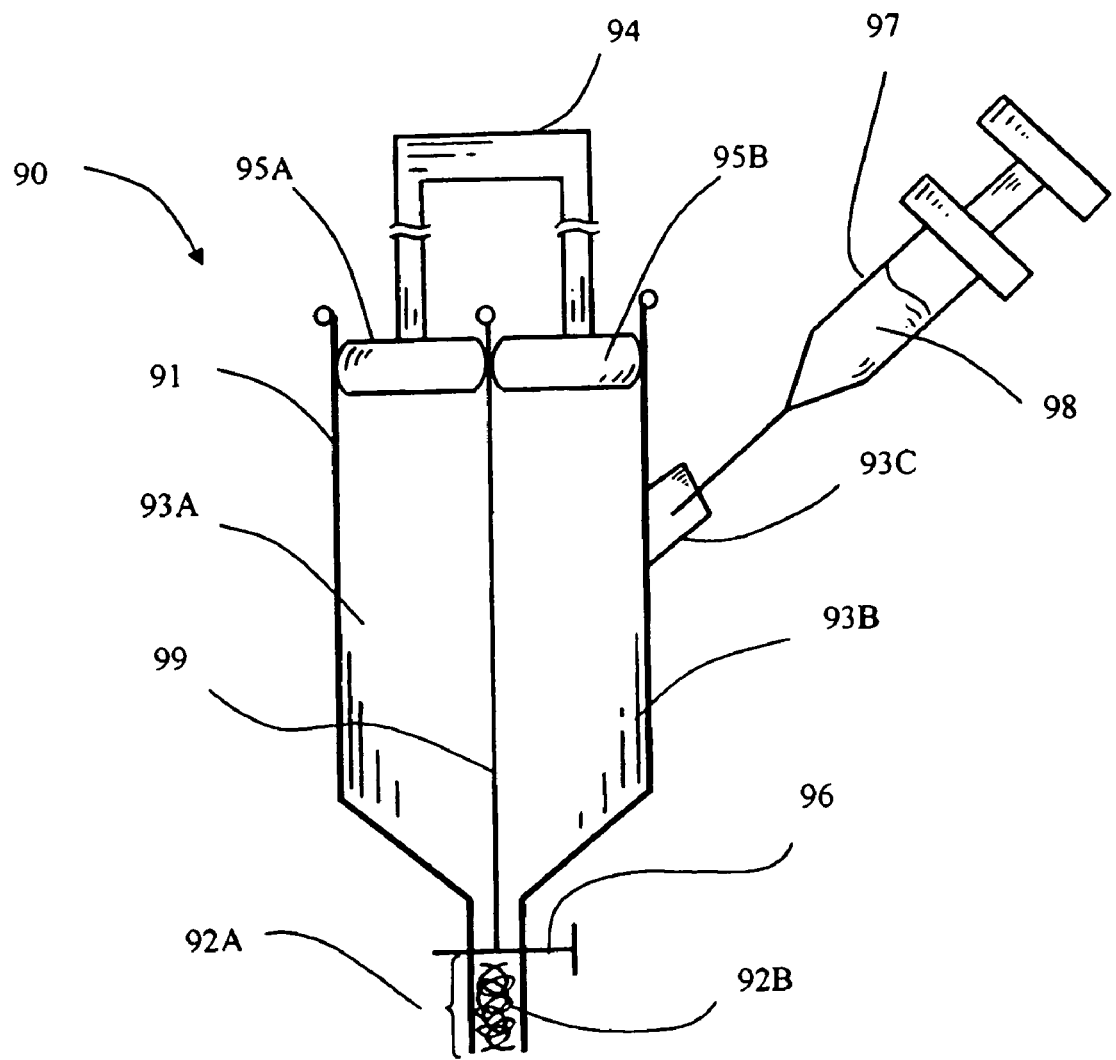
FIG. 27 is a crosslinkable biological solution kit comprising a first crosslinkable biological solution component and a second crosslinker component.

FIG. 27 shows a crosslinkable biological solution kit 90 comprising a first crosslinkable biological solution component 93B and a second crosslinker component 93A. The kit has a double-barrel cylinder 91 with a divider 99 that separates the crosslinkable biological solution component 93B from the crosslinker component 93A before use, wherein each barrel is appropriately sized and configured to provide a desired amount and ratio of each component for later mixing and application. The kit further comprises an end portion 92A with (optionally) appropriate mixing means 92B for mixing the liquid/solution from each of the double-barrel. A control valve 96 is provided to maintain the components 93A, 93B in their own barrels before use or is activated to start the mixing process. The plunger means 94 for pressurizing the components 93A, 93B toward the end portion 92A has a first plunger 95A and a second plunger 95B. In an alternate embodiment, the plunger means 94 can be either mechanical or equipped with a gas or liquid compressor. In one preferred embodiment, the mixed solution can be sprayed onto an implant or a stent. In another embodiment, the mixed solution is used directly onto a target tissue. In a further embodiment, the cylinder comprises a liquid input port 93C, wherein the bioactive agent(s) 98 can be injected via the injecting applicator 97 into and mixed with the crosslinkable biological solution component 93B.

EXAMPLE 9

Biological Solution as Medical Material

The first step for preparing a biological solution as medical material is to load the double-barrel cylinder with 4 mg/ml collagen solution at a pH4 as crosslinkable biological solution component 93B. The second step is to load 0.5% genipin solution as the crosslinker component 93A. Each of the double-barrel is appropriately sized and configured to provide a desired ratio and amount of each component 93A, 93B for later mixing in the end portion 92A. One example is to provide 0.6 ml of component 93A with respect to 4 ml of component 93B. Upon receiving the cylinder in sterile conditions, an operator as end-users prepares a paclitaxel solution (Solution A) by mixing 20 mg paclitaxel in one ml absolute alcohol, wherein Solution A is readily mixed into the component 93B by the operator. Paclitaxel is used as a bioactive agent in this example. When use, two barrels are pushed to mix the component 93A and component 93B that contains the desired bioactive agent. In one embodiment, the mixed crosslinkable biological solution is loaded onto a stent at about 30° C. temperature and subsequently leave the coated stent at 37° C. to solidify collagen, evaporate acetic acid, and crosslink collagen on the stent. The loading process may comprise spray coating, dip coating, plasma coating, painting or other known techniques. In another embodiment, the crosslinkable biological solution is administered or delivered to the target tissue accompanied with means for adjusting the biological solution to pH7, either by removing excess acetic acid or by neutralizing with a base solution.

It is one object of the present invention to provide a drug-collagen-genipin and/or drug-chitosan-genipin compound that is loadable onto an implant/stent or deliverable to a target tissue enabling drug slow-release to the target tissue. In one preferred embodiment, the compound is loaded onto the outer periphery of the stent enabling drug slow-release to the surrounding tissue.

The drugs used in the current generation drug eluting cardiovascular stents include two major mechanisms: cytotoxic and cytostatic. Some aspects of the invention relating to the drugs used in collagen-drug-genipin compound from the category of cytotoxic mechanism comprise actinomycin D, paclitaxel, vincristin, methotrexate, and angiopeptin. Some aspects of the invention relating to the drugs used in collagen-drug-genipin compound from the category of cytostatic mechanism comprise batimastat, halofuginone, sirolimus, tacrolimus, everolimus, tranilast, ABT-578 (a sirolimus analog manufactured by Abbott Labs) dexamethasone, and mycophenylic acid (MPA). Some aspects of the present invention provide a bioactive agent in a bioactive agent-eluting device, wherein the bioactive agent is selected from a group consisting of actinomycin D, paclitaxel, vincristin, methotrexate, and angiopeptin, batimastat, halofuginone, sirolimus, tacrolimus, everolimus, tranilast, dexamethasone, and mycophenylic acid.

Everolimus with molecular weight of 958 (a chemical formula of $C_{53}H_{83}NO_{14}$) is poorly soluble in water and is a novel proliferation inhibitor. There is no clear upper therapeutic limit of everolimus. However, thrombocytopenia occurs at a rate of 17% at everolimus trough serum concentrations above 7.8 ng/ml in renal transplant recipients (Expert Opin Investig Drugs 2002; 11(12):1845–1857). In a patient, everolimus binds to cytosolic immunophyllin FKBP12 to inhibit growth factor-driven cell proliferation. Everolimus has shown promising results in animal studies, demonstrating a 50% reduction of neointimal proliferation compared with a control bare metal stent.

Straub et al. in U.S. Pat. No. 6,395,300 discloses a wide variety of drugs that are useful in the methods and compositions described herein, entire contents of which, including a variety of drugs, are incorporated herein by reference. Drugs contemplated for use in the compositions described in U.S. Pat. No. 6,395,300 and herein disclosed include the following categories and examples of drugs and alternative forms of these drugs such as alternative salt forms, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antiasthamatics (e.g., ketotifen and traxanox);

antibiotics (e.g., neomycin, streptomycin, chloramphenicol, cephalosporin, ampicillin, penicillin, tetracycline, and ciprofloxacin);

antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline);

antidiabetics (e.g., biguanides and sulfonylurea derivatives);

antifungal agents (e.g., griseofulvin, ketoconazole, itraconizole, amphotericin B, nystatin, and candicidin);

antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine);

anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone);

antineoplastics (e.g., cyclophosphamide, actinomycin, bleomycin, daunorubicin, doxorubicin hydrochloride, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, piposulfan);

antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene);

immunosuppressive agents (e.g., cyclosporine, azathioprine, mizoribine, and FK506 (tacrolimus));

antimigraine agents (e.g., ergotamine, propanolol, isometheptene mucate, and dichloralphenazone);

sedatives/hypnotics (e.g., barbiturates such as pentobarbital, pentobarbital, and secobarbital; and benzodiazapines such as flurazepam hydrochloride, triazolam, and midazolam);

antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate);

antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine);

antimanic agents (e.g., lithium carbonate);

antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine);

antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium);

antigout agents (e.g., colchicine, and allopurinol);

anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

anticonvulsants (e.g., valproic acid, divalproex sodium, phenyloin, phenyloin sodium, clonazepam, primidone, phenobarbitol, carbamazepine, amobarbital sodium, methsuximide, metharbital, mephobarbital, mephenyloin, phensuximide, paramethadione, ethotoin, phenacemide, secobarbitol sodium, clorazepate dipotassium, and trimethadione);

antiparkinson agents (e.g., ethosuximide);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine);

agents useful for calcium regulation (e.g., calcitonin, and parathyroid hormone);

antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, cefoperazone sodium, cefotetan disodium, cefuroxime azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin);

anti-infectives (e.g., GM-CSF);

bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate;

terbutaline sulfate; triamcinolone; theophylline; nedocromil sodium; metaproterenol sulfate; albuterol; flunisolide; fluticasone proprionate;

steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium);

hypoglycemic agents (e.g., human insulin, purified beef insulin, purified pork insulin, glyburide, chlorpropamide, glipizide, tolbutamide, and tolazamide);

hypolipidemic agents (e.g., clofibrate, dextrothyroxine sodium, probucol, pravastitin, atorvastatin, lovastatin, and niacin);

proteins (e.g., DNase, alginase, superoxide dismutase, and lipase);

nucleic acids (e.g., sense or anti-sense nucleic acids encoding any therapeutically useful protein, including any of the proteins described herein);

agents useful for erythropoiesis stimulation (e.g., erythropoietin);

antiulcer/antireflux agents (e.g., famotidine, cimetidine, and ranitidine hydrochloride);

antinauseants/antiemetics (e.g., meclizine hydrochloride, nabilone, prochlorperazine, dimenhydrinate, promethazine hydrochloride, thiethylperazine, and scopolamine);

as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramnycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. These drugs are generally considered to be water soluble.

Preferred drugs useful in the present invention may include albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, omeprazole, rubitecan, amlodipine besylate/benazepril hydrochloride, etodolac, paroxetine hydrochloride, paclitaxel, atovaquone, felodipine, podofilox, paricalcitol, betamethasone dipropionate, fentanyl, pramipexole dihydrochloride, Vitamin $D_3$ and related analogues, finasteride, quetiapine fumarate, alprostadil, candesartan, cilexetil, fluconazole, ritonavir, busulfan, carbamazepine, flumazenil, risperidone, carbemazepine, carbidopa, levodopa, ganciclovir, saquinavir, amprenavir, carboplatin, glyburide, sertraline hydrochloride, rofecoxib carvedilol, clobustasol, diflucortolone, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, diclofenac sodium, lomefloxacin hydrochloride, tirofiban hydrochloride, telmisartan, diazapam, loratadine, toremifene citrate, thalidomide, dinoprostone, mefloquine hydrochloride, trandolapril, docetaxel, mitoxantrone hydrochloride, tretinoin, etodolac, triamcinolone acetate, estradiol, ursodiol, nelfinavir mesylate, indinavir, beclomethasone dipropionate, oxaprozin, flutamide, famotidine, nifedipine, prednisone, cefuroxime, lorazepam, digoxin, lovastatin, griseofulvin, naproxen, ibuprofen, isotretinoin, tamoxifen citrate, nimodipine, amiodarone, and alprazolam.

Specific non-limiting examples of some drugs that fall under the above categories include paclitaxel, docetaxel and derivatives, epothilones, nitric oxide release agents, heparin, aspirin, coumadin, PPACK, hirudin, polypeptide from angiostatin and endostatin, methotrexate, 5-fluorouracil, estradiol, P-selectin Glycoprotein ligand-1 chimera, abciximab, exochelin, eleutherobin and sarcodictyin, fludarabine, sirolimus, tranilast, VEGF, transforming growth factor (TGF)-beta, Insulin-like growth factor (IGF), platelet derived growth factor (PDGF), fibroblast growth factor (FGF), RGD peptide, beta or gamma ray emitter (radioactive) agents, and dexamethasone, tacrolimus, actinomycin-D, batimastat etc.

Sirolimus is a naturally occurring macrolide antibiotic produced by the fungus *Streptomyces* found in Easter Island. It was discovered by Wyeth-Ayerst in 1974 while screening fermentation products. Sirolimus with molecular weight of 916 (a chemical formula of $C_{51}H_{79}NO_{13}$) is non-water soluble and is a potential inhibitor of cytokine and growth factor mediated cell proliferation. FDA approved its use as oral immunosuppressive agents with a formulation of 2 to 5 mg/dose. The suggested drug-eluting efficacy is about 140 micrograms/cm$^2$, 95% drug release at 90 days and 30% drug-to-polymer ratio. Some aspects of the invention provide a method for administering to a subject a substrate loaded with therapeutically effective amount of at least one bioactive agent formulated for oral administration.

In some aspect of the present invention, the drug (also referred as a bioactive agent) may broadly comprise, but not limited to, synthetic chemicals, biotechnology-derived molecules, herbs, health food, extracts, and/or alternate medicines; for example, including allicin and its corresponding garlic extract, ginsenosides and the corresponding ginseng extract, flavone/terpene lactone and the corresponding *ginkgo biloba* extract, glycyrrhetinic acid and the corresponding licorice extract, and polyphenyl/proanthocyanides and the corresponding grape seed extract.

Local Atherosclerosis Reducing Agent

It was reported in *JAMA*. 2003; 290:2292–2300 and 2322–2324, entire contents of which are incorporated herein by reference, that infusion of Milano Apoprotein causes rapid regression of atherosclerosis in patients with acute coronary syndromes (ACS), according to the results of a preliminary randomized trial published in the November 5 issue of The Journal of the American Medical Association. This intravenous therapy targeting high-density lipoprotein cholesterol (HDL-C) may represent a new approach to the future treatment of atherosclerosis. "Approximately 40 carriers with a naturally occurring variant of apolipoprotein A-I known as ApoA-I Milano are characterized by very low levels of HDL-C, apparent longevity, and much less atherosclerosis than expected for their HDL-C levels," write Steven E. Nissen, Md., from the Cleveland Clinic Foundation in Ohio, and colleagues. Of 123 patients with ACS, aged 38 to 82 years, who were screened between November 2001 and March 2003 at 10 U.S. centers, 57 patients were randomized. Of 47 patients who completed the protocol, 11 received placebo, 21 received low-dose and 15 received high-dose recombinant ApoA-I Milano/phospholipid complexes (ETC-216) by intravenous infusion at weekly intervals for five doses. Some aspects of the invention provide a method for administering to a subject a substrate loaded with therapeutically effective amount of at least one bioactive agent formulated for intravenous infusion. Serial intravascular ultrasound measurements within two weeks of ACS and after treatment revealed that the mean percentage of atheroma volume decreased by 1.06% in the combined ETC-216 group compared with an increase of 0.14% in the placebo group. In the combined treatment groups, the absolute reduction in atheroma volume was a 4.2% decrease from baseline.

This initial trial of an exogenously produced HDL mimetic demonstrated significant evidence of rapid regression of atherosclerosis. The authors write, "the potential utility of the new approach must be fully explored in a larger patient population with longer follow-up, assessing a variety of clinical end points, including morbidity and mortality". In an accompanying editorial, Daniel J. Rader, MD, from the University of Pennsylvania School of Medicine in Philadelphia, discusses several study limitations, including small sample size, short treatment duration, unclear relationship of intravascular ultrasound findings to clinical benefit, and failure to compare infusion of normal ApoA-I with that of ApoA-I Milano.

The mechanisms of action of ApoA-I Milano and phospholipid complex that result in regression of atherosclerosis are unknown but presumably are related to an increase in reverse cholesterol transport from atheromatous lesions to the serum with subsequent modification and removal by the liver (*JAMA*. 2003; 290:2292–2300). The cysteine substitution for arginine at position 173 for the ApoA-I Milano variant allows dimerization, forming large HDL particles that may be particularly active in reverse cholesterol transport. In vitro experiments have demonstrated increased cholesterol efflux from cholesterol-loaded hepatoma cells incubated with serum from ApoA-I Milano carriers or from transgenic mice. As a result, some day patients with acute coronary syndromes may receive 'acute induction therapy' with HDL-based therapies for rapid regression and stabilization of lesions, followed by long-term therapy to prevent the regrowth of these lesions. In this model, long-term HDL-based therapies will still be needed as a vital component of the preventive phase.

The bioactive agent of the present invention further comprises ApoA-I Milano, recombinant ApoA-I Milano/phospholipid complexes (ETC-216), and the like (as atherosclerosis reducing agent). In one embodiment, the atherosclerosis reducing agent is used to treat both stenotic plaque and vulnerable plaque of a patient for regression and stabilization of lesions. Some aspects of the invention relate to a method for promoting atherosclerosis regression comprising: providing crosslinkable biological solution to the target tissue, wherein the crosslinkable biological solution is loaded with at least one atherosclerosis reducing agent. In one embodiment, the at least one atherosclerosis reducing agent comprises ApoA-I Milano or recombinant ApoA-I Milano/phospholipid complexes.

While the preventive and treatment properties of the foregoing therapeutic substances, agents, drugs, or bioactive agents are well known to those having ordinary skill in the art, the substances or agents are provided by way of example and are not meant to be limiting. Other therapeutic substances are equally applicable for use with the disclosed methods, devices, and compositions.

It is another object of the present invention to provide a crosslinkable biological solution kit comprising a first readily mixable crosslinkable biological solution component and a second crosslinker component, wherein an operator can add appropriate drug or bioactive agent to the kit and obtain a drug-collagen-genipin and/or drug-chitosan-genipin compound that is loadable onto an implant/stent or deliverable to a target tissue enabling drug slow-release to the target tissue. In a further embodiment, the crosslinkable biological solution kit is packaged in a form for topical administration, for percutaneous injection, for intravenous injection, for intramuscular injection, for loading on an implant or biological tissue material, and/or for oral administration.

Some aspects of the invention provide a method for promoting angiogenesis for treating tissue, comprising: providing crosslinkable biological solution to the target tissue, wherein the crosslinkable biological solution is loaded with at least one angiogenesis factor. In one embodiment, the crosslinkable biological solution to treat the target tissue is a kit comprising a first readily mixable crosslinkable biological solution component and a second crosslinker component, wherein the first component and the second component are mixed at point of need. The point of need may comprise the operating suite, a hospital room, a physician clinic, the local tissue site of a patient needed for treatment, or the device to have enhanced angiogenesis, and the like. In one embodiment, the at least one angiogenesis factor is a protein factor selected from a group consisting of VEGF, VEGF 2, bFGF, VEGF121, VEGF165, VEGF189, VEGF206, PDGF, PDAF, TGF-β, TGF-α, PDEGF, PDWHF, epidermal growth factor, insulin-like growth factor, aFGF, human growth factor, and combination thereof. In another embodiment, the at least one angiogenesis factor is a non-protein factor selected from a group consisting of ginsenoside $Rg_1$, ginsenoside Re, and combination thereof. In s a further embodiment, the crosslinkable biological solution is in a form of solution, paste, gel, suspension, colloid, or plasma, wherein the crosslinkable biological solution is crosslinkable with a crosslinking agent or with ultraviolet irradiation.

Some aspects of the invention relate to a crosslinkable biological solution kit comprising at least one bioactive agent selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, and anti-infectives. In a further embodiment, the crosslinkable biological solution kit may comprise at least one bioactive agent selected from a group consisting of actinomycin D, paclitaxel, vincristin, methotrexate, and angiopeptin, batimastat, halofuginone, sirolimus, tacrolimus, everolimus, tranilast, ABT-578, dexamethasone, mycophenylic acid, lovastatin, thromboxane $A_2$ synthetase inhibitors, eicosapentanoic acid, ciprostene, trapidil, angiotensin convening enzyme inhibitors, heparin, and biological cells.

Some aspects of the invention provide the crosslinkable biological solution kit that is configured and packaged in a form suitable for application selected from a group consisting of topical administration, percutaneous injection, intravenous injection, intramuscular injection, oral administration, and loading on an implant before implantation or after implantation.

Some aspects of the invention relate to a method for promoting angiogenesis comprising administering ginsenoside $Rg_1$ and/or ginsenoside Re onto tissue after radiation therapy to promote neovascularization. Some further aspects of the invention relate to a method for promoting angiogenesis comprising administering ginsenoside $Rg_1$ and/or ginsenoside Re onto tissue of ulcer or diabetes to promote neovascularization.

From the foregoing description, it should now be appreciated that a novel and unobvious process for promoting angiogenesis has been disclosed for tissue engineering applications. While the invention has been described with reference to a specific embodiment, the description is illustrative of the invention and is not to be construed as limiting the invention. Various modifications and applications may occur to those who are skilled in the art, without departing from the true spirit and scope of the invention.

We claim:

1. A method for promoting angiogenesis in a subject in need thereof, comprising administering to said subject a substrate loaded with therapeutically effective amount of angiogenesis factor selected from the group consisting of isolated ginsenoside $Rg_1$, isolated ginsenoside Re or combinations thereof, wherein the substrate is an artificial organ selected from the group consisting of biological patch, cardiac tissue anti-adhesion membrane and myocardial tissue, wherein the substrate is crosslinked with an agent selected from the group consisting of genepin, epoxy compounds, dialdehyde starch, glutaraldehyde, formaldehyde, dimethyl suberimide, carbodiimides, succinimidyls, diisocyanates, acyl azide, tris(hydroxymethyl)phosphine, ascorbate-copper, glucose-lysine and photo-oxidizers.

2. The method of claim 1, wherein the substrate is configured and formulate for administering to said subject by a route selected from a group consisting of topical administration, percutaneous injection, intravenous injection, intramuscular injection, oral administration, and implantation.

3. The method of claim 1, wherein the substrate is an acellular tissue or a wound dressing.

4. The method of claim 3, wherein the acellular tissue has increased porosity over the substrate by at least 5%.

5. A method for promoting angiogenesis for treating a target tissue of a patient, comprising: providing crosslinkable biological fluid medium consisting of biopolymers selected from the group of collagen extract, soluble collagen, elastin, gelatin, chitosan, N,O-carboxymethyl chitosan (NOCC) to the target tissue, wherein the crosslinkable biological fluid medium is loaded with at least one angiogenesis factor selected from the group consisting of purified ginsenoside $Rg_1$, purified ginsenoside Re or combinations thereof.

6. The method of claim 5, wherein the crosslinkable biological fluid medium is in a form of solution, paste, gel, suspension, colloid, or plasma.

7. The method of claim 5, wherein the crosslinkable biological fluid medium is crosslinked with a crosslinking agent or with ultraviolet irradiation.

8. A crosslinkable biological solution kit comprising a first readily mixable crosslinkable biological solution component and a second crosslinker component, selected from the group consisting of genepin, epoxy compounds, dialdehyde starch, glutaraldehyde, formaldehyde, dimethyl suberimide, carbodiimides, succinimidyls, diisocyanates, acyl azide, tris(hydroxymethyl)phosphine, ascorbate-copper, glucose-lysine and photo-oxidizers, wherein the first component and the second component are mixed at point of need, wherein said first readily mixable crosslinkable biological solution component is selected from the group consisting of purified ginsenoside $Rg_1$, purified ginsenoside Re or combinations thereof.

* * * * *